(12) United States Patent
Witter et al.

(10) Patent No.: US 11,993,602 B2
(45) Date of Patent: May 28, 2024

(54) PRMT5 INHIBITORS

(71) Applicants: Merck Sharp & Dohme LLC, Rahway, NJ (US); David Witter, Norfolk, MA (US); Shuhei Kawamura, Cambridge, MA (US); Michelle Machacek, Belmont, MA (US); Ryan Quiroz, Boston, MA (US); Michael H. Reutershan, Brighton, MA (US); Sebastian Schneider, Boston, MA (US); Phieng Siliphaivanh, Newton, MA (US); Yingchun Ye, Belmont, MA (US); Charles S. Yeung, Dedham, MA (US)

(72) Inventors: David Witter, Norfolk, MA (US); Shuhei Kawamura, Cambridge, MA (US); Michelle Machacek, Belmont, MA (US); Ryan Quiroz, Boston, MA (US); Michael H. Reutershan, Brighton, MA (US); Sebastian Schneider, Boston, MA (US); Phieng Siliphaivanh, Newton, MA (US); Yingchun Ye, Belmont, MA (US); Charles S. Yeung, Dedham, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 563 days.

(21) Appl. No.: 17/266,474

(22) PCT Filed: Aug. 5, 2019

(86) PCT No.: PCT/US2019/045040
§ 371 (c)(1),
(2) Date: Feb. 5, 2021

(87) PCT Pub. No.: WO2020/033282
PCT Pub. Date: Feb. 13, 2020

(65) Prior Publication Data
US 2021/0277009 A1    Sep. 9, 2021

Related U.S. Application Data

(60) Provisional application No. 62/715,324, filed on Aug. 7, 2018.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................. C07D 519/00
See application file for complete search history.

(56) References Cited

U.S. PATENT DOCUMENTS

| | | | |
|---|---|---|---|
| 2,789,118 | A | 4/1957 | Seymour |
| 2,990,401 | A | 6/1961 | Seymour |
| 3,048,581 | A | 8/1962 | Josef |
| 3,126,375 | A | 3/1964 | Hensel et al. |
| 3,749,712 | A | 7/1973 | Cavazza |
| 3,928,326 | A | 12/1975 | Brattsand |
| 3,929,768 | A | 12/1975 | Brattsand |
| 3,996,359 | A | 12/1976 | Brattsand |
| 4,231,938 | A | 11/1980 | Monaghan et al. |
| 4,294,926 | A | 10/1981 | Monaghan et al. |
| 4,319,039 | A | 3/1982 | Albers-schonberg |
| 4,346,227 | A | 8/1982 | Terahara et al. |
| 4,410,629 | A | 10/1983 | Terahara et al. |
| 4,444,784 | A | 4/1984 | Hoffman et al. |
| 4,537,859 | A | 8/1985 | Terahara et al. |
| 4,681,893 | A | 7/1987 | Roth |
| 4,782,084 | A | 11/1988 | Vyas et al. |

(Continued)

FOREIGN PATENT DOCUMENTS

| | | | |
|---|---|---|---|
| EP | 0604181 A1 | 6/1994 | |
| EP | 0618221 A2 | 10/1994 | |

(Continued)

OTHER PUBLICATIONS

Mao et al. Potent, Selective, and Cell Active Protein Arginine Methyltransferase5 (PRMT5) Inhibitor Developed by Structure-Based Virtual Screening and Hit Optimization, Journal of Medicinal Chemistry, 60, 6289-6304. (Year: 2017).*

(Continued)

*Primary Examiner* — Matthew P Coughlin
*Assistant Examiner* — Meghan C Heasley
(74) *Attorney, Agent, or Firm* — James T. Corcoran; Catherine D. Fitch

(57) ABSTRACT

The present invention provides a compound of Formula (I) Formula (I) or the pharmaceutically acceptable salts thereof, which are PRMT5 inhibitors.

(I)

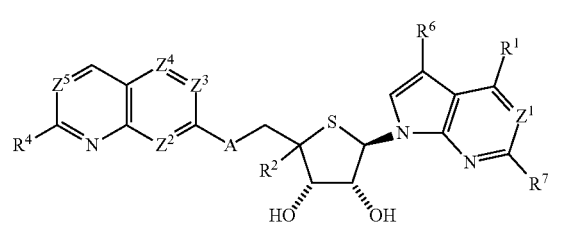

17 Claims, No Drawings

(56) References Cited

U.S. PATENT DOCUMENTS

| | | |
|---|---|---|
| 4,820,850 A | 4/1989 | Verhoeven et al. |
| 4,885,314 A | 12/1989 | Vyas et al. |
| 4,911,165 A | 3/1990 | Lennard et al. |
| 4,916,239 A | 4/1990 | Treiber |
| 4,929,437 A | 5/1990 | Tobert |
| 5,030,447 A | 7/1991 | Joshi et al. |
| 5,118,853 A | 6/1992 | Lee et al. |
| 5,134,142 A | 7/1992 | Matsuo et al. |
| 5,162,339 A | 11/1992 | Lowe, III |
| 5,177,080 A | 1/1993 | Angerbauer et al. |
| 5,180,589 A | 1/1993 | Joshi et al. |
| 5,189,164 A | 2/1993 | Kapa et al. |
| 5,232,929 A | 8/1993 | Desai |
| 5,242,930 A | 9/1993 | Baker |
| 5,273,995 A | 12/1993 | Roth |
| 5,290,946 A | 3/1994 | Lee et al. |
| 5,342,952 A | 8/1994 | Butler et al. |
| 5,344,991 A | 9/1994 | Reitz et al. |
| 5,354,772 A | 10/1994 | Kathawala |
| 5,356,896 A | 10/1994 | Kabadi et al. |
| 5,373,003 A | 12/1994 | Lowe, III |
| 5,380,738 A | 1/1995 | Norman et al. |
| 5,387,595 A | 2/1995 | Mills |
| 5,393,790 A | 2/1995 | Reitz et al. |
| 5,409,944 A | 4/1995 | Black et al. |
| 5,420,245 A | 5/1995 | Brown |
| 5,436,265 A | 7/1995 | Black et al. |
| 5,459,270 A | 10/1995 | Williams |
| 5,466,823 A | 11/1995 | Talley et al. |
| 5,474,995 A | 12/1995 | Ducharme et al. |
| 5,489,691 A | 2/1996 | Butler et al. |
| 5,494,926 A | 2/1996 | Owens |
| 5,496,833 A | 3/1996 | Baker |
| 5,510,510 A | 4/1996 | Patel |
| 5,523,430 A | 6/1996 | Patel |
| 5,532,359 A | 7/1996 | Marsters, Jr. |
| 5,536,752 A | 7/1996 | Ducharme et al. |
| 5,550,142 A | 8/1996 | Ducharme et al. |
| 5,571,792 A | 11/1996 | Bolton |
| 5,589,485 A | 12/1996 | Hochlowski |
| 5,602,098 A | 2/1997 | Sebti |
| 5,604,260 A | 2/1997 | Guay et al. |
| 5,633,272 A | 5/1997 | Talley et al. |
| 5,637,699 A | 6/1997 | Dorn |
| 5,643,958 A | 7/1997 | Iwasawa |
| 5,661,152 A | 8/1997 | Bishop |
| 5,698,584 A | 12/1997 | Black et al. |
| 5,710,140 A | 1/1998 | Ducharme et al. |
| 5,719,147 A | 2/1998 | Dorn |
| 5,728,830 A | 3/1998 | Kanda |
| 5,750,567 A | 5/1998 | Baudoin |
| 5,789,647 A | 8/1998 | Heidlas |
| 5,856,439 A | 1/1999 | Clerc |
| 5,861,419 A | 1/1999 | Dube et al. |
| 5,889,053 A | 3/1999 | Baudoin |
| 5,919,786 A | 7/1999 | Iwasawa |
| 5,932,598 A | 8/1999 | Talley et al. |
| 5,936,097 A | 8/1999 | Commercon |
| 6,001,843 A | 12/1999 | Dube et al. |
| 6,020,343 A | 2/2000 | Belley et al. |
| 6,069,134 A | 5/2000 | Roth et al. |
| RE37,314 E | 8/2001 | Hirai et al. |
| 6,284,781 B1 | 9/2001 | Danishefsky et al. |
| 6,288,237 B1 | 9/2001 | Hoefle et al. |
| 7,199,127 B2 | 4/2007 | Jeong et al. |
| 2004/0102360 A1 | 5/2004 | Barnett et al. |
| 2004/0116432 A1 | 6/2004 | Carling et al. |
| 2005/0029941 A1 | 2/2005 | Kwon |
| 2005/0043361 A1 | 2/2005 | Colca |
| 2005/0044294 A1 | 2/2005 | Vo |
| 2005/0075320 A1 | 4/2005 | Nadin |
| 2005/0176776 A1 | 8/2005 | Coleman et al. |
| 2020/0317686 A1* | 10/2020 | Vandyck ............ A61K 45/06 |

FOREIGN PATENT DOCUMENTS

| | | |
|---|---|---|
| EP | 0675112 A1 | 10/1995 |
| EP | 0696593 A2 | 2/1996 |
| WO | 1994015932 A1 | 7/1994 |
| WO | 1994019357 A1 | 9/1994 |
| WO | 1995008542 A1 | 3/1995 |
| WO | 199500516 A1 | 4/1995 |
| WO | 1995010514 A1 | 4/1995 |
| WO | 1995010515 A1 | 4/1995 |
| WO | 1995011917 A1 | 5/1995 |
| WO | 1995012572 A1 | 5/1995 |
| WO | 1995012612 A1 | 5/1995 |
| WO | 199502508 A1 | 9/1995 |
| WO | 1995024612 A1 | 9/1995 |
| WO | 1995032987 A1 | 12/1995 |
| WO | 1995034535 A1 | 12/1995 |
| WO | 1996000736 A1 | 1/1996 |
| WO | 1996005168 A1 | 2/1996 |
| WO | 1996005169 A1 | 2/1996 |
| WO | 1996005529 A1 | 2/1996 |
| WO | 1996006138 A1 | 2/1996 |
| WO | 1996006193 A1 | 2/1996 |
| WO | 1996016443 A1 | 5/1996 |
| WO | 1996017861 A1 | 6/1996 |
| WO | 1996021456 A1 | 7/1996 |
| WO | 1996021701 A2 | 7/1996 |
| WO | 1996022278 A1 | 7/1996 |
| WO | 1996024611 A1 | 8/1996 |
| WO | 1996024612 A1 | 8/1996 |
| WO | 1996030017 A1 | 10/1996 |
| WO | 1996030018 A1 | 10/1996 |
| WO | 1996030343 A1 | 10/1996 |
| WO | 1996030362 A1 | 10/1996 |
| WO | 1996030363 A1 | 10/1996 |
| WO | 1996031111 A1 | 10/1996 |
| WO | 1996031477 A1 | 10/1996 |
| WO | 1996031478 A1 | 10/1996 |
| WO | 1996031501 A1 | 10/1996 |
| WO | 1996033159 A1 | 10/1996 |
| WO | 1996034850 A1 | 11/1996 |
| WO | 1996034851 A1 | 11/1996 |
| WO | 1997000252 A1 | 1/1997 |
| WO | 1997002920 A1 | 1/1997 |
| WO | 1997003047 A1 | 1/1997 |
| WO | 1997003050 A1 | 1/1997 |
| WO | 1997004785 A1 | 2/1997 |
| WO | 1997017070 A1 | 5/1997 |
| WO | 1997018813 A1 | 5/1997 |
| WO | 1997021701 A1 | 6/1997 |
| WO | 1997023478 A1 | 7/1997 |
| WO | 1997026246 A1 | 7/1997 |
| WO | 1997030053 A1 | 8/1997 |
| WO | 1997038665 A2 | 10/1997 |
| WO | 1997044350 A1 | 11/1997 |
| WO | 1998002436 A1 | 1/1998 |
| WO | 1998028980 A1 | 7/1998 |
| WO | 1998029119 A1 | 7/1998 |
| WO | 0050032 A1 | 8/2000 |
| WO | 200044777 A1 | 8/2000 |
| WO | 200061186 A1 | 10/2000 |
| WO | 2001070677 A1 | 9/2001 |
| WO | 2001090084 A1 | 11/2001 |
| WO | 2002030912 A1 | 4/2002 |
| WO | 2002036555 A1 | 5/2002 |
| WO | 2002047671 A2 | 6/2002 |
| WO | 2002081433 A1 | 10/2002 |
| WO | 2002081435 A1 | 10/2002 |
| WO | 2002083064 A2 | 10/2002 |
| WO | 2002083138 A1 | 10/2002 |
| WO | 2002083139 A1 | 10/2002 |
| WO | 2002083140 A1 | 10/2002 |
| WO | 2003013506 A1 | 2/2003 |
| WO | 2003018543 A1 | 3/2003 |
| WO | 2003039460 A2 | 5/2003 |
| WO | 2003049527 A2 | 6/2003 |
| WO | 2003049678 A2 | 6/2003 |
| WO | 2003049679 A2 | 6/2003 |
| WO | 2003050064 A2 | 6/2003 |

(56) References Cited

FOREIGN PATENT DOCUMENTS

| WO | 2003050122 A2 | 6/2003 | |
| WO | 2003079973 A2 | 10/2003 | |
| WO | 2003084473 A2 | 10/2003 | |
| WO | 2003086279 A2 | 10/2003 | |
| WO | 2003086394 A1 | 10/2003 | |
| WO | 2003086403 A1 | 10/2003 | |
| WO | 2003086404 A1 | 10/2003 | |
| WO | 2003093251 A1 | 11/2003 | |
| WO | 2003093252 A1 | 11/2003 | |
| WO | 2003093253 A1 | 11/2003 | |
| WO | 2003093264 A1 | 11/2003 | |
| WO | 2003099211 A2 | 12/2003 | |
| WO | 2003105855 A1 | 12/2003 | |
| WO | 2003106417 A1 | 12/2003 | |
| WO | 2004031137 A1 | 4/2004 | |
| WO | 2004031138 A1 | 4/2004 | |
| WO | 2004031139 A1 | 4/2004 | |
| WO | 2004037171 A2 | 5/2004 | |
| WO | 2004039370 A1 | 5/2004 | |
| WO | 2004039774 A2 | 5/2004 | |
| WO | 2004039800 A1 | 5/2004 | |
| WO | 2004041162 A2 | 5/2004 | |
| WO | 2004058148 A2 | 7/2004 | |
| WO | 2004058700 A2 | 7/2004 | |
| WO | 2004089911 A1 | 10/2004 | |
| WO | 2004096129 A2 | 11/2004 | |
| WO | 2004096130 A2 | 11/2004 | |
| WO | 2004096131 A2 | 11/2004 | |
| WO | 2004096135 A2 | 11/2004 | |
| WO | 2004101538 A1 | 11/2004 | |
| WO | 2004101539 A1 | 11/2004 | |
| WO | 2005014553 A1 | 2/2005 | |
| WO | 2005017190 A2 | 2/2005 | |
| WO | 2005018547 A2 | 3/2005 | |
| WO | 2005018638 A1 | 3/2005 | |
| WO | 2005019205 A1 | 3/2005 | |
| WO | 2005019206 A1 | 3/2005 | |
| WO | 2005030731 A1 | 4/2005 | |
| WO | 2005100344 A1 | 10/2005 | |
| WO | 2005100356 A1 | 10/2005 | |
| WO | 2017032840 A1 | 3/2017 | |
| WO | WO-2017032840 A1 * | 3/2017 | ............. A61K 31/34 |

OTHER PUBLICATIONS

Mao, Ruifeng et al., Potent, Selective, and Cell Active Protein Arginine Methyltransferase 5 (PRMT5) Inhibitor Developed by Structure-Based Virtual Screening and Hit Optimization, Journal of Medicinal Chemistry, 2017, 6289-6304, 60.

Ben-Av et al., Induction of Vascular Endothielial Growth Factor Expression in Synovial fibroblasts by Prostaglandin E and Interleukin-1: A Potential mechanism for Inflammatory Angiogenesis, FEBS Letters, 372, 83-87, 1995.

Benezra et al., In Vivo Angiogenic Activity of Interleukins, Arch Ophthalmol, 108, 573-576, 1990.

Blume-Jensen, Peter et al., Oncogenic kinase signalling, Nature, 411, 355-365, 2001.

Bouma et al., Thrombin Activable Fibrinolysis Inhibitor (TAFI, Plasma Procarboxypeptidedase B, Procarboxypeptidase R, Procarboxypeptidase U), Thrombosis Research, 101, 329-354, 2001.

Brower, Tumor Angiogenesis New Drugs on the Block, Nature America, 17, 963-968, 1999.

Chakraborty et al., Developmental Expression of the Cyclo-Oxygenase-1 and Cyclo-oxygenase-2 genes in the Peri-implantation Mouse Uterus and their differential regulation by the blastocyst and ovarian steroids, J. Mol Endocrinol, 16, 107-122, 1996.

Chiang, Kelly et al., PRMT5 Is a Critical Regulator of Breast Cancer Stem Cell Function via Histone Methylation and FOXP1 Expression, Cell Reports, 21, 3498-3513, 2017.

Chiarugi et al., Cox-2, iNOS and p53 as play-makers of tumor angiogenesis (Review), International J. of Molecular Medicine, 2, 715-719, 1998.

Clarke, Thomas L. et al., PRMT5-Dependent Methylation of the TIP60 Coactivator RUVBL1 Is a Key Regulator of Homologous Recombination, Molecular Cell, 65, 900-916, e1-e7, 2017.

Diaz-Flores et al., Intense Vascular Sprouting From Rat Femoral Vein Induced by Prostaglandins E1 and E2, The Anatomical Record, 238, 68-76, 1994.

Fathallah-Shaykh et al., Gene Transfer of IFN-y into Established Brain Tumors Represses Grwoth by Antiangiogenesis, J. of Immunology, 164, 217-222, 2000.

Fernandez et al., Neovascularization Produced by Angiotensin II, Clinical Mediicne, 105, 141-145, 1985.

Gerhart, Sarah V. et al., Activation of the p53-MDM4 regulatory axis defines the antitumour response to PRMT5 inhibition through its role in regulating cellular splicing, Scientific Reports, 8:9711, 1-15, 2018.

Gralinkski et al., Effects of Troglitazone and Pioglitazone on Cytokine-Mediated Endothelial Cell Proliferation in Vitro, J. of Cardiovascular Pharmacology, 31, 909-913, 1998.

Gu et al., Effect of Novel CAAX Peptidomimetic Farnesyltransferase Inhibitor on Angiogenesis In Vitro and In Vivo, European J. of Cancer, 35, 1394-1401, 1999.

Hall et al., The Promise and Reality of Cancer Gene Therapy, Am. J. Hum. Genet, 61, 785-789, 1997.

Hamard, Pierre-Jacques et al., PRMT5 Regulates DNA Repair by Controlling the Alternative Splicing of Histone-Modifying Enzymes, Cell Reports, 24, 2643-2657, 2018.

Harada et al., Expression and Regulation of Vascular Endothelial Growth Factor in Osteoblasts, Clinical Ortho, 313, 76-80, 1995.

Hla et al., Human Cyclooxygenase-2 cDNA, Proc. Natl. Acad. Sci., 89, 7384-7388, 1992.

Kim et al., Inhibition of Endothelial Growth Factor-Induced Angiogenesis Suppresses Tumour Growth in Vivo, Nature, 362, 841-844, 1993.

Korte et al., Changes of the Coagulation and Fibrinolysis System n Malignancy: Their possible Impact on Future Diagnostic And Therapeutic Procedures, Clin Chem Lab Med, 38 (8), 679-692, 2000, 38.

Kufe et al., Principles of Gene Therapy, Cancer Medicine, 5th Ed., pp. 876-889, 2000.

Li et al., Adenovirus-Mediated Delivery of a uPA/uPAR Antagonist Suppresses Angiogenesis—Dependent Tumor Growth and Dissemination in Mice, Gene Therapy, 5, 1105-1113, 1998.

Majima et al., Significant Roles of Inducible Cyclooxygenase (COX)-2 in Angiogenesis in Rat Sponge Implants, Jpn. J. Pharmacol., 75, 105-114, 1997.

Miller et al., Histone Deacetylase Inhibitors, J. of Medicinal Chemistry, 46, 5097-5116, 2003.

Murata et al., Peroxisome Proliferator-Activated Receptor-y Ligands Inhibit Choroidal Neovascularization, Inestigative Ophthalmology & visual Science, 41, 2309-2317, 2000.

Murata et al., Response of Experimental Retinal Neovascularization to Thiazolidinediones, Arch Ophthamol, 119, 709-717, 2001.

Seed et al., The Inhibition of Colon-26 Adenocarcinoma Development and Angiogenesis by Topical Diclofenac in 2.5% Hyaluronan, Cancer Research, 57, 1625-1629, 1997.

Still et al., Rapid Chromatographic Technique for Preparative Separations with Moderate Resolution, J. Org. Chem., 43, 2923-2925, 1978.

Tsujii et al., Cyclooxgenase Regulates Angiogenesis Induced by Colon Cancer Cells, Cell, 93, 705-716, 1998.

Xin et al., Peroxisome Proliferator Activated Receptor y Ligands are Potent Inhibitors of Angiogenesis in Vitro and in Vivo, J. Biol Chem,, 13, 9116-9121, 1999.

Yalpani et al., Coronary Heart Disease is the most Serious Threat to life in the Western World, but Progress is Being Made in Finding Ways to Reduce the Risks of Suffering Such a Fate, Chemistry & Industry, 85-89, 1996.

Zacharski et al., Heparin and Cancer, Thromb Haemost, 80, 10-23, 1998.

Ziche et al., Role of Prostaglandin E, and Copper in Angiogenesis, JNCI, 69, 475-482, 1982.

* cited by examiner

PRMT5 INHIBITORS

CROSS REFERENCE TO RELATED APPLICATIONS

This application is a U.S. National Phase application under 35 U.S.C. § 371 of PCT Application No. PCT/US2019/045040 filed Aug. 5, 2019, which claims priority to U.S. Ser. No. 62/715,324 filed Aug. 7, 2018, the contents of which are hereby incorporated by reference in their entireties.

BACKGROUND OF THE INVENTION

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al, 1999). PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodeling components BRG1 and BRM. PRMT5 has been reported to perform diverse roles including but not limited to impacting cell viability, sternness, DNA damage repair and RNA splicing (Clarke et al., Mol Cell (2017), Chiang et al, Cell Rep (2017), Gerhart et al, Sci Rep (2018)). Specifically, inhibition of PRMT5 induces alternative splicing of the negative regulator of p53, MDM4 resulting in increased expression of the short isoform of MDM4 (MDM4-S), decreased expression of the full-length isoform (MDM4-FL) and increased p53 activity (Gerhart et al, Sci Rep (2018)).

PRMT5 is involved in the methylation and functional modulation of the tumor suppressor protein p53. (See Berger, 2008; Durant et al, 2009; Jansson et al, 2008; Scoumanne et al., 2009). Most of the physiological functions of p53 are attributable to its role as a transcriptional activator, responding to agents that damage DNA. p33 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumor suppression.

The role of PRMT5 and p53 arginine methylation on cell cycle regulation and DNA damage response have been explored by both Jansson et al, and Scoumanne et al, (Jansson et al, 2008; Scoumanne et al, 2009). Although some differences are evident between the results from the two groups concerning cell cycle regulation in unperturbed cells (which may be ascribed to cell type specific effects and/or the actual nature of the experimental arrangements), both groups report similar results with respect to the DNA damage response.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, hut not PUMA, NOXA, AlP1 & APAF1, p53 target genes linked to apoptosis.

Knockdown of PRMT5 (but not PRMT1 or CARM1/PRMT4) results in decreased p53 stabilisation, decreased basal p53 levels, decreased p53 oligomerisation, and also decreased expression of elF4E a major component of translational machinery involved in ribosome binding to mRNA. Indeed, elF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al. showed that a p53 mutant in which each of the three critical arginine residues were substituted with lysine (p53KKK) retained the ability to induce apoptosis hut its cell cycle arrest activity was significantly compromised.

Moreover, pS3KKK also has a significantly reduced ability to induce transcription of p21, by contrast with APAF1, The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

The role of PRMT5 in the DNA damage response has been explored with groups reporting a role for PRMT5 in regulating high fidelity homologous recombination mediated DNA repair in both solid (Clarke et al., Mol Cell (2017) and hematological tumor models (Hamard et al. Cell Rep (2018)).

PRMT5 is aberrantly expressed in around half of human cancer cases, further linking this mechanism to cancers. PRMT5 overexpression has been observed in patient tissue samples and cell lines of Prostate cancer (Gu et al, 2012), Lung cancer (Zhongping et al, 2012), Melanoma cancer (Nicholas et al, 2012), Breast cancer (Powers et al, 2011), Colorectal cancer (Cho et al, 2012), Gastric cancer (Kirn et al, 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphcytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al, 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al, 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetic-s in the origin and progression of CLL remains unclear, epigenetic changes appear to occur early in the disease and specific patterns of DNA methylation are associated with worse prognosis (Chen et al, 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell tines and MCL clinical samples.

PRMT5 is therefore a target for the identification of novel cancer therapeutics.

Hemoglobin is a major protein in red blood cells and is essential for the transport, of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by subunits as the infant grows. The developmental switch in human ß-like globin gene subtype from foetal (γ) to adult (ß) that begins at birth heralds the onset of the hemoglobinopathies ß-thalassemia and sickle cell disease (SCD). In ß-thalassemia tire adult chains are not produced. In SCD a point mutation in the coding sequence in the ß globin gene leads to the production of a protein with altered polymerisation properties. The observation that increased adult γ-globin gene expression (in the setting of hereditary persistence of foetal hemoglobin (HPFH) mutations) significantly ameliorates the clinical severity of ß-thalassemia and SCD has prompted the search for therapeutic strategies to reverse γ-globin gene silencing. To date, this has been achieved through pharmacological induction, using compounds that broadly influence epigenetic modifications, including DN A methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia and Sickle Cell Disease (SCD).

The present inventors have developed particular tetrahydroisoquinolines that inhibit the activity of PRMT5 and therefore may be of use in treating conditions ameliorated by the inhibition of the activity of PRMT5.

SUMMARY OF THE INVENTION

Compounds of formula I

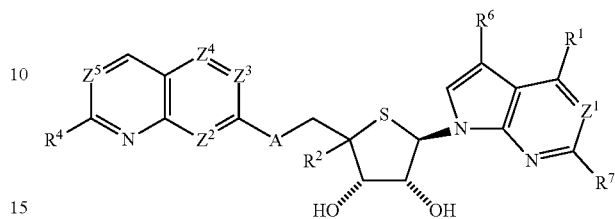

(I)

or the pharmaceutically acceptable salts, esters, and prodrugs thereof, are PRMT5 inhibitors. Also provided are pharmaceutical compositions comprising compounds of Formula I, and methods of using these compounds to treat cancer.

DETAILED DESCRIPTION OF THE INVENTION

The invention is a compound of the formula

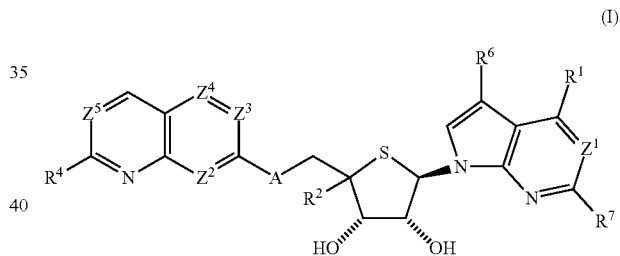

(I)

or a pharmaceutically acceptable salt thereof, wherein

A is O or $CH_2$;

$R^1$ is halogen, $N(R^9)_2$, $OC_{1-6}$alkyl, or $C_{1-6}$alkyl optionally substituted with one to three halogen or OH;

$R^2$ is H or $C_{1-6}$alkyl optionally substituted with one to three halogens;

$R^3$ is H, halogen, or $C_{1-6}$alkyl optionally substituted with one to three halogens, and $R^4$ is H or $NHR^5$, or $R^3$ and $R^4$ together with the atom to which they are attached form a 5-membered saturated ring containing zero or one N atom, wherein the ring is unsubstituted or substituted with $CH_3$;

$R^5$ is H or $C_{1-6}$alkyl optionally substituted with one to three halogens;

$R^6$ is H, $C_{1-4}$alkyl, or halogen;

$R^7$ is H, $NH_2$, or $C_{1-6}$alkyl;

$R^9$ is independently selected from H or $C_{1-6}$alkyl, wherein the $C_{1-6}$alkyl can be optionally substituted with one to three halogens or OH;

$Z^1$ is CH or N;

$Z^2$ is CH or N;

$Z^3$ is CH or N;

$Z^4$ is CH or N; and $Z^5$ is $CR^3$ or N.

A subembodiment of the invention includes compounds of Formula I, wise rein
- A is O or $CH_2$;
- $R^1$ is halogen, $NH_2$, $OC_{1-6}$alkyl, $NHCH_3$, $CHF_2$, $C_{1-6}$alkyl, cyclopropyl, $CH_2OH$, or $C(CH_3)_2OH$;
- $R^2$ is H, $C_{1-6}$alkyl, $CF_3$ or $CHF_2$;
- $R^3$ is H, halogen, $CH_3$, $CF_3$, or $CHF_2$, and $R^4$ is H or $NHR^5$, or $R^3$ and $R^4$ together with the atom to which they are attached form a 5-membered saturated ring containing zero or one N atom, wherein the ring is unsubstituted or substituted with $CH_3$;
- $R^5$ is H, $CH_3$, $C_2H_5$, $CH_2CH_2CH_3$, $CH(CH_3)_2$, $CH_2CHF_2$, $CH_2CF_3$, or $CH_2$—$C_{3-8}$cycloalkyl;
- $R^6$ is H, $C_{1-4}$alkyl, or halogen;
- $R^7$ is H, $NH_2$, or $C_{1-6}$alkyl;
- $Z^1$ is CH or N;
- $Z^2$ is CH or N;
- $Z^3$ is CH or N;
- $Z^4$ is CH or N; and
- $Z^5$ is $CR^3$ or N; or a pharmaceutically acceptable salt thereof.

In a subembodiment of the invention of formula I, $R^2$ is $CH_3$.
In a subembodiment of the invention of formula I, $R^b$ is H.
In a subembodiment of the invention of formula I, $R^b$ is F.
In a subembodiment of the invention of formula I, $R^6$ is $CH_3$.
In a subembodiment of the invention of formula I, $R^7$ is $CH_3$.
In a subembodiment of the invention of formula I, $R^7$ is $NH_2$.
In a subembodiment of the invention,
- A is O or $CH_2$;
- $R^1$ is Cl, $NH_2$, or $OCH_3$;
- $R^2$ is H or $CH_3$;
- $R^3$ is H, Br, F, $CH_3$, or Cl; and
- $R^4$ is $NH_2$ or NH—$CH_2$-cyclopropyl.

In an embodiment of the invention, the compound has the formula Ia.

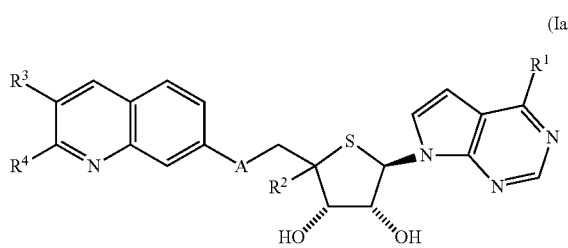

(Ia)

or a pharmaceutically acceptable salt thereof, wherein
- A is O or $CH_2$;
- $R^3$ is halogen, $NH_2$, or $OC_{1-6}$alkyl;
- $R^2$ is H or $C_{1-6}$alkyl;
- $R^3$ is H, $CH_3$, $CF_3$, $CHF_2$, or halogen;
- $R^4$ is H or $NHR^5$; and
- $R^5$ is H or $CH_2$—$C_{3-8}$cycloalkyl.

In a subembodiment of the invention of formula Ia, A is O,
In a subembodiment of the invention of formula Ia, A is $CH_2$,
In a subembodiment of the invention of formula Ia, $R^1$ is $NH_2$, Cl, $NHCH_3$, $OCH_3$, or $CH_3$.
In a subembodiment of the invention of formula Ia, $R^2$ is H or $CH_3$.
In a subembodiment of the invention of formula Ia, $R^3$ is H, Br, Cl, F, $CHF_2$, $CF_3$, or $CH_3$.
In a subembodiment of the invention of formula Ia, $R^4$ is $NH_2$.

In a subembodiment of the invention of formula Ia, $R^4$ is $NHR^5$.
In a subembodiment of the invention of formula Ia, $R^5$ is H.
In a subembodiment of the invention of formula Ia, $R^5$ is $CH_2CHF_2$.
In a subembodiment of the invention of formula Ia, $R^4$ is $NHCH_2CHF_2$.

In an embodiment of the invention, the compound has the formula Ib

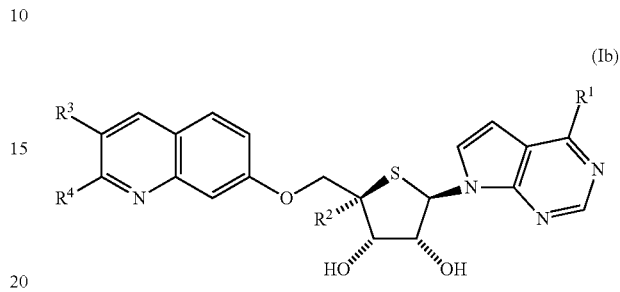

(Ib)

In an embodiment of the invention, the compound has the formula Ic

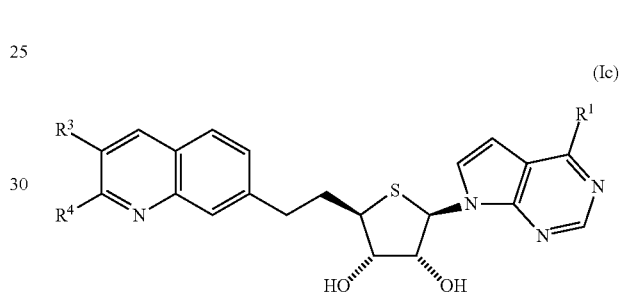

(Ic)

In an embodiment of the invention, the compound is
(2R,3S,4R,5R)-2-(((2-amino-3-bromoquinolin-7-yl)oxy)methyl)-5-(4-amino-7H-pyrrolo[2,3-d]pyrimidin-7-yl)tetrahydrothiophene-3,4-diol,
7-[5-O-(2-amino-3-chloroquinolin-7-yl)-4-thio-beta-D-ribofuranosyl]-7H-pyrrolo[2,3-d]pyrimidin-4-amine,
7-[5-O-(2-amino-3-fluoroquinolin-7-yl)-4-thio-beta-D-ribofuranosyl]-7H-pyrrolo[2,3-d]pyrimidin-4-amine,
7-(5-O-{2-[(cyclopropylmethyl)amino]quinolin-7-yl}-4-thio-beta-D-ribofuranosyl)-7H-pyrrolo[2,3-d]pyrimidin-4-amine,
(2R,3S,4R,5R)-2-(((2-amino-3-chloroquinolin-7-yl)oxy)methyl)-5-(4-amino-7H-pyrrolo[2,3-d]pyrimidin-7-yl)tetrahydrothiophene-3,4-diol,
(2R,3S,4R,5R)-2-(((2-amino-3-bromoquinolin-7-yl)oxy)methyl)-5-(4-chloro-7H-pyrrolo[2,3-d]pyrimidin-7-yl)-2-methyltetrahydrothiophene-3,4-diol,
(2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrothiophene-3,4-diol,
(2R,3S,4R,5R)-2-(((2-((cyclopropylmethyl)amino)quinolin-7yl)oxy)methyl)-5-(4-methoxy-7H-pyrrolo[2,3-d]pyrimidin-7-yl)tetrahydrothiophene-3,4-diol,
(2R,3S,4R,5R)-2-(((2-((cyclopropylmethyl)amino)quinolin-7-yl)oxy)methyl)-5-(4-methyl-7H-pyrrolo[2,3d]pyrimidin-7yl)tetrahydrothiophene-3,4-diol,
(2R,3S,4R,5R)-2-(((2-aminoquinolin-7-yl)oxy)methyl)-5-(4-methoxy-7H-pyrrolo[2,3-d]pyrimidin-7-yl)tetrahydrothiophene-3,4-diol,
(2R,3R,4S,5R)-2-(4-amino-7H-pyrrolo[2,3-d]pyrimidin-7-yl)-5-(((2-aminoquinolin-7 yl)oxy)methyl)tetrahydrothiophene-3,4-diol, (2R,3S,4R,5R)-2-(2-(2-amino-3-bromoquinolin-7-yl)
ethyl)-5-(4-amino-7H-pyrrolo[2,3-d]pyrimidin-7-yl)tetrahydrothiophene-3,4-diol,
(2S,3S,4R,5R)-2-(2-(2-amino-3-bromoquinolin-7-yl)ethyl)-
5-(4-amino-7H-pyrrolo[2,3-d]pyrimidin-7-yl)tetrahydrothiophene-3,4-diol,
(2R,3R,4S,5R)-2-(4-amino-7H-pyrrolo[2,3-d]pyrimidin-7-yl)-5-(2-(2-aminoquinolin-7-yl)ethyl)tetrahydrothiophene-3,4-diol,
(2R,3R,4S,5S)-2-(4-amino-7H-pyrrolo[2,3-d]pyrimidin-7-yl)-5-(2-(2-aminoquinolin-7-yl)ethyl)tetrahydrothiophene-3,4-diol,
(2S,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol,
(2R,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-5-(4-methyl-7H-pyrrolo[2,3-d]pyrimidin-7-yl)tetrahydrothiophene-3,4-diol,
(2S,3S,4R,5R)-2-(2-(2-amino-3-bromoquinolin-7-yl)ethyl)-
5-(4-methyl-7H-pyrrolo[2,3-d]pyrimidin-7-yl)tetrahydrothiophene-3,4-diol,
(2R,3S,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol,
(2S,3R,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol,
(2R,3S,4R,5R)-2-[2-(2-amino-3-fluoroquinolin-7-yl)ethyl]-
5-(4-methyl-7H-pyrrolo[2,3-d]pyrimidin-7-yl)tetrahydrothiophene-3,4-diol,
(2S,3S,4R,5R)-2-[2-(2-amino-3-fluoroquinolin-7-yl)ethyl]-
5-(4-methyl-7H-pyrrolo[2,3-d]pyrimidin-7-yl)tetrahydrothiophene-3,4-diol,
(2R,3S,4R,5R)-2-[2-(2-amino-3-chloroquinolin-7-yl)ethyl]-
5-(4-methyl-7H-pyrrolo[2,3-d]pyrimidin-7-yl)tetrahydrothiophene-3,4-diol,
(2S,3S,4R,5R)-2-[2-(2-amino-3-chloroquinolin-7-yl)ethyl]-
5-(4-methyl-7H-pyrrolo[2,3-d]pyrimidin-7-yl)tetrahydrothiophene-3,4-diol,
(2R,3S,4R,5R)-2-(2-{2-[(2,2-difluoroethyl)amino]quinolin-7-yl}ethyl)-5-(4-methyl-7H-pyrrolo[2,3-(7]pyrimidin-7-yl)tetrahydrothiophene-3,4-diol,
(2S,3S,4R,5R)-2-(2-{2-[(2,2-difluoroethyl)amino]quinolin-7-yl}ethyl)-5-(4-methyl-7H-pyrrolo[2,3-d]pyrimidin-7-yl)tetrahydrothiophene-3,4-diol,
(2R,3S,4R,5R)-2-(2-(2-amino-3-methylquinolin-7-yl)
ethyl)-5-(4-methyl-7H-pyrrolo[2,3-d]pyrimidin-7-yl)tetrahydrothiophene-3,4-diol,
(2S,3S,4R,5R)-2-(2-(2-amino-3-methylquinolin-7-yl)
ethyl)-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-5-(4-amino-7H-pyrrolo[2,3-d]pyrimidin-7-yl)-2-methyltetrahydrothiophene-3,4-diol,
(2R,3S,4R,5R)-2-(2-(2-amino-3-bromoquinolin-7-yl)
ethyl)-5-(4-chloro-7H-pyrrolo[2,3-d]pyrimidin-7-yl)-2-methyltetrahydrothiophene-3,4-diol,
(2R,3S,4R,5R)-2-(2-(2-amino-3-bromoquinolin-7-yl)
ethyl)-2-methyl-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-2-methyl-5-(4-(methylamino)-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-5-(4-amino-5-methyl-7H-pyrrolo[2,3-d]pyrimidin-7-yl)tetrahydrothiophene-3,4-diol,
(2R,3R,4S,5R)-2-(4-amino-2-methyl-7H-pyrrolo[2,3-d]pyrimidin-7-yl)-5-(2-(2-amino-3-bromoquinolin-7-yl)ethyl)
tetrahydrothiophene-3,4-diol,
(2R,3S,4R,5R)-2-(2-(2-amino-3-bromoquinolin-7-yl)
ethyl)-5-(4-(methylamino)-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-5-(4-amino-5-fluoro-7H-pyrrolo[2,3-d]pyrimidin-7-yl)tetrahydrothiophene-3,4-diol,
(2R,3S,4R,5R)-2-(2-(2-amino-3-bromoquinolin-7-yl)
ethyl)-5-(2-amino-4-methyl-7H-pyrrolo[2,3-d]pyrimidin-7-yl)tetrahydrothiophene-3,4-diol,
(2S,3S,4R,5R)-2-(2-((R)-2-methyl-2,3-dihydro-1H-pyrrolo
[2,3-b]quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-((S)-2-methyl-2,3-dihydro-1H-pyrrolo
[2,3-b]quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-(difluoromethyl)quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-chloroquinolin-7-yl)ethyl)-
5-(4-amino-7H-pyrrolo[2,3-d]pyrimidin-7-yl)tetrahydrothiophene-3,4-diol, or
(2R,3S,4R,5R)-2-(2-(2-amino-3-chloroquinolin-7-yl)ethyl)-
5-(4-amino-7H-pyrrolo[2,3-d]pyrimidin-7-yl)tetrahydrothiophene-3,4-diol.

The term "composition" is intended to encompass a product comprising the specified ingredients in the specified amounts, as well as any product which results, directly or indirectly, from combination of the specified ingredients in the specified amounts. The term "anti-cancer agent" means a drag (medicament or pharmaceutically active ingredient) for treating cancer. The term "antineoplastic agent" means a drug (medicament or pharmaceutically active ingredient) for treating cancer (i.e., a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "consecutively" means one following the other. The term "effective amount" means a "therapeutically effective amount". The term "therapeutically effective amount" means that amount of active compound or pharmaceutical agent that elicits the biological or medicinal response in a tissue, system, animal or human that is being sought by a researcher veterinarian, medical doctor or other clinician. Thus, for example, in the methods of treating cancer described herein "effective amount" (or "therapeutically effective amount") means, the amount of the compound (or drag), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e., a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of Formula I and a pharmaceutically acceptable carrier. The invention also provides a pharmaceutical composition comprising an effective amount of at least one compound of Formula I and an effective amount of at least one other pharmaceutically active ingredient (such as, for example, a chemotherapeutic agent), and a pharmaceutically acceptable carrier.

The invention also provides a method of inhibiting PRMT5 in a patient in need of such treatment comprising administering to said patient an effective amount of at least one compound of Formula I. The invention also provides a method for treating cancer in a patient in need of such treatment, said method comprising administering to said patient an effective amount of at least one compound of Formula I. The invention also provides a method for treating cancer in a patient in need of such treatment, said method comprising administering to said patient an effective amount of at least one compound of Formula I, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of Formula I. Another example of the invention is directed to a method of treating cancer in a patient in need of such treatment, said method comprising administering to said patient an effective amount of a compound of Formula I, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, EEC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced, and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician considers such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The compounds of the invention are also useful in preparing a medicament that is useful in treating cancer. The invention also includes a compound of Formula I for use in treating cancer in a patient in need thereof.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), ehoiangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous eystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzurnab (e.g., Herceptin), Gefitinib (e.g., Iressa), Erlotmib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of Formula I, or a pharmaceutically acceptable salt thereof, to said patient. Another example of the invention is directed to a method of treating colo-rectal cancer in a patient in need of such treatment, said method comprising administering to said patient an effective amount of a compound of Formula I, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of Formula I, or a pharmaceutically acceptable salt thereof, to said patient. Another example of the invention is directed to a method of treating melanoma in a patient in need of such treatment, said method comprising administering to said patient an effective amount of a compound of Formula I, or a pharmaceutically acceptable salt thereof, and an effective amount of at least one chemotherapeutic agent.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $10^{th}$ edition (2015), Wolters Kluwer. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, 80 bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dimtrophenyl-hydrazone, and SH646.

PD-1 inhibitors include pembrolizumab (lambrolizumab), nivolumab and MPDL3280A. PD-L1 inhibitors include atezolizumab, avelumab, and durvalumab.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitoi, ranimustine, fotemustine, nedaplatin, oxalipiatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN 10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include pachtaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 or 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, temposide, sobuzoxane, 2'dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylaminoethyl]-5-(4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-

7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK: in particular inhibitors of PLK-1), inhibitors of bub-1 and inhibitors of bub-R1. An example of an "aurora kinase inhibitor" is VX-680 (tozasertib).

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytaxabine ocfosfate, fosteabine sodium hydrate, raltitrexed, paltitrexid, emitefur, tiazofurin, decitabme, nolatrexed, pemetrexed, nelzarabme, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsomne, lometrexol, dexrazoxane, methioninase, 2'cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and rosuvastatin (CRESTOR® U.S. Reissue Pat. No. RE37,314) cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", (Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type 1 (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, and 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib, etoricoxib, and rofecoxib (*PNAS*, Vol, 89, p. 7384 (1992); *JNCI*, Vol. 69, p. 475 (1982); *Arch Opthalmol*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p, 1625 (1997); *Cell*, Vol. 93, p. 705 (1998); *Intl. J. Mol. Med.*, Vol. 2, p, 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone). carboxyamidotriazole, combretastatin A-4, squalamine, 6-O-chloroacetyl-carbonyl)-fumagillol, thalidomide, angiostatin, troponin-1, angiotensin II antagonists (see Fernandez et al, *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in din. Chem. La. Med. 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of AIR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by ceil or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, hut are not limited to, the following: rofecoxib, etoricoxib, parecoxib, B EXTRA® and CELEBREX®) or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldmanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\alpha_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3 fg: 3',2',1'-kl]pyrrolo[3,4-i][1,6]benzodiazocin-l-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazmamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ, The expression of PPAR-γ on endothelial cells and its involvement in angiogenesis has been reported in the literature (see. *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioghtazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another example of the instant invention is the use of the presently disclosed compounds in combination with gene therapy for the treatment of cancer. For an overview of genetic strategies to treating cancer see Hall et al, (*Am. J. Hum. Genet.* 61:785-789, 1997) and Kufe et al., (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8): 1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasatide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,903, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 55.5, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08.549, 95/11880, 95/14017, 95/15311, 95/16679, 95/17382, 95/18124, 9.5/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of tire instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim. A compound of tire instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of tire instant invention may also be useful for treating or preventing cancer in combination with Pgp and/or BCRP inhibitors including: cyclosporin A, PSC833, GF120918, cremophorEL, fumitremorgin C, Kol32, Kol34. Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talmolol.

A compound of tire instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Bonrva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of tire instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with tire following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-C-dA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoehn alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamyem PFS®); doxorubicin (Adriamycin®, Rubex®): doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamidn (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevaim®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan. L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamyc-In®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel proteinbound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycn, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargrarnostirn (Leukine®); Sargrarnostirn (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecaii (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vormostat (Zolinza®) and zoiedronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integral blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on tire compounds of the instant invention can be selected by one of ordinary skill in the art to provide compounds that are chemically stable and that can be readily synthesized by techniques known m the art, as well as those methods set forth below; from readily available starting materials. If a substituent is itself substituted with more than one group, it is understood that these multiple groups may be on the same carbon or on different carbons, so long as a stable structure results. Also, "optionally substituted" means unsubstituted or substituted with the specified groups, radicals or moieties.

It will be understood that, as used herein, the invention includes compounds of structural Formula I as well as the pharmaceutically acceptable salts, and also salts that are not pharmaceutically acceptable when they are used as precursors to the free compounds or their pharmaceutically acceptable salts or in other synthetic manipulations.

The compounds of the structural Formula I may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methyl bromide, methylnitrate, methyl sulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of structural Formula I carry an acidic moiety, suitable pharmaceutically acceptable salts thereof include, but are not limited to, salts derived from inorganic bases including aluminum, ammonium, calcium, copper, feme, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, methylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These sails can be obtained by known methods, for example, by mixing a compound of structural Formula I with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

Reference to the compounds of the invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

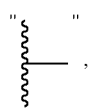

, ethyl may be represented by "Et" or $CH_2CH_3$, propyl may be represented by "Pr" or $CH_2CH_2CH_3$, butyl may be represented by "Bn" or CH₂CH₂CH₂CH₃, etc. "C_{1-4} alkyl" (or "C₁-C₄ alkyl") for example, means linear or branched chain alkyl groups, including all isomers, having the specified number of carbon atoms. For example, the structures

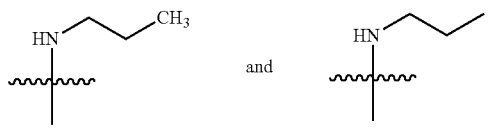

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except as noted herein, "fluoroalkyl" is intended to include both branched- and straight-chain saturated aliphatic hydrocarbon groups having the specified number of carbon atoms, substituted with 1-9 fluoro atoms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but winch can be used, for example, as intermediates for chemical reactions or for the preparation of physiologically acceptable salts.

Any pharmaceutically acceptable pro-drag modification of a compound of the invention which results in conversion in vivo to a compound within the scope of the invention is also within the scope of the invention. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —$C_{1-6}$alkyl esters and —$C_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Substituents can be represented with or without a dash, '-', in front of the substituent.

Alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$, alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, haloaryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. Unless otherwise specified, alkyl groups are unsubstituted.

Except where noted, the term "halogen" means fluorine, chlorine, bromine or iodine.

Except where noted, the term "saturated heterocycle" refers to a stable 4- to 7-membered mono-cyclic or stable 7- to 12-membered bicyclic or stable 12- to 14-membered tricyclic heteroatom-containing ring system unsubstituted or substituted with $C_{1-4}$ alkyl or halogen, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane and homopiperazine.

Except where noted herein, the term "unsaturated heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" refers to a heterocycle having fused rings in which at least one of the rings is not fully saturated, e.g.

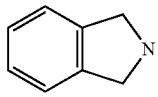

is a 9-membered unsaturated bicyclic heterocycle having one nitrogen atom.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

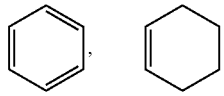 [SMILES: c1ccccc1 ; C1=CCCCC1]

Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

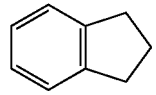

is a 9-membered unsaturated bicyclic carbocycle.

Except where noted, the term "aryl" refers to a stable 6- to 10-membered mono- or bicyclic unsaturated carbocyclic ring system such as phenyl, or naphthyl. The aryl ring can be unsubstituted or substituted with one or more of $C_{1-4}$ alkyl, hydroxyl, alkoxy, halogen, or amino.

"Celite®" (Fluka) diatomite is diatomaceous earth, and can be referred to as "celite".

Except where noted herein, structures containing substituent variables such as variable "R" below:

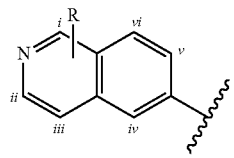

which are depicted as not being attached to any one particular bi cyclic ring carbon atom, represent structures in which the variable can be optionally attached to any bi cyclic ring carbon atom. For example, variable R shown in the above structure can be attached to any one of 6 bicyclic ring carbon atoms i, ii, iii, iv, v or vi.

Except where noted herein, a bicyclic heterocycle can be a fused bicyclic heterocycle, e.g.,

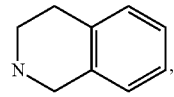

a bridged bicyclic heterocycle, e.g.,

or
a spiro bicyclic heterocycle, e.g.,

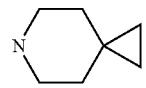

Where ring atoms are represented by variables such as "X", e.g,

the variables are defined by indicating the atom located at the variable ring position without depicting the ring bonds associated with the atom. For example, when X in the above ring is nitrogen, the definition will show "N" and will not depict the bonds associated with it, e.g., will not show "=N—". Likewise, when X is a carbon atom that is substituted with bromide, the definition will show "C—Br" and will not depict the bonds associated with it, e.g., will not show

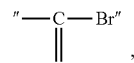

The invention also includes derivatives of the compound of Formula I, acting as prodrugs and solvates. Prodrugs, following administration to the patient are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine tire permeation properties of the drug.

The preparation of pharmacologically acceptable salts from compounds of the Formula (I) capable of salt formation, including their stereoisomeric forms is earned out in a manner known per se. With basic reagents such as hydroxides, carbonates, hydrogencarbonates, alkoxides and ammonia or organic bases, for example, trimethyl- or triethyl amine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For the, inorganic and organic acids such as hydrochloric, hydrobromic, sulfuric, hemisulfuric, phosphoric, methanesuifonic, henzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible. The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, hinders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compound s, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to tire compound where multiple substituents are optionally allowed under the definitions of Formula I hereinabove.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound of structural Formula I has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

$^1$H spectra were recorded at 300 or 400 MHz for proton on a Broker Mercury Plus 400 NMR Spectrometer equipped with a Broker 400 BBC) probe.

LCMS analyses were performed on a SHIMADZU LCMS consisting of an UFLC 20-AD and LCMS 2020 MS detector. The column used was a Shim-pack XR-ODS, 2.2 µm, 3.0×50 mm. A linear gradient was applied, starting at 95% A (A: 0.05%) TFA in water) and ending at 100% B (B; 0.05% TFA in MeCN) over 2.2 min with a total run time of 3.6 min. The column temperature was at 40° C. with the flow rate of 1.0 mL/min. The Diode Array Detector was scanned from 200-400 nm. The mass spectrometer was equipped with an electrospray ion source (ES) operated in a positive or negative mode.

HPLC analyses were performed on a SHIMADZU UFLC with two LC20 AD pump and a SPD-M20A Photodiiode Array Detector. The column used was an XBridge $C_{18}$, 3.5 µm, 4.6×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 ml, concentrated $H_2SO_4$) to visualize the compound. Flash chromatography was preformed using 40-63 µm (230-400 mesh) silica gel from Siticycle following analogous techniques to those disclosed in Still, W. C.; Kahn, M.; and Mitra, M. journal of Organic Chemistry, 1978, 43, 2923. Typical solvents used for flash chromatography or thin layer chromatography were mixtures of chloroform/methanol, dichloromethane/methanol, ethyl acetate/methanol and petroleum ether/ethyl acetate.

Preparative HPLC was performed on either a Waters Prep LC 4000 System using a Waters 2487 Diode Array or on a Waters LC Module 1 plus. The column used was SunFire Prep C18 OBD Column, 5 µm, 19×150 mm. Narrow gradients with acetonitrile/water, with the water containing either 0.1% trifluoroacetic acid or 0.1% $NH_4HCO_3$, were used to elute the compound at a flow rate of 20 mL/min and a total run time between 20-30 mm. Detector, 254 nm, 220 nm.

Chiral HPLC conditions: Column, Chiralpak IA, 5 µm, 20×150 mm; Mobile phase, Hex/EtOH or IPA; Detector, 254 nm, 220 nm.

Starting materials used were either available from commercial sources or prepared according to literature procedures and had experimental data in accordance with those reported.

The following abbreviations have been used:

ACN acetonitrile
AcOH acetic acid
aq. aqueous
9-BBN 9-Borabicyclo(3.3.1)nonane
BSA bovine serum albumin
Brettphos Pd
G3 [(2-Di-cyclohexylphosphino-3,6-dimethoxy-2',4',6'-triisopropyl-1,1'-biphenyl)-2-(2'-amino-1,1'-biphenyl)] palladium(II) methanesulfonate methanesulfonate
° C. degree Celsius
CAN Ceric ammonium nitrate
DAST diethylaminosulfur trifluoride
DCM dichloromethane
DIAD di-tert-butylazodicarboxylate
DIEA N,N-diisopropylethylamine
DMAP 4-(dimethylamino)pyridine
DMF N,N-dimethylformamide
DMSO dimethylsulfoxide
dppf 1,1'-bis(diphenylphosphino)ferrocene
DPP-Pd diphenylphosphine palladium
DTT dithiothreitoi
EDC N-p-dimethylaminopropyl)-N'-ethylcarbodiimide
EtOAc ethyl acetate
EtOH ethanol
g gram
h hour(s)
HATU N-[(Dimethylamino)-1H-1,2,3-triazolo-[4,5d]pyridin-1-ylmethylene]-N-methylmethanaminium hexafluorophosphate TV-oxide
HPLC high pressure liquid chromatography
IBX 2-iodoxybenzoic acid
iPr isopropyl
LCMS liquid chromatography and mass spectrometry
LiHMDS lithium bis(trimethylsilyl)amide
m-CPBA meta-chloroperoxybenzoic acid
M molar
MeOH methanol MS mass spectrometry
MTBE methyl tert-butyl ether
mmol millimole
mg milligram
min minutes
mL milliliter(s)
nM nanomolar
NMP N-methyl-2-pyrrolidone
N normal
NMR nuclear magnetic resonance
Pd/C or Pd—C palladium on carbon
PdCl₂(dppf) [1,1-bis(diphenylphosphine)ferrocene]dichloropalladium(II)
Pd(PPh₃)₄ tetrakis(triphenylphosphine)palladium(0)
PMB p-methoxybenzyl
POCl₃ phosphorus(V) oxychloride
psi pound per square inch
PYBOP benzotriazol-1-yl-oxytripyrrolidinophosphonium hexafluorophosphate
rt room temperature
sat. saturated
SM starting material
SFC Supercritical fluid chromatography
SOCl₂ thionyl chloride
TBAF tetra-n-butylammonium fluoride
tBu tert-butyl
TEA triethylamine
TFA trifluoroacetic acid
THF tetrahydrofuran
TLC thin layer chromatography
TMSCl Trimethylsilyl chloride
TBDPSCl tert-butyl(chloro)diphenylsilane
TBDPSO tert-butyldiphenylsilyl ether
TBAB Tetra-n-butylammonium bromide
Prep-TLC preparative TLC
μL microliter
wt weight General Synthetic Schemes Unless otherwise indicated, all variables are as previously defined.

LG is a suitable leaving group such as Cl or OCH₃.

Ar is

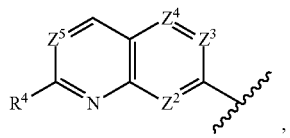

,

Scheme 1

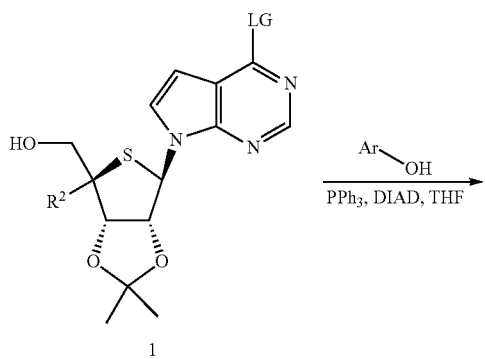

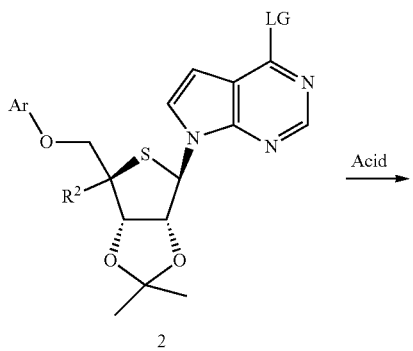

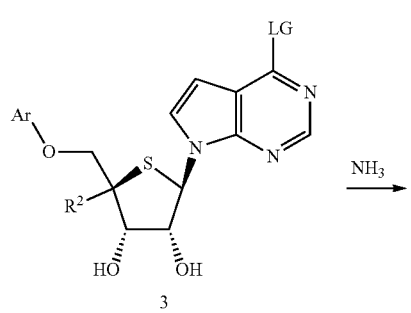

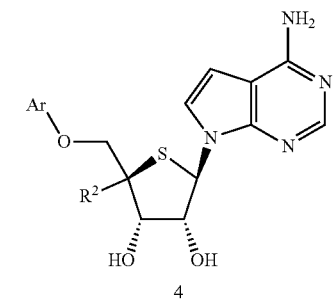

Compounds of formula 4 can be formed as illustrated in scheme 1. Compound 2 is generated from 1 via a Mitsunobu reaction and then subjected to suitable deprotection conditions to generate 3. Compound 4 is generated from 3 after displacement of a suitable leaving group.

Scheme 2

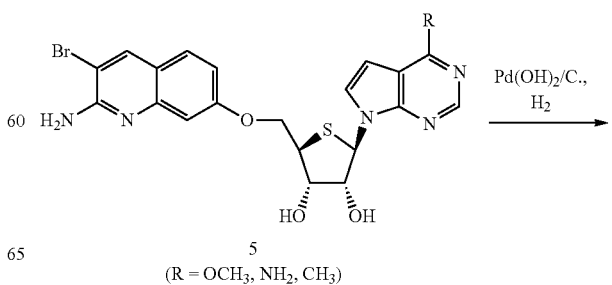

(R = OCH₃, NH₂, CH₃)

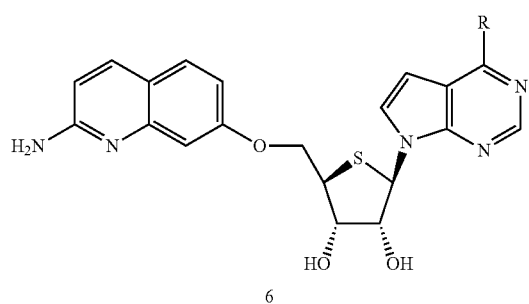

6

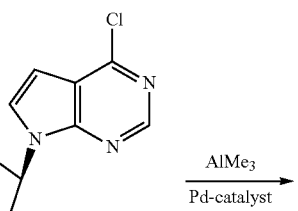

Scheme 4

7

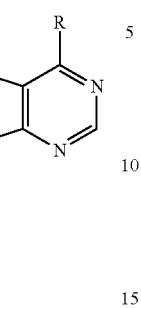

Compounds of formula 6 may be generated from 5 via hydrogenation.

Scheme 3

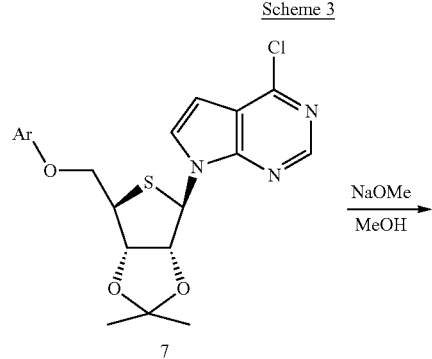

7

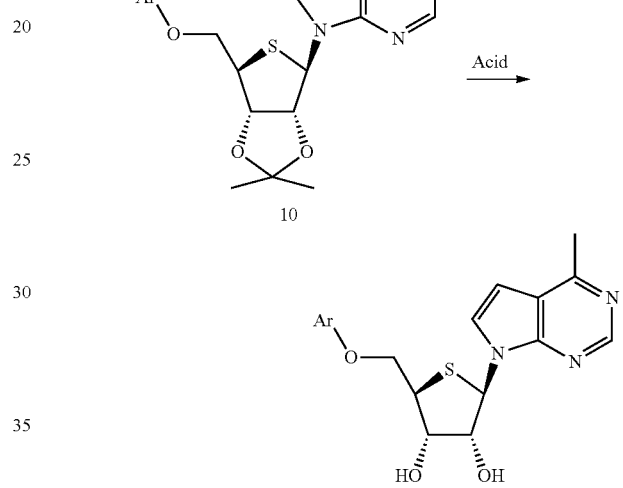

10

11

Compounds of formula 11 can be formed as illustrated in scheme 4. Compound 10 is generated from 7 via treatment with trimethylaluminum and a palladium catalyst. Compound 11 is generated from 10 via acid mediated deprotection.

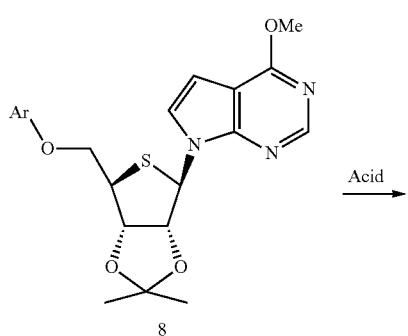

8

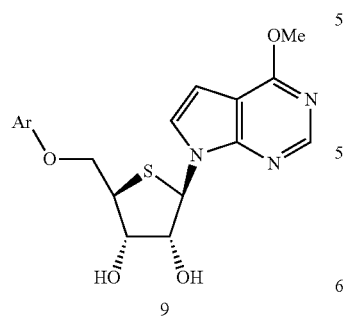

9

Compounds of formula 9 can be formed as illustrated in scheme 3. Compound 8 is generated from Compound 7 via chloride displacement. Acid mediated deprotection conditions afford Compound 9.

Scheme 5

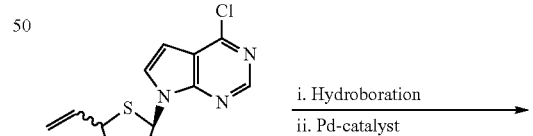

12

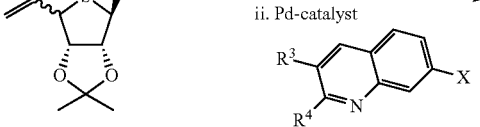

(X = Cl, Br)

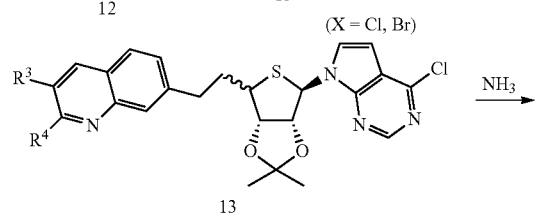

13

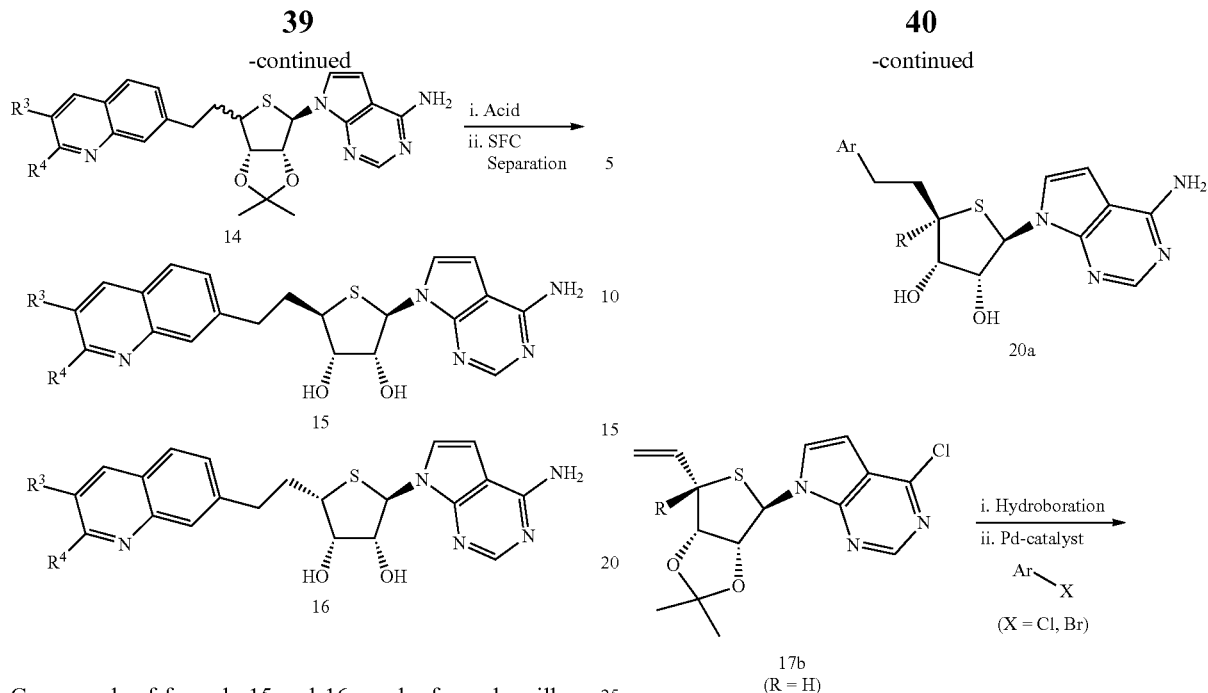

Compounds of formula 15 and 16 can be formed as illustrated in scheme 5. Compound 12 is transformed to an organoborane via hydroboration with a reagent such as 9-BBN. The resulting organoborane is utilized in a palladium catalyzed cross coupling reaction to generate compounds of formula 13. Aminolysis and acid mediated acetonide deprotection was followed by SFC separation to afford two stereoisomers with formula 15 and 16.

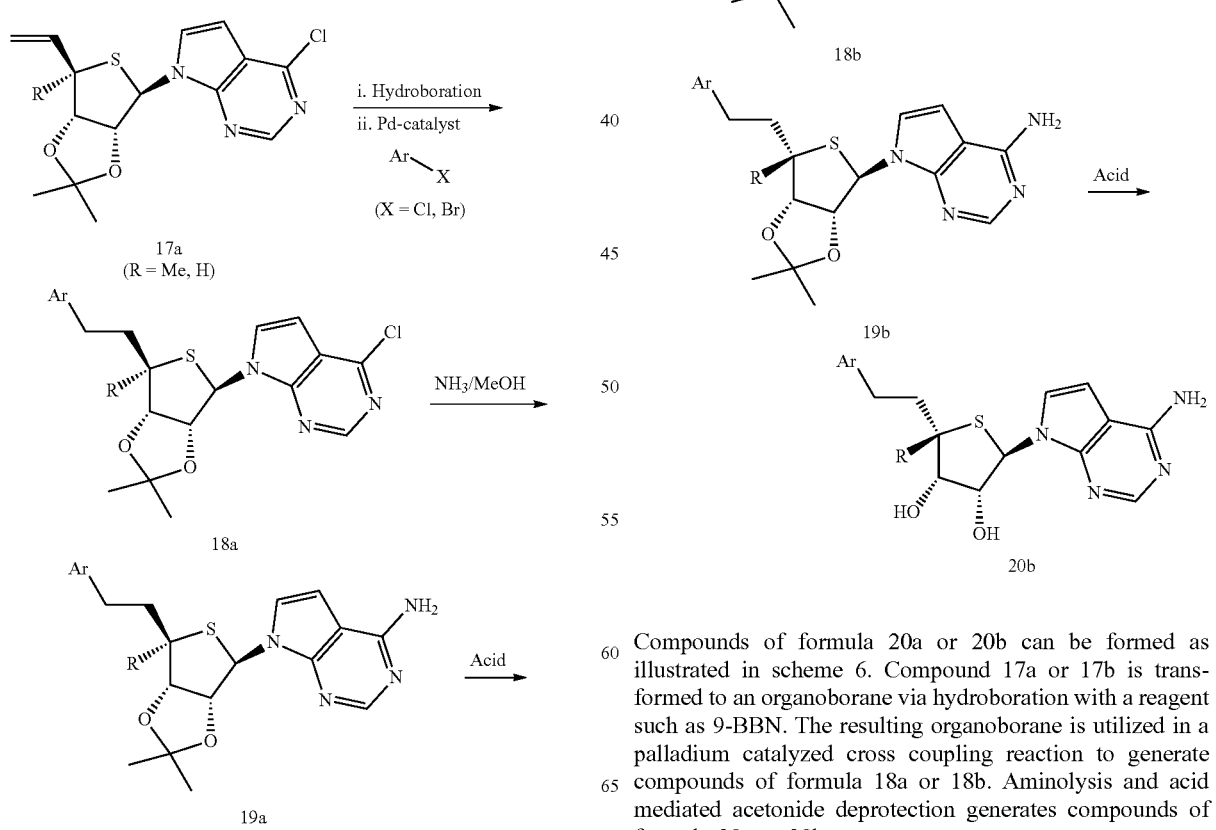

Compounds of formula 20a or 20b can be formed as illustrated in scheme 6. Compound 17a or 17b is transformed to an organoborane via hydroboration with a reagent such as 9-BBN. The resulting organoborane is utilized in a palladium catalyzed cross coupling reaction to generate compounds of formula 18a or 18b. Aminolysis and acid mediated acetonide deprotection generates compounds of formula 20a or 20b.

Scheme 7

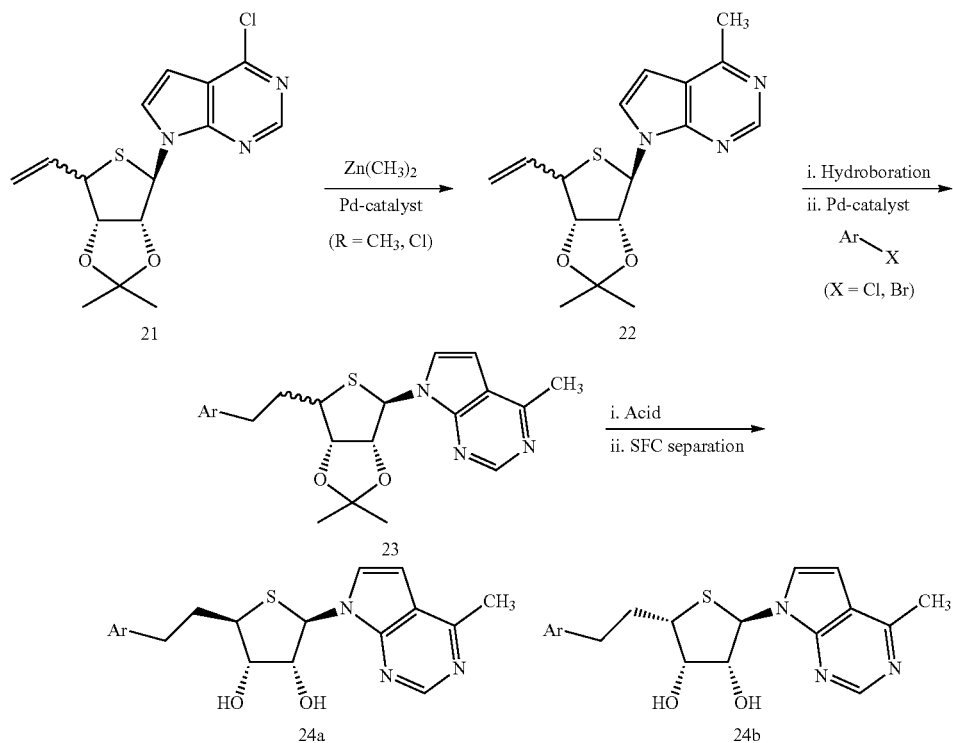

Compounds of formula 24a and 24 h can be formed as illustrated in scheme 7. Compound 22, generated from 21 via treatment with dimethylzinc and a palladium catalyst, is transformed to an organoborane via hydroboration with a reagent such as 9-BBN. The resulting organoborane is utilized in a palladium catalyzed cross coupling reaction to generate a compound of formula 23. Acid mediated acetonide deprotection followed by SFC separation generates compounds of formula 24a and 24b.

Scheme 8

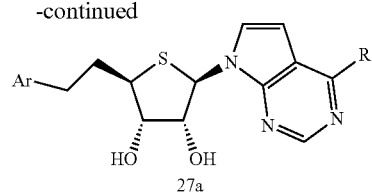

-continued

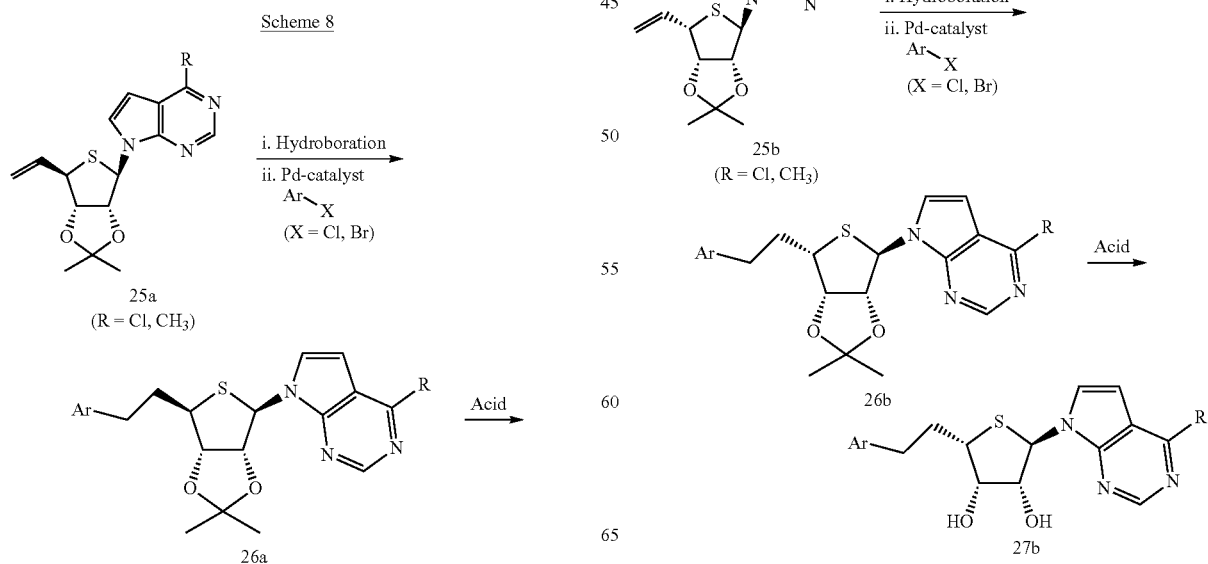

Compounds of formula 27a or 27b can be formed as illustrated in Scheme 8. Compound 25a or b is transformed to an organoborane via hydroboration with a reagent such as 9-BBN. The resulting organoborane is utilized in a palladium catalyzed cross coupling reaction to generate compounds of formula 26a or 26b. Acid mediated acetonide deprotection generates compounds of formula 27a or 27b.

Scheme 9

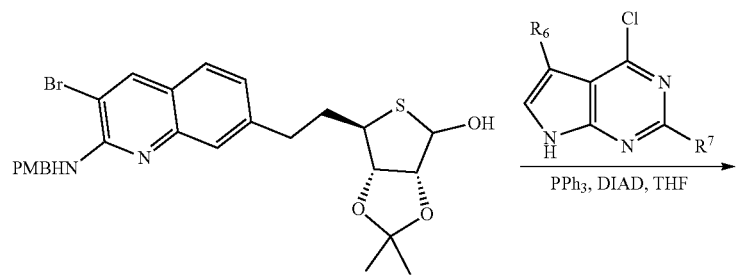

28

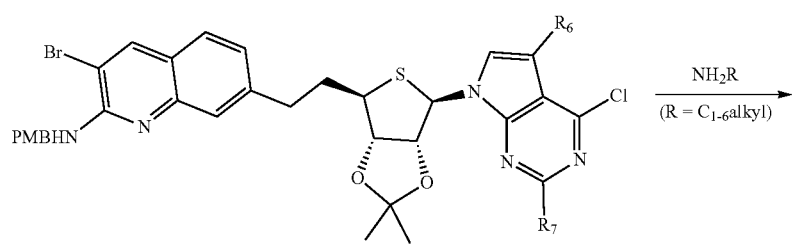

29

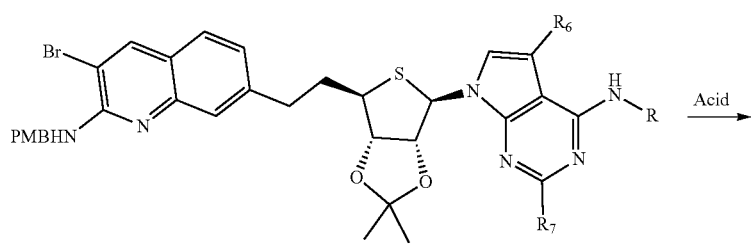

30

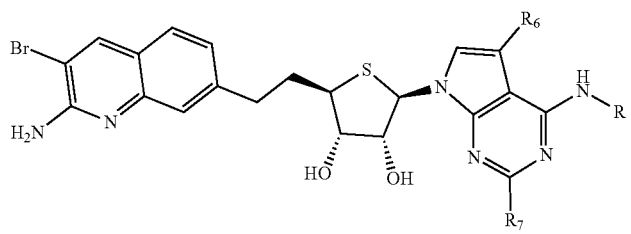

31

Compounds of formula 31 can be formed as illustrated in scheme 9. Compound 30 is generated from 28 via a Mitsunobu reaction followed by nucleophilic aromatic substitution. Acid mediated acetal deprotection affords Compound 31.

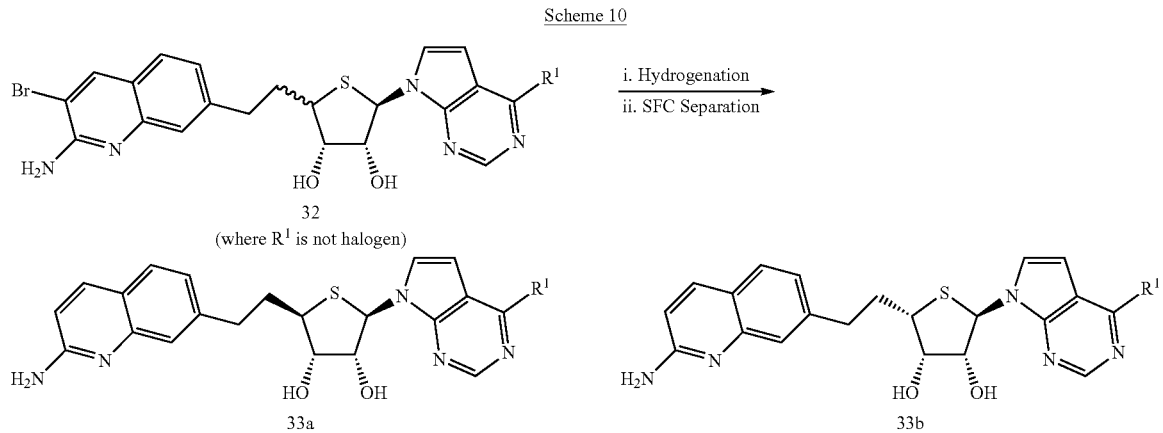

Compounds of formula 33a and 33b may be generated from 32 via hydrogenation and subsequent SFC separation.

INTERMEDIATES

Intermediate 1: 2-amino-3-bromoquinolin-7-ol

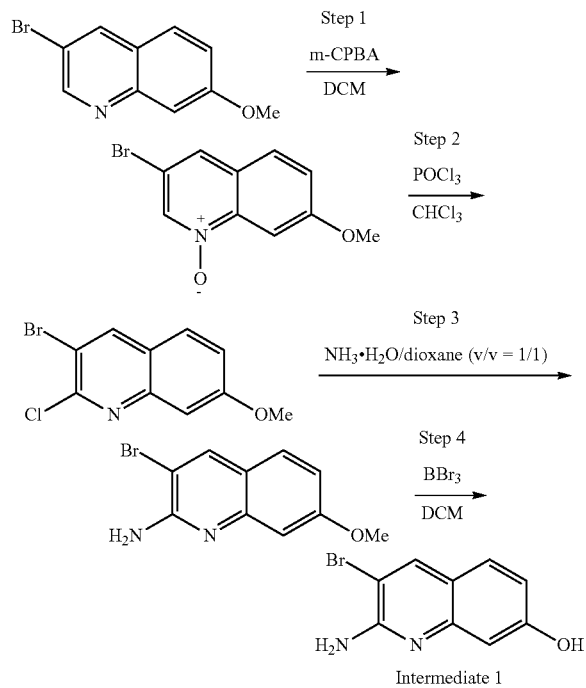

Step 1: To a solution of 3-bromo-7-methoxyquinoline (1.0 g, 4.2 mmol) in CH$_2$Cl$_2$ (10 mL) was added 3-chlorobenzoyl peroxide (870 mg, 5.06 mmol) portion wise at 0° C. The resulting mixture was stirred at 25° C. for 1.5 h. The mixture was poured into a saturated aqueous solution of Na$_2$S$_2$O$_3$ (50 mL). The mixture was extracted with DCM (50 mL×2). The organic phase was washed with saturated aqueous NaHCO$_3$ (50 mL), brine (50 mL), dried over anhydrous Na$_2$SO$_4$ and filtered. After partial concentration, a solid precipitated and was filtered to obtain 3-bromo-7-methoxyquinoline 1-oxide. MS: 254, 256 (M+1). $^1$H NMR (400 MHz, Chloroform-d) δ 8.67 (s, 1H), 8.02 (s, 1H), 7.88 (s, 1H), 7.71 (d, J=9.0 Hz, 1H), 7.33 (dd, J=9.1, 2.2 Hz, 1H), 4.03 (s, 3H).

Step 2: To a solution of 3-bromo-7-methoxyquinoline 1-oxide (940 mg, 3.70 mmol) in CHCl$_3$ (20 mL) was added phosphoryl trichloride (3 mL, 32 mmol) at 25° C. After stirring at 80° C. for 3 h, tire mixture was concentrated under reduced pressure. The residue was poured into 30 mL of ice water, and then the mixture was neutralized by adding ammonium hydroxide. After extraction by DCM (60 mL×3), the organic layer was washed with water (50 mL×2) and brine (50 mL), dried over anhydrous Na$_2$SO$_4$, and then filtered. The filtrate was concentrated under reduced pressure to give 3-bromo-2-chloro-7-methoxyquinoline, which was used directly in step 3. MS: 272, 274 (M+1). $^1$H NMR (300 MHz, DMSO-d$_6$) δ 8.30 (s, 1H), 7.61 (d, J=9.0 Hz, 1H), 7.30 (d, J=2.5 Hz, 1H), 7.20 (dd, J=9.0, 2.5 Hz, 1H), 3.91 (s, 3H).

Step 3: To a sealed tube (100 mL) was added 3-bromo-2-chloro-7-methoxy quinoline (990 mg, 3.7 mmol), 1,4-dioxane (10 mL) and ammonium hydroxide (10 mL, 260 mmol). The tube was sealed tightly, and the resulting mixture was heated at 120° C. for 20 h. The mixture was concentrated under reduced pressure. The residue was extracted with EtOAc (60 mL×3), and then washed with water (50 mL×2) and brine (50 mL) successively. The combined organic phase was dried over anhydrous Na$_2$SO$_4$, filtered, and the filtrate was concentrated under reduced pressure. The residue was purified by column chromatography on silica (eluting with EtOAc/petroleum ether) to give 3-bromo-7-methoxyquinolin-2-amine as a solid. MS: 253, 255 (M+1). $^1$H NMR (300 MHz, DMSO-d$_6$) δ 8.08 (s, 1H), 7.47 (d, J=8.9 Hz, 1H), 7.04 (d, J=2.5 Hz, 1H), 6.95 (dd, J=8.9, 2.5 Hz, 1H), 5.22 (s, 2H), 3.92 (s, 3H).

Step 4: To a solution of 3-bromo-7-methoxyquinolin-2-amine (530 mg, 2.09 mmol) in DCM (6 mL) under an argon atmosphere was added tribromoborane (10.5 g, 41.9 mmol) slowly at 0° C., and the mixture was stirred at room temperature for 4 h. The reaction was quenched with MeOH slowly at 0° C. and stirred at 25° C. for 15 min. The pH of the mixture was adjusted to 8 with aqueous NaHCO₃. The resulting precipitate was collected by filtration and washed with water to give 2-amino-3-bromoquinolin-7-ol as a solid. MS: 239, 241 (M+1). ¹H NMR (300 MHz, DMSO-d₆) δ 9.83 (s, 1H), 8.16 (s, 1H), 7.45 (d, J=8.6 Hz, 1H), 6.80-6.69 (m, 2H), 6.45 (s, 2H).

Intermediate 2: 2-amino-3-chloroquinolin-7-ol

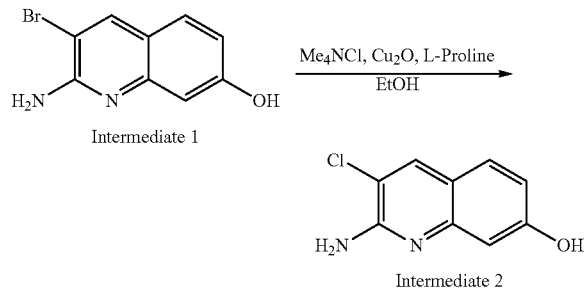

To a stirred solution of 2-amino-3-bromoquinolin-7-ol (1 g, 4.2 mmol) in EtOH (20 mL) was added cuprous oxide (0.90 g, 6.27 mmol), tetramethylammonium chloride (3.67 g, 33.5 mmol) and (S)-pyrrolidine-2-carboxylic acid (1.45 g, 12.6 mmol) at ambient temperature. The mixture was stirred at 110° C. for 8 h. The resulting mixture was concentrated under reduced pressure and the residue was purified by column chromatography on silica (0-10% MeOH/DCM) to give 2-amino-3-chloroquinolin-7-ol as a solid. MS: 195 (M+1). ¹H NMR (300 MHz, DMSO-d₆) δ 9.80 (s, 1H), 8.01 (s, 1H), 7.48 (d, J=8.6 Hz, 1H), 6.83-6.71 (m, 2H), 6.54 (s, 2H).

Intermediate 3: 2-((cyclopropylmethyl)amino)quinolin-7-ol—Method A

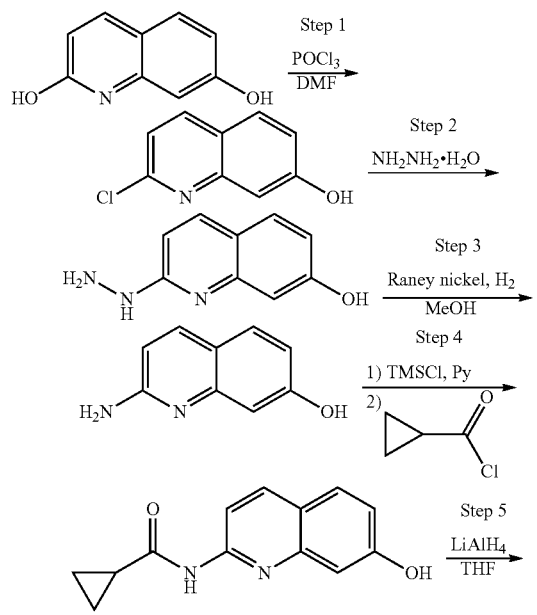

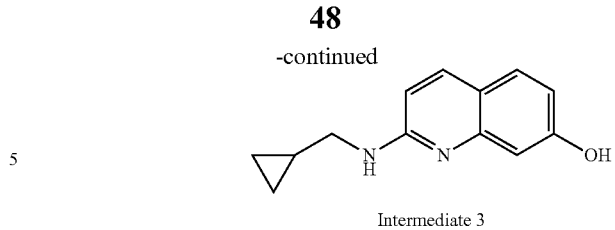

Intermediate 3

Step 1: To a suspension of quinoline-2,7-diol (5 g, 30 mmol) in DMF (10 mL) was added phosphoryl trichloride (16.1 mL, 177 mmol) at 25° C. The mixture was heated at 70° C. for 1 h. The solvent was removed under reduced pressure. The resulting residue was poured slowly into water (100 mL) at 0° C. The pH was adjusted to 8 with saturated aqueous Na₂CO₃, The mixture was extracted with EtOAc (50 mL×3). The combined organic layers were washed with brine (50 mL), dried over anhydrous sodium sulfate and filtered. The filtrate was concentrated under reduced pressure to afford 2-chloroquinolin-7-ol. MS: 180 (M+1). ¹H NMR (400 MHz, DMSO-d₆) δ 10.49 (s, 1H), 8.27 (d, J=8.4 Hz, 1H), 7.87 (d, J=8.8 Hz, 1H), 7.31 (d, J=8.4 Hz, 1H), 7.28-7.11 (m, 2H).

Step 2: A solution of 2-chloroquinolin-7-oi (2 g, 10 mmol) in hydrazine hydrate (20 mL, 11 mmol) was heated at 80° C. for 5 h. The mixture was concentrated under reduced pressure, and the residue was purified by reverse-phase HPLC (0-100% acetonitrile/water) to give 2-hydrazinylquinolin-7-ol, MS: 176 (M+1). ¹H NMR (400 MHz, DMSO-d₆) δ 9.70 (br s, 1H), 7.91 (brs, 1H), 7.73 (d, J=8.8 Hz, 1H), 7.45 (d, J=8.6 Hz, 1H), 6.87 (d, J=2.3 Hz, 1H), 6.72 (dd, J=8.6, 2.4 Hz, 1H), 6.63 (d, J=8.8 Hz, 1H), 3.41 (s, 2H).

Step 3: To a solution of 2-hydrazinylquinolin-7-ol (2 g, 11.4 mmol) in MeOH (20 mL) was added Raney nickel (1 g; 50% slurry in water) under an argon atmosphere. The flask was evacuated and flushed three times with hydrogen. The mixture was stirred at 25° C. for 40 h under an atmosphere of hydrogen. The reaction mixture was filtered, and the filtrate was concentrated under reduced pressure to afford 2-aminoquinolin-7-ol. MS: 161 (M+1). ¹H NMR (400 MHz, DMSO-d₆) δ 9.64 (br s, 1H), 7.72 (d, J=8.7 Hz, 1H), 7.43 (d, J=8.6 Hz, 1H), 6.76 (d, J=2.3 Hz, 1H), 6.69 (dd, J=8.6, 2.4 Hz, 1H), 6.51 (d, J=8.7 Hz, 1H), 6.27 is, 2H).

Step 4: To a stirred suspension of 2-aminoquinolin-7-ol (400 mg, 2.50 mmol) in dry pyridine (7 mL) was added trimethylsilyl chloride (0.64 mL, 5.0 mmol) dropwise at 0° C. for over 5 min. The resulting mixture was stirred for 0.5 h at 0° C. Cyclopropane carbonyl chloride (783 mg, 7.49 mmol) was added at 0° C. via a syringe. The resulting mixture was warmed to 20° C. and stirred for additional 16 h. The reaction was quenched with MeOH (2 mL) at 0° C., and then NH₃·H₂O (2 mL, 25%-28% w/w, 27 mmol) was added dropwise at 0° C. The mixture was stirred at 25° C. for 3 h. The reaction mixture was concentrated under reduced pressure and the residue was re-dissolved in EtOAc (20 mL). The mixture was filtered, and the filtrate was concentrated under reduced pressure. The residue was purified by column chromatography on silica (0-50% EtOAc/petroleum ether) to afford N-(7-hydroxyquinolin-2-yl)cyclopropanecarboxamide. MS: 229 (M+1). ¹H NMR (300 MHz, DMSO-d₆) δ 10.97 (s, 1H), 10.07 (s, 1H), 8.16 (d, J=9.0 Hz, 1H), 8.07 (d, J=9.0 Hz, 1H), 7.72 (d, J=8.7 Hz, 1H), 7.10-6.99 (m, 2H), 2.15-1.96 (m, 1H), 0.95-0.79 (m, 4H).

Step 5: To a solution of N-(7-hydroxyquinolin-2-yl)cyclopropanecarboxamide (300 mg, 1.31 mmol) in THF (5 mL) was added LiAlH₄ (249 mg, 6.57 mmol) in several portions at 0° C. under an atmosphere of argon. The reaction mixture was warmed to 70° C. and stirred for 3 h under an atmosphere of argon. The reaction mixture was quenched with water (20 mL) at 0° C. and extracted with EtOAc (50 mL×5). The combined organic layers were washed with brine (100 mL), dried over anhydrous $Na_2SO_4$, and filtered. The filtrate was concentrated under reduced pressure. The residue was purified by column chromatography on silica (0-5% MeOH/DCM) to afford 2-((cyclopropylmethyl) amino)quinolin-7-ol. MS: 215 (M+1). $^1$H NMR (300 MHz, DMSO-$d_6$) δ 9.60 (s, 1H), 7.68 (d, J=8.7 Hz, 1H), 7.41 (d, J=8.7 Hz, 1H), 7.03-6.94 (m, 1H), 6.79 (d, J=2.4 Hz, 1H), 6.67 (dd, J=8.4, 2.4 Hz, 1H), 6.56 (d, J=8.7 Hz, 1H), 3.24 (t, J=6.8, 2H), 1.28-1.02 (m, 1H), 0.53-0.36 (m, 2H), 0.35-0.20 (m, 2H).

Intermediate 3: 2-((cyclopropylmethyl)amino)quinolin-7-ol—Method B

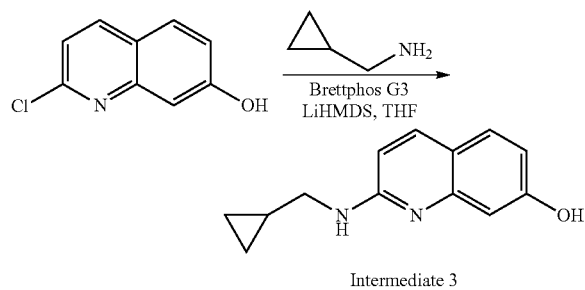

Intermediate 3

To a solution of LiHMDS (1 M in THF, 55.7 mL, 55.7 mmol) was added 2-chloroquinolin-7-ol (1 g, 5.57 mmol), Brettphos Pd G3 (0.505 g, 0.557 mmol) and cyclopropylmethanamine (0.475 g, 6.68 mmol) at room temperature. The mixture was stirred at 80° C. for 16 h. The mixture was concentrated under reduced pressure and the residue was purified by column chromatography on silica (0-10% MeOH/DCM) followed by reverse-phase HPLC (0-5014 acetonitrile/water) to afford 2-((cyclopropylmethyl)amino) quinolin-7-ol. The analytical data were in agreement with material from method A.

Intermediate 4: 2-chloro-3-fluoroquinolin-7-ol

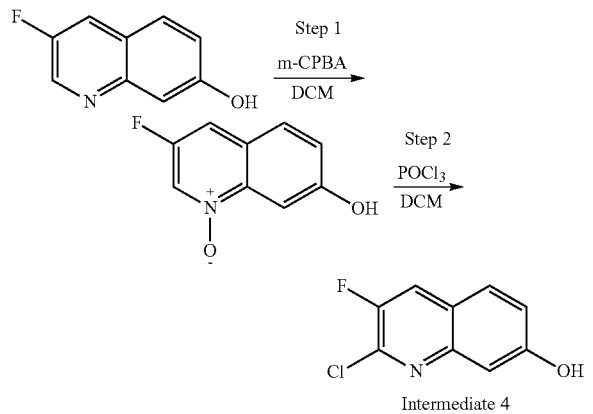

Intermediate 4

Step 1: 3-Fluoroquinolin-7-ol (730 mg, 4.5 mmol) was dissolved in DCM (50 mL), then 3-chlorobenzoyl peroxide (1.33 g, 5.4 mmol) was added in one portion. The reaction mixture was stirred at ambient temperature for 2 h. The mixture was quenched by the addition of 50 mL of saturated aq. $NaHCO_3$. The resulting mixture was extracted with EtOAc (200 mL×3), and the combined organic layers were washed with saturated aqueous $NaHCO_3$ (40 mL) and brine (40 mL), The organic layer was dried over $Na_2SO_4$, filtered, and the filtrate was concentrated under reduced pressure to give crude 3-fluoro-7-hydroxyquinoline 1-oxide. MS: 180 (M+1).

Step 2: To a stirred solution of 3-fluoro-7-hydroxyquinoline 1-oxide (LOB g, 1.81 mmol) in DMF (10 mL) was added phosphoryl trichloride (1.86 g, 6.75 mmol). The reaction mixture was stirred at 80° C. for 2 h. The mixture was quenched by the addition of 80 mL of saturated aq. $NaHSO_3$. The mixture was extracted with EtOAc (150 mL×3), and the combined organic layers were washed with saturated aq, $NaHCO_3$ (50 mL) and brine (50 mL). The organic layer was dried over $Na_2SO_4$, filtered, and the filtrate was concentrated under reduced pressure. The residue was purified by prep-TLC with petroleum ether/EtOAc (v:v, 1/1) to give 2-chloro-3-fluoroquinolin-7-ol. MS: 198 (M+1), TT NMR (400 MHz, DMSO-$d_6$): δ 10.46 (s, 1H), 8.36 (d, J=9.2 Hz, 1H), 7.88 (d, J=8.8 Hz, 1H), 7.28 (dd, J=8.8, 2.4 Hz, 1H), 7.22 (d, J=2.4 Hz, 1H).

Intermediate 5: ((3aS,4R,6R,6R)-6-(4-chloro-7H-pyrrolo[2,3-d]pyrimidin-7-yl)-2,2-dimethyltetrahydrothieno[3,4-d][1.3]dioxol-4-yl)methanol—Method A

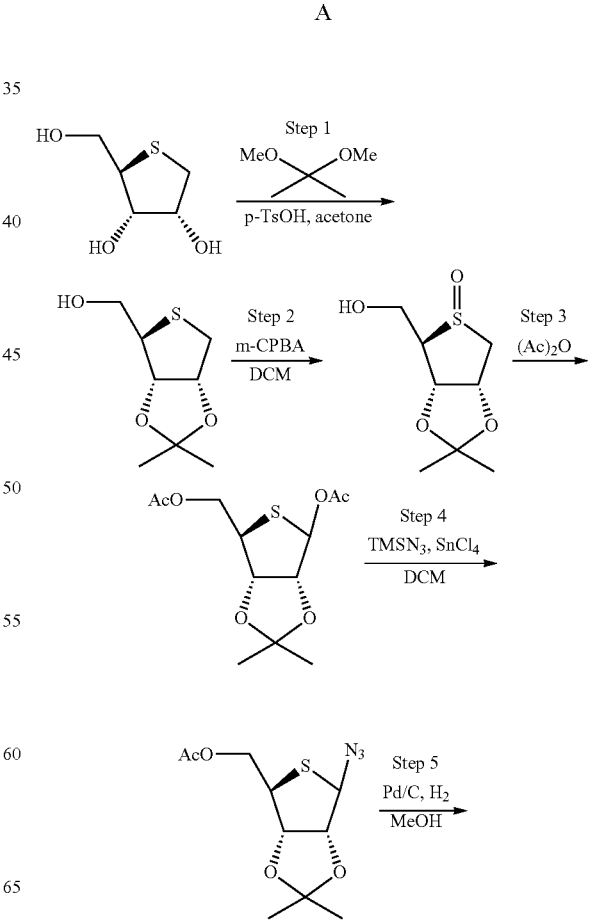

-continued

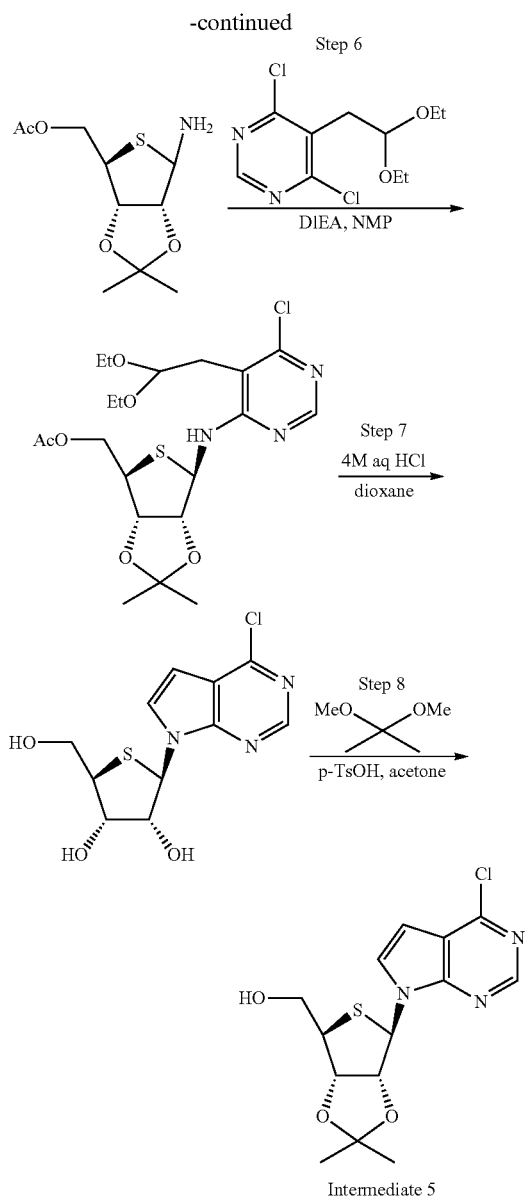

Intermediate 5

Step 1: To a solution of (2R,3S,4R)-2-(hydroxymethyl)tetrahydrothiophene-3,4-diol (19 g, 127 mmol) and 4-methylbenzenesulfonic acid (2.18 g, 12.7 mmol) in acetone (190 mL) was added 2,2-dimethoxypropane (52.7 g, 506 mmol) at 25° C. The mixture was stirred for 2 h at 25° C. The reaction mixture was quenched with saturated aq. NaHCO$_3$ (500 mL) and extracted with EtOAc (500 mL×3). The combined organic layers were dried over anhydrous Na$_2$SO$_4$, filtered, and the filtrate was concentrated under reduced pressure. The residue was purified by column chromatography on silica (0-100% EtOAc/petroleum ether) to give ((3aS,4R,6aR)-2,2-dimethyltetrahydrothieno[3,4-d][1.3]dioxol-4-yl)methanol. $^1$H NMR (300 MHz, DMSO-d$_6$) δ 4.99-4.97 (m, 1H), 4.86-4.80 (m, 1H), 4.72-4.70 (m, 1H), 3.53-3.21 (m, 2H), 3.17-2.93 (m, 2H), 2.72-2.66 (m, 1H), 1.35 (s, 3H), 1.21 (s, 3H).

Step 2: To a solution of ((3aS,4R,6aR)-2,2-dimethyltetrahydrothieno[3,4-d][1,3]dioxol-4-yl)methanol (14 g, 73.6 mmol) in DCM (140 mL) was added 3-chlorobenzoyl peroxide (20.0 g, 81 mmol) at −70° C. The mixture was stirred for 1 h at −70° C. The mixture was quenched with saturated aqueous sodium sulfite solution (300 mL), then extracted with EtOAc (50 mL×3). The organic phase was dried over anhydrous Na$_2$SO$_4$ and filtered. The filtrate was concentrated under reduced pressure. The residue was purified by column chromatography on silica (0-100% EtOAc/petroleum ether) to give (3aS,4R,5R,6aR)-4-(hydroxymethyl)-2,2-dimethyltetrahydrothieno[3,4-d][1,3]dioxole 5-oxide, $^1$H NMR (300 MHz, DMSO-d$_6$) δ 5.17-5.01 (m, 2H), 4.80-4.74 (m, 1H), 3.86-3.66 (m, 2H), 3.30-3.10 (m, 3H), 1.36 (s, 3H), 1.22 (s, 3H).

Step 3; A mixture of (3aS,4R,5R,6aR)-4-(hydroxymethyl)-2,2-dimethyltetrahydrothieno[3,4-d][1,3]dioxole 5-oxide (7.8 g, 37.8 mmol) in acetic anhydride (100 mL, 37.8 mmol) was stirred for 2 h at 110° C. The reaction mixture was diluted with EtOAc (500 mL) and washed with saturated aqueous NaHCO$_3$ (200 mL×3). The organic layer was dried over anhydrous sodium sulfate and filtered. The filtrate was concentrated under reduced pressure. The residue was purified by column chromatography on silica (0-20% of EtOAc/petroleum ether) to give ((3aS,4R,6aR)-6-acetoxy-2,2-dimethyltetrahydrothieno[3,4-d][1,3]dioxol-4-yl)methyl acetate. $^1$H NMR (300 MHz, DMSO-d$_6$) δ 5.80 (s, 1H), 4.90 (s, 2H), 4.31-3.89 (m, 2H), 3.79-3.42 (m, 1H), 2.16-1.82 (m, 6H), 1.40 (d, J=19.2 Hz, 3H), 1.27-1.16 On 3H).

Step 4: To a solution of ((3aS,4R,6aR)-6-acetoxy-2,2-dimethyltetrahydrothieno[3,4-d][1,3]dioxol-4-yl)methyl acetate (6.5 g, 22.4 mmol) and azidotrimethylsilane (7.74 g, 67.2 mmol) in DCM (100 mL) was added perchlorostannane (1.46 g, 5.60 mmol) at 0° C. The mixture was stirred for 0.25 h at 0° C. The reaction mixture was quenched with saturated aq. NaHCO$_3$ solution (100 mL) and extracted with EtOAc (150 mL×3). The combined organic layers were dried over anhydrous Na$_2$SO$_4$, and filtered. The filtrate was concentrated under reduced pressure. The residue was purified by column chromatography on silica (0-20% EtOAc/petroleum ether) to give ((3aS,4R,6aR)-6-azido-2,2-dimethyltetrahydrothieno[3,4-d][1,3]dioxol-4-yl)methyl acetate. $^1$H NMR (300 MHz, DMSO-d$_6$) δ 5.51 (s, 1H), 4.85 (d, J=5.40 Hz, 1H), 4.62 (d, J=5.40 Hz, 1H), 4.13-3.98 (m, 2H), 3.60-3.55 (m, 1H), 2.02 (s, 3H), 1.36 (s, 3H), 1.21 (s, 3H).

Step 5: To a solution of ((3aS,4R,6aR)-6-azido-2,2-dimethyltetrahydrothieno[3,4-d][1,3]dioxol-4-yl)methyl acetate (1.2 g, 4.39 mmol) in MeOH (10 mL) was added 10% palladium on carbon (150 mg, 0.42 mmol) at 25° C. The resulting mixture was stirred for 1 h at 25° C. under 1 atmosphere of hydrogen. The reaction was filtered, and the filtrate was concentrated under reduced pressure. The residue was purified by column chromatography on silica (0-20% of EtOAc/petroleum ether) to give ((3aS,4R,6aR)-6-amino-2,2-dimethyltetrahydrothieno[3,4-d][1,3]dioxol-4-yl)methyl acetate. (H NMR. (300 MHz, DMSO-d$_6$) δ 5.03-4.69 (m, 1H), 4.67-4.47 (m, 2H), 4.29-3.82 (m, 2H), 3.49-3.12 (m, 1H), 2.23 (br s, 2H), 2.01-1.99 (m, 3H), 1.41-1.35 (m, 3H), 1.24-1.16 (m, 3H).

Step 6: To a solution of ((3aS,4R,6aR)-6-amino-2,2-dimethyltetrahydrothieno[3,4-d][1,3]dioxol-4-yl)methyl acetate (330 mg, 1.33 mmol) and 4,6-dichloro-5-(2,2-diethoxyethyl)pyrimidine (389 mg, 1.47 mmol) in NMP (3 mL) was added N-ethyl-N-isopropylpropan-2-amine (354 mg, 2.67 mmol) at 25° C. The mixture was stirred for 16 h at 100° C. The reaction mixture was cooled to 25° C. The mixture was diluted with EtOAc (100 mL) and washed with water (50 mL×3). The combined organic layers were dried over anhydrous Na$_2$SO$_4$ and filtered. The filtrate was concentrated under reduced pressure. The residue was purified by column chromatography on silica (0-10% of EtOAc/petroleum ether) to give ((3aS,4R,6R,6aR)-6-((6-chloro-5-(2,2-diethoxyethyl)pyrimidin-4yl)amino)-2,2-dimethyltetrahydrothieno[3,4-d][1,3]dioxol-4-yl)methyl acetate. MS: 476 (M+1).

Step 7: To a solution of ((3aS,4R,6R,6aR)-6-((6-chloro-5-(2,2-diethoxyethyl)pyrimidin-4-yl)amino)-2,2-dimethyl-tetrahydrothieno[3,4-d][1,3]dioxol-4-yl)methyl acetate (300 mg, 0.630 mmol) in dioxane (3 mL) was added hydrogen chloride (4 M in water, 0.6 mL, 2.4 mmol) at 50° C. The mixture was stirred for 2 h at 50° C. The reaction mixture was cooled to room temperature, and quenched with saturated aq. NaHCO$_3$ solution (10 mL). The mixture was concentrated under reduced pressure. The residue was purified by reverse-phase HPLC (0-30% acetonitrile/water with 5 mM aq. ammonium bicarbonate) to give (2R,3R,4S,5R)-2-(4-chloro-7H-pyrrolo[2,3-d]pyrimidin-7-yl)-5-(hydroxymethyl)tetrahydrothiophene-3,4-diol. MS: 302 (M+1). $^1$H NMR (300 MHz, DMSO-d$_6$) δ 8.67 (s, 1H), 8.11 (d, J=3.9 Hz, 1H), 6.76 (d, J=3.6 Hz, 1H), 6.22 (d, J=6.9 Hz, 1H), 5.51 (br s, 1H), 5.41 (hr s, 1H), 5.22 (br s, 1H), 4.51 (dd, J=6.9, 3.3 Hz, 1H), 4.18 (t, J=3.0 Hz, 1H), 3.80-3.74 (m, 1H), 3.65-3.60 (m, 1H), 3.30 (s, 1H).

Step 8: A solution of (2R,3R,4S,5R)-2-(4-chloro-7H-pyrrolo[2,3-d]pyrimidin-7-yl)-5-(hydroxymethyl)tetrahydrothiophene-3,4-diol (500 mg, 1.66 mmol) in acetone (8 mL) was treated with 4-methylbenzenesulfonic acid (31.4 rag, 0.165 mmol) and 2,2-dimethoxypropane (1.73 g, 16.6 mmol). The reaction mixture was stirred for 0.1 h at room temperature and then neutralized with NaHCO$_3$ (0.222 g). The mixture was diluted with water (30 mL) and extracted with EtOAc (30 mL×3). The organic layers were combined and washed with brine, dried over anhydrous sodium sulfate, and filtered. The filtrate was concentrated under reduced pressure, and the residue was purified by column chromatography on silica (0-30% EtOAc/petroleum ether) to give ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol. MS: 342 (M+1). $^1$H NMR (400 MHz, DMSO-d$_6$) δ 8.71 (s, 1H), 8.11 (d, J=3.8 Hz, 1H), 6.79 (d, J=3.7 Hz, 1H), 6.37 (d, 3.0 Hz, 1H), 5.41-5.33 (m, 1H), 5.28 (dd, J=5.5, 3.0 Hz, 1H), 5.01 (dd, J=5.6, 1.6 Hz, 1H), 3.77-3.54 (m, 3H), 1.56 (s, 3H), 1.30 (s, 3H).

Intermediate 5: ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol—Method B

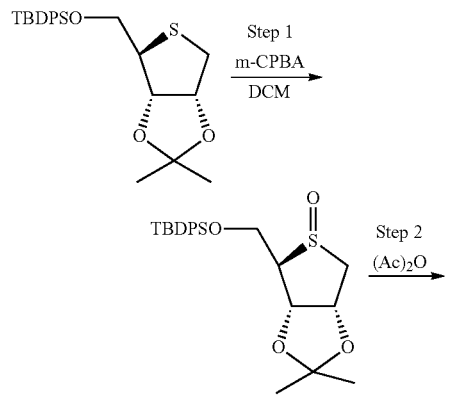

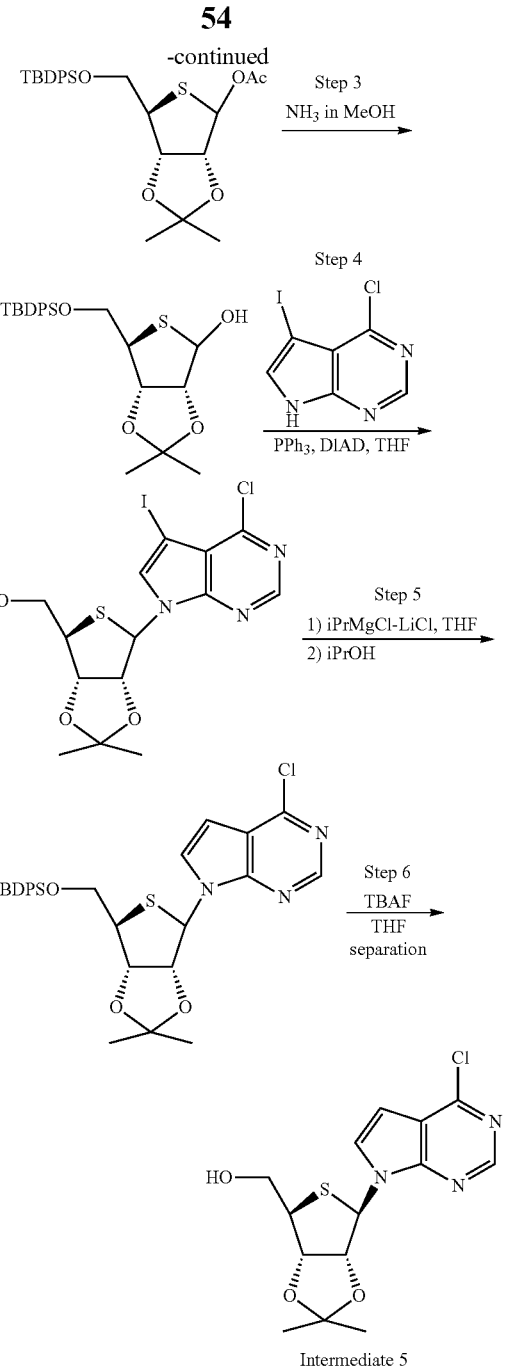

Step 1: To a solution of tert-butyl(((3aS,4R,6aR)-2,2-dimethyltetrahydrothieno[3,4-d][1,3]dioxol-4-yl)methoxy)diphenylsilane (12.8 g, 29.9 mmol) in DCM (100 mL) was added m CPBA (8.10 g, 32.8 mmol) at −70° C. and the mixture was stirred at −70° C. for 2 h. The reaction mixture was quenched with saturated sodium sulfite solution (130 mL). The resulting mixture was extracted with DCM (200 mL×3). The combined organic layers were washed with brine (100 mL) and dried over anhydrous sodium sulfate. After filtration, the filtrate was concentrated under reduced pressure. The residue was purified by column chromatography on silica (1-40% ethyl acetate/petroleum ether) to afford (3aS,4R,6aR)-4-(((tert-butyldiphenylsilyl)oxy)methyl)-2,2-dimethyltetrahydrothieno[3,4-d][1,3]dioxole 5-oxide. MS: 445 (M+1), $^1$H NMR (400 MHz, DMSO-d$_6$)

δ 7.70-7.58 (m, 4H), 7.51-7.41 (m, 6H), 5.15-5.11 (m, 1H), 4.93-4.77 (m, 1H), 4.06-3.76 (m, 2H), 3.62-3.44 (m, 2H), 3.40-3.18 (m, 1H), 1.41-1.39 (m, 3H), 1.26-1.24 (m, 3H), 1.02-0.99 (m, 9H).

Step 2: To (3aS,4R,6aR)-4-(((tert-butyldiphenylsilyl)oxy) methyl)-2,2-dimethyltetrahydrothieno[3,4-i][1,3]dioxole 5-oxide (10.8 g, 24.3 mmol) was added acetic anhydride (110 mL, 24.3 mmol) at ambient temperature. The mixture was warmed to 110° C. and stirred for 3 h. The reaction mixture was cooled to room temperature and concentrated under reduced pressure. The residue was diluted with EtOAc (600 mL), washed with saturated aqueous NaHCO$_3$, (150 mL×3), and the organic layer was dried over anhydrous Na$_2$SO$_4$. After filtration, the filtrate was concentrated under reduced pressure to give (3aR,6R,6aS)-6-(((tert-butyldiphenylsilyl)oxy)methyl)-2,2-dimethyltetrahydrothieno[3,4-d] [1,3]dioxol-4-yl acetate. The crude product was used in next step without further purification. MS: 427 (M−OAc+1). $^1$H NMR (400 MHz, Chloroform-d) δ 7.72-7.68 (m, 4H), 7.47-7.40 (m, 6H), 6.14 (d, J=5.3 Hz, 1H), 4.88-4.85 (m, 1H), 4.70-4.68 (m, 1H), 3.93-3.75 (m, 3H), 2.18 (s, 3H), 1.58 (s, 3H), 1.36 (s, 3H), 1.10 (s, 9H).

Step 3: (3aR,6R,6aS)-6-(((tert-butyldiphenylsilyl)oxy) methyl)-2,2-dimethyltetrahydrothieno[3,4-d][1,3]dioxol-4-yl acetate (10.5 g, 21.4 mmol) was dissolved in a solution of 7 M NH$_3$ in MeOH (100 mL) under an atmosphere of argon. The reaction was stirred at room temperature for 0.5 h. The mixture was concentrated under reduced pressure. The residue was purified by column chromatography on silica (10% of EtOAc/petroleum ether) to give (3aR,6R,6aS)-6-(((tert-butyldiphenylsilyl)oxy)methyl)-2,2-dimethyltetrahydrothieno[3,4-d][1,3]dioxol-4-ol. MS: 467 (M+Na). $^1$H NMR (400 MHz, DMSO-d$_6$) δ 7.64-7.62 (m, 4H), 7.50-7.45 (m, 6H), 6.13 (d, J=3.9 Hz, 1H), 5.20-5.19 (m, 1H), 4.98-4.97 (m, 1H), 4.61-4.60 (m, 1H), 3.88-3.83 (m, 1H), 3.70-3.68 (m, 1H), 3.42-3.36 (m, 1H), 1.38 (s, 3H), 1.24 (s, 3H), 1.04 (s, 9H).

Step 4; A mixture of (3aR,6R,6aS)-6-(((tert-butyldiphenylsilyl)oxy)methyl)-2,2-dimethyltetrahydrothieno[3,4-d] [1,3]dioxol-4-ol (8 g, 18 mmol), 4-chloro-5-iodo-7H-pyrrolo[2,3-d]pyrimidine (5.53 g, 19.8 mmol) and triphenylphosphine (9.44 g, 36.0 mmol) were co-evaporated with dry toluene (three times, 100 mL each) and then re-dissolved in anhydrous THF (200 mL). The reaction mixture was cooled to 0° C. and (E)-diisopropyl diazene-1,2-dicarboxylate (7.28 g, 36.0 mmol) was added. The mixture was warmed to room temperature gradually and stirred at room temperature for 1.5 h. The reaction mixture was concentrated under reduced pressure. The residue was purified by column chromatography on silica (0-20% EtOAc/ petroleum ether) to give 7-((3aR,6R,6aS)-6-(((tert-butyldiphenylsilyl)oxy)methyl)-2,2-dimethyltetrahydrothieno[3,4-d][1,3]dioxol-4-yl)-4-chloro-5-iodo-7H-pyrrolo[2,3-d] pyrimidine. MS: 706 (M+1), $^1$H NMR (300 MHz, DMSO-d$_6$) δ 8.65-8.62 (m, 1H), 8.16-7.97 (m, 1H), 7.79-7.5.5 (m, 4H), 7.50-7.35 (m, 6H), 6.75-6.32 (m, 1H), 5.32-4.93 (m, 2H), 3.97-3.76 (m, 3H), 1.53-1.33 (m, 3H), 1.27-1.22 (m, 3H), 1.10-1.00 (m, 9H).

Step 5: To a stirred solution of 7-((3aR,6R,6aS)-6-(((tert-butyldiphenylsilyl)oxy)methyl)-2,2-dimethyltetrahydrothieno[3,4-d][1,3]dioxol-4-yl)-4-chloro-5-iodo-7H-pyrrolo[2,3-d]pyrimidine (5.6 g, 7.93 mmol) in anhydrous THF (0.50 mL) was added i-PrMgCl·LiCl (1.3 M in THF, 9.1.5 mL, 11.9 mmol) dropwise over a period of 5 min at −70° C. under an argon atmosphere. The mixture was stirred at −70° C. for 30 min, and then quenched by the addition of propan-2-ol (0.715 g, 11.9 mmol) at −70° C. The cold reaction mixture was poured into a mixture of cold saturated aq. NH$_4$Cl (120 mL). The resulting mixture was extracted with EtOAc (600 mL, then 400 mL×2). The combined organic layers were dried with anhydrous Na$_2$SO$_4$, filtered, and concentrated under reduced pressure to give 7-((3aR,6R,6aS)-6-(((tert-butyldiphenylsilyl)oxy)methyl)-2,2-dimethyltetrahydrothieno[3,4-d][1,3]dioxol-4-yl)-4-chloro-7H-pyrrolo[2,3-d]pyrimidine, which was used without further purification. MS: 580 (M+1).

Step 6: To a stirred solution of 7-((3aR,6R,6aS)-6-(((tert-butyldiphenylsilyl)oxy)methyl)-2,2-dimethyltetrahydrothieno[3,4-d][1,3]dioxol-4-yl)-4-chloro-7H-pyrrolo[2,3-d]pyrimidine (6 g, 7.9 mmol) in THF (20 mL) was added tetrabutylammonium fluoride (1 M in THF, 15.9 mL, 15.9 mmol), and the reaction mixture was stirred at room temperature for 1 h. The mixture was concentrated under reduced pressure, and the resulting residue was diluted with ethyl acetate (300 mL). The organic layer was washed with water (50 mL×3) and dried over magnesium sulfate. After filtration, the filtrate was concentrated under reduced pressure, and the residue was purified by column chromatography on silica (0-34% EtOAc/petroleum ether) to give ((3aS, 4R,6R,6aR)-6-(4-chloro-7H-pyrrolo[2,3-d]pyrimidin-7-yl)-2,2-dimethyltetrahydrothieno[3,4-d][1,3]dioxol-4-yl) methanol. MS: 342 (M+1). $^1$H NMR (300 MHz, DMSO-d$_6$) δ 8.70 (s, 1H), 8.11 (d, J=3.8 Hz, 1H), 6.78 (d, J=3.7 Hz, 1H), 6.38 (d, J=2.9 Hz, 1H), 5.37-5.26 (m, 2H), 5.01 (d, J=5.5 Hz, 1H), 3.71-3.61 (m, 3H), 1.56 (s, 3H), 1.30 (s, 3H).

Intermediate 6: ((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methanol

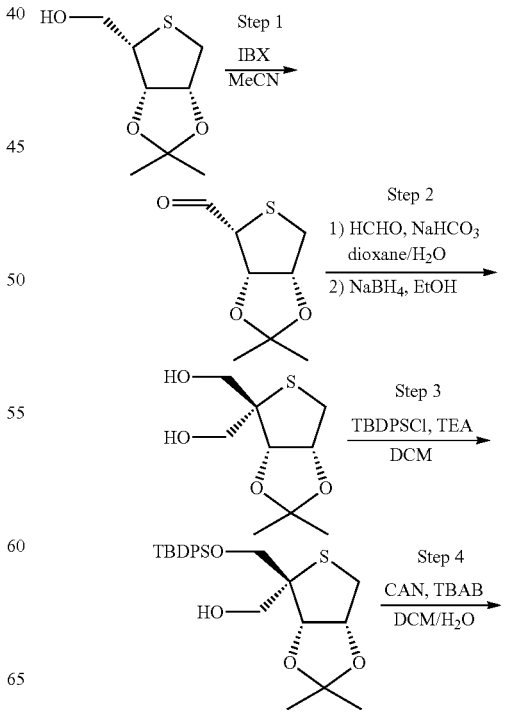

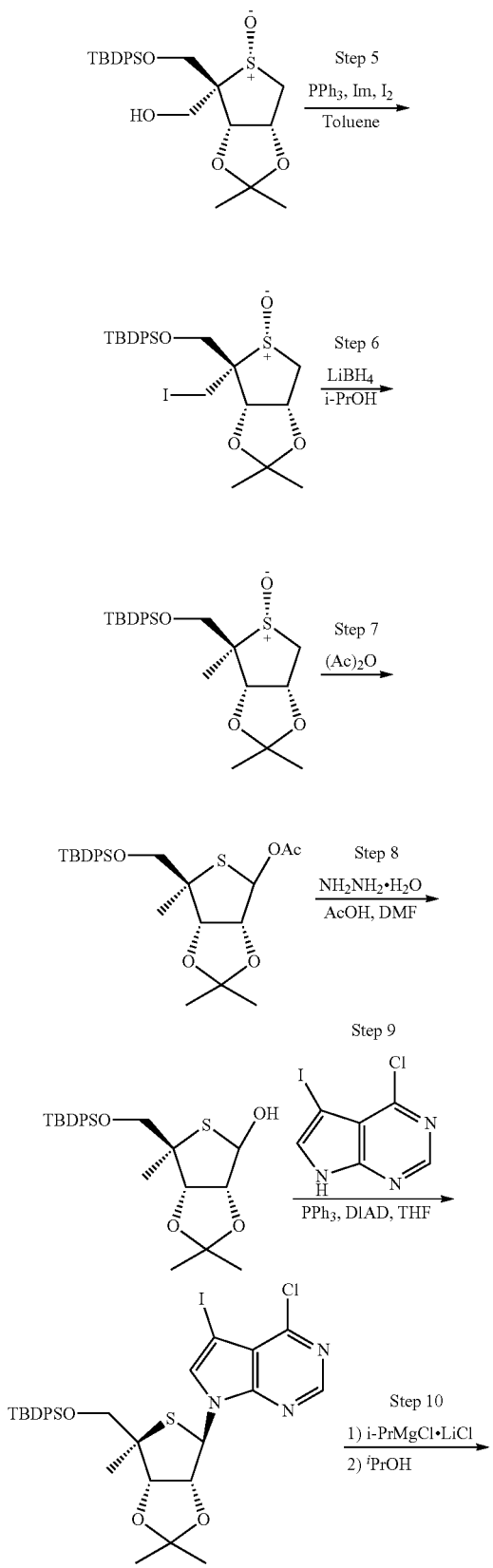

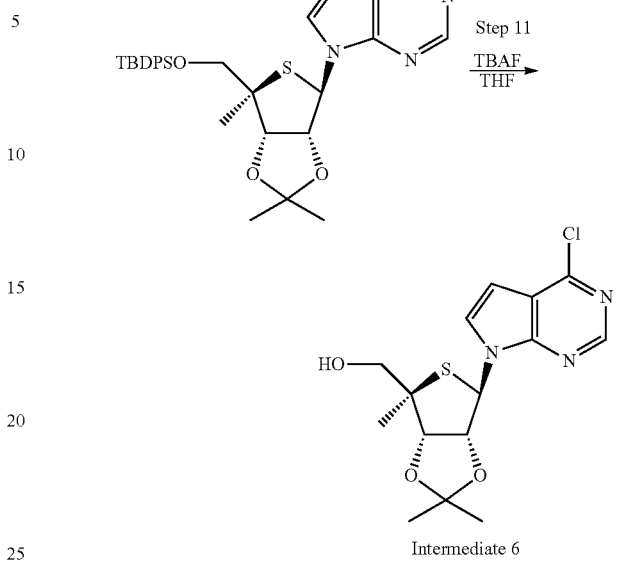

Intermediate 6

Step 1: To a solution of ((3aS,4S,6aR)-2,2-dimethyltetrahydrothieno[3,4-d][1,3]dioxol-4-yl)methanol (15 g, 79 mmol) in acetonitrile (450 mL) was added IBX (66.2 g, 237 mmol) at room temperature under an argon atmosphere. The reaction mixture was stirred for 5 h at 50° C. The reaction mixture was cooled to room temperature and the resulting mixture was filtered. The solid was washed with acetonitrile (100 mL×3). The filtrate was concentrated under reduced pressure to afford (3aS,4R,6aR)-2,2-dimethyltetrahydrothieno[3,4-d][1,3]dioxole-4-carbaldehyde, which was used in tire next step without purification. $^1$H NMR (300 MHz, DMSO-$d_6$): δ 9.59 (s, 1H), 5.17 (t, J=5.5 Hz, 1H), 4.93 (t, J=5.3 Hz, 1H), 4.22 (d, J=5.0 Hz, 1H), 2.91-2.80 (m, 2H), 1.32 (s, 3H), 1.23 (s, 3H).

Step 2: To a stirred solution of (3aS,4R,6aR)-2,2-dimethyltetrahydrothieno[3,4-d][1,3]dioxole-4-carbaldehyde (14.9 g, 79 mmol) in 1,4-dioxane (675 mL) and water (135 mL) was added formaldehyde (~37% in water, 67.5 mL, 907 mmol) and sodium bicarbonate (14.3 g, 170 mmol) at room temperature. After stirring at room temperature for 1.6 h, sodium borohydride (1.7.8 g, 471 mmol) was added in batches to the reaction solution at 0° C. After stirring at room temperature for 1 h, the resulting mixture was quenched with water (100 mL), and then neutralized with the addition of 10%-15% aqueous HCl. The mixture was extracted with DCM (300 mL×10). The combined organic layers were washed with brine (1000 mL), dried over anhydrous $Na_2SO_4$, filtered, and the filtrate was concentrated under reduced pressure. The residue was purified by column chromatography on silica (1-70% EtOAc/petroleum ether) to afford ((3aS,6aR)-2,2-dimethyltetrahydrothieno[3,4-d][1,3]dioxole-4,4-diyl)dimethanol. $^1$H NMR (300 MHz, DMSO-$d_6$): δ 4.99-4.87 (m, 2H), 4.71 (s, 1H), 4.60 (d, J=5.7 Hz, 1H), 3.80 (d, J=10.7 Hz. 1H), 3.67 (d, J=11.1 Hz, 1H), 3.52 (d, J=10.7 Hz, 1H), 3.33 (d, J=11.1 Hz, 1H), 3.08 (dd, J=12.8, 5.1 Hz, 1H), 2.67 (d, J=12.8, 1.2 Hz, 1H), 1.41 (s, 3H), 1.24 (s, 3H).

Step 3: To a mixture of ((3aS,6aR)-2,2-dimethyltetrahydrothieno[3,4-d][1,3]dioxole-4,4-diyl)dimethanol (7.05 g, 32.0 mmol) and triethylamine (9.72 g, 96 mmol) in DCM (140 mL) under an argon atmosphere was added dropwise tert-butylchlorodiphenylsilane (9.24 g, 33.6 mmol) at room temperature. The resulting mixture was stirred at room temperature for 16 h under an argon atmosphere. The mixture was concentrated under reduced pressure. The residue was purified by column chromatography on silica (0-20% of EtOAc/petroleum ether) to afford ((3aS,4R,6aR)-4-(((tert-butyldiphenylsilyl)oxy)methyl)-2,2-dimethyltetrahydrothieno[3,4-d][1,3]dioxol-4-yl)methanol. $^1$H NMR (300 MHz, DMSO-d$_6$): δ 7.70-7.67 (m, 4H), 7.50-7.46 (m, 6H), 4.88 (t, J=4.7 Hz, 1H), 4.73 (t, J=5.3 Hz, 1H), 4.57 (d, J=5.6 Hz, 1H), 3.93-3.88 (m, 2H), 3.63-3.57 (m, 2H), 2.96 (dd, J=12.9, 5.0 Hz, 1H), 2.70 (d, J=12.8 Hz, 1H), 1.42 (s, 3H), 1.23 (s, 3H), 1.03 (s, 9H).

Step 4: To a stirred solution of ((3aS,4R,6aR)-4-(((tert-butyldiphenylsilyl)oxy)methyl)-2,2-dimethyltetrahydrothieno[3,4-d][1,3]dioxol-4-yl)methanol (5 g, 10.9 mmol) in a mixture of DCM (100 mL) and water (50 mL) was added tetrabutylammonium bromide (3.87 g, 12.0 mmol) and ammonium ceric nitrate (14.9 g, 27.3 mmol) at 25° C. under an argon atmosphere. The resulting mixture was stirred at 25° C. for 5 h. The mixture was diluted with DCM (500 mL) and washed with water (300 mL×3). The organic layer was dried over anhydrous Na$_2$SO$_4$, filtered, and the filtrate was concentrated under reduced pressure. The residue was purified by column chromatography on silica (0-53% EtOAc/petroleum ether) to afford (3aS,4R,5R,6aR)-4-((tert-butyldiphenylsilyl)oxy)methyl)-4-(hydroxymethyl)-2,2-dimethyltetrahydrothieno[3,4-d][1,3]dioxole 5-oxide. MS: 475 (M+1). $^1$H NMR (300 MHz, DMSO-d$_6$): δ 7.78-7.68 (m, 4H), 7.50-7.42 (m, 6H), 5.08-5.00 (m, 2H), 4.87 (d, J=6.2 Hz, 1H), 4.17 (d, J=11.1 Hz, 1H), 4.01-3.90 (m, 2H), 3.60-3.68 (m, 2H), 3.23 (dd, J=13.2, 6.3 Hz, 1H), 1.34 (s, 3H), 1.22 (s, 3H), 1.01 (s, 9H).

Step 5: Triphenylphosphine (7.96 g, 30.3 mmol), 1H-imidazole (2.07 g, 30.3 mmol) and (3aS,4R,5R,6aR)-4-(((tert-butyldiphenylsilyl)oxy)methyl)-4-(hydroxymethyl)-2,2-dimethyltetrahydrothieno[3,4-d][1,3]dioxole 5-oxide (3.9 g, 7.81 mmol) were dissolved in toluene (50 mL) at 25° C., then I$_2$ (3.85 g, 15.2 mmol) was added in one portion. The resulting mixture was heated at 80° C. for 2 h. The reaction mixture was cooled to 0° C., quenched with saturated aqueous Na$_2$S$_2$O$_3$ (50 mL) and extracted with EtOAc (500 mL). The organic layer was washed with H$_2$O (150 mL), saturated aqueous NaHCO$_3$ (150 mL×2) and brine (150 mL) successively. The organic layer was dried over anhydrous Na$_2$SO$_4$, filtered, and the filtrate was concentrated under the reduced pressure. The residue was purified by column chromatography on silica (0-22% EtOAc/petroleum ether) to afford (3aS,4R,5R,6aR)-4-(((tert-butyldiphenylsilyl)oxy)methyl)-4-(iodomethyl)-2,2-dimethyltetrahydrothieno[3,4-d][1,3]dioxole 5-oxide MS: 607 (M+Na). $^1$H NMR (300 MHz, DMSO-d$_6$): δ 7.75-7.68 (m, 4H), 7.49-7.44 (m, 6H), 5.02-4.97 (m, 1H), 4.73 (d, J=6.1 Hz, 1H), 4.14 (d, J=11.4 Hz, 1H), 4.00-3.97 (m, 1H), 3.69-3.60 (m, 2H), 3.45 (d, J=10.3 Hz, 1H), 3.35-3.32 (m, 1H), 1.38 (s, 3H), 1.24 (s, 3H), 1.01 (s, 9H).

Step 6: To a stirred solution of (3aS,4R,5R,6aR)-4-(((tert-butyldiphenylsilyl)oxy)methyl)-4-(iodomethyl)-2,2-dimethyltetrahydrothieno[3,4-d][1,3]dioxole 5-oxide (3.5 g, 5.93 mmol) in 2-propanol (50 mL) under an argon atmosphere was added lithium borohydride (2.6 g, 120 mmol) at room temperature. The reaction mixture was stirred at 50° C. for 36 h. The reaction mixture was quenched, by adding 50 mL of saturated aqueous NH$_4$Cl at 0° C. The resulting solution was extracted with ethyl acetate (500 mL×3). The organic layers were combined, dried over anhydrous sodium sulfate, filtered, and the filtrate was concentrated under reduced pressure. The residue was purified by column chromatography on silica (0-50% EtOAc/petroleum ether) to afford (3aS,4R,5R,6aR)-4-(((tert-butyldiphenylsilyl)oxy)methyl)-2,2,4-trimethyltetrahydrothieno[3,4-d][1,3]dioxole 5-oxide. MS: 481 (M+Na). $^1$H NMR (300 MHz, DMSO-d$_6$): δ 7.68-7.65 (m, 4H), 7.48-7.41 (m, 6H), 5.14-5.12 (m, 1H), 4.67 (d, J=6.8 Hz, 1H), 3.90 (d, J=10.7 Hz, 1H), 3.78 (d, J=10.8 Hz, 1H), 3.31-3.29 (m, 2H), 1.38 (s, 3H), 1.23 (s, 6H), 0.99 (s, 9H).

Step 7: A mixture of (3aS,4R,5R,6aR)-4-(((tert-butyldiphenylsilyl)oxy)methyl)-2,2,4-trimethyltetrahydrothieno[3,4-d][1,3]dioxole 5-oxide (1.6 g, 3.45 mmol) in acetic anhydride (35 mL, 3.45 mmol) was heated at 110° C. under an argon atmosphere for 3 h. The reaction was concentrated under reduced pressure and the residue was purified, by column chromatography on silica (0-22% EtOAc/petroleum ether) to afford (3aR,6R,6aS)-6-(((tert-butyldiphenylsilyl)oxy(methyl)-2,2,6-trimethyltetrahydrothieno[3,4-d][1,3]dioxol-4-yl acetate. MS: 523 (M+Na). $^1$H NMR (300 MHz, DMSO-d$_6$): δ 7.71-7.32 (m, 10H), 6.07-5.54 (m, 1H), 4.90-4.58 (m, 1H), 4.50-4.48 (m, 1H), 3.66-3.61 (m, 2H), 1.77, 2.06 (2 s, 3H), 1.49-1.39 (m, 6H), 1.27-1.23 (m, 3H), 1.06-1.01 (m, 9H).

Step 8; Hydrazine hydrate (429 mg, 8.57 mmol) was dissolved in dry DMF (15 mL), then acetic acid (515 mg, 8.57 mmol) was added dropwise at 0° C. The resulting mixture was stirred at room temperature for about 30 minutes. To the above mixture was added (3aS,6R,6aS)-6-(((tert-butyldiphenylsilyl)oxy)methyl)-2,2,6-trimethyltetrahydrothieno[3,4-d][1,3]dioxol-4-yl acetate (1.44 g, 2.84 mmol) in 25 mL of DMF dropwise at 0° C. for over 10 min. The resulting mixture was warmed to room temperature and stirred for 6 h. The mixture was diluted with EtOAc (100 mL), washed with water (50 mL×3) and brine (50 mL). The organic layer was dried over anhydrous Na$_2$SO$_4$, filtered, and the filtrate was concentrated under reduced pressure. The residue was purified by column chromatography on silica (0-20% EtOAc/petroleum ether) to afford (3aR,6R,6aS)-6-(((tert-butyldiphenylsilyl)oxy)methyl)-2,2,6-trimethyltetrahydrothieno[3,4-d][1,3]dioxol-4-ol. MS: 481 (M+Na). $^1$H NMR (400 MHz, DMSO-d$_6$) δ 7.66-7.62 (m, 4H), 7.52-7.43 (m, 6H), 6.08 (d, J=3.7 Hz, 1H), 5.08 (d, J=3.7 Hz, 1H), 4.68 (d, J=5.5 Hz, 1H), 4.49 (d, J=5.5 Hz, 1H), 4.02-3.97 (m, 1H), 3.61 (d, J=10.3 Hz, 1H), 1.39 (s, 3H), 1.35 (s, 3H), 1.22 (s, 3H), 1.04 (s, 9H).

Step 9: A mixture of (3aR,6R,6aS)-6-(((tert-butyldiphenylsilyl)oxy)methyl)-2,2,6-trimethyltetrahydrothieno[3,4-d][1,3]dioxol-4-ol (1.12 g, 2.34 mmol), 4-chloro-5-iodo-7H-pyrrolo[2,3-d]pyrimidine (751 mg, 2.69 mmol) and triphenylphosphine (1.92 g, 7.33 mmol) was concentrated with dry toluene (3 mL×3) and then dissolved in anhydrous THF (20 mL). The reaction mixture was cooled to 0° C., and then (E)-diisopropyl diazene-1,2-dicarboxylate (1.48 g, 7.33 mmol) was added. The resulting mixture was stirred at room temperature for 1.5 h. The reaction was concentrated under reduced pressure and the residue was purified by Prep-TLC (10:1=petroleum ether:EtOAc, v:v) to give major isomer 7-((3aR,4R,6R,6aS)-6-(((tert-butyldiphenylsilyl)oxy)methyl)-2,2,6-trimethyltetrahydrothieno[3,4-d][1,3]dioxol-4-yl)-4-chloro-5-iodo-7H-pyrrolo[2,3-d]pyrimidine. MS: 720 (M+1). $^1$H NMR (300 MHz, Chloroform-d): δ 8.63 (s, 1H), 7.66 (s, 1H), 7.64-7.56 (m, 1H), 7.44-7.30 (m, 6H), 6.17 (d, J=3.1 Hz, 1H), 4.69 (dd, J=5.4, 3.2 Hz, 1H), 4.59 (d, J=5.5 Hz, 1H), 3.77 (d, J=10.4 Hz, 1H), 3.62 (s, 1H), 1.64 (s, 3H), 1.57 (s, 3H), 1.31 (s, 3H), 1.11 is, 9H).

Step 10: To a stirred solution of 7-((3aR,4R,6R,6aS)-6-(((tert-butyldiphenylsilyl)oxy)methyl)-2,2,6-trimethyltetra-hydrothieno[3,4-d][1,3]dioxol-4-yl)-4-chloro-5-iodo-7H-pyrrolo[2,3-d]pyrimidine (380 mg, 0.528 mmol) in anhydrous THF (6 mL) was added isopropylmagnesium chloride-lithium chloride complex (0.609 mL, 1.3 M in THF, 0.792 mmol) over a period of 5 minutes at −70° C. The mixture was stirred at −70° C. for 30 minutes, and then quenched by dropwise addition of propan-2-ol (5 mL) at −70° C. The cold reaction mixture was poured into 50 mL of cold saturated aqueous $NH_4Cl$. The resulting mixture was extracted with EtOAc (100 mL×3). The combined organic layers were dried over anhydrous $Na_2SO_4$ and filtered. The filtrate was concentrated under reduced pressure to afford 7-((3aR,4R,6R,6aS)-6-(((tert-butyldiphenylsilyl)oxy)methyl)-2,2,6-trimethyltetrahydrothieno[3,4-d][1,3]dioxol-4-yl)-4-chloro-7H-pyrrolo[2,3-d]pyrimidine. MS: 594 (M+1). $^1$H NMR (300 MHz, Chloroform-d): δ 8.62 (s, 1H), 7.62-7.58 (m, 4H), 7.43-7.26 (m, 7H), 6.46 (d, J=3.7 6.20 (d, J=3.2 Hz, 1H), 4.79 (dd, J=5.5, 3.2 Hz, 1H), 4.64 (d, J=5.5 Hz, 1H), 3.74 (d, J=10.4 Hz, 1H), 3.64 (d, J=10.4 Hz, 1H), 1.66 (s, 3H), 1.59 (s, 3H), 1.33 (s, 3H), 1.10 (s, 9H).

Step 11: To a stirred solution of 7-((3aR,4R,6R,6aS)-6-(((tert-butyldiphenylsilyl)oxy)methyl)-2,2,6-trimethyltetra-hydrothieno[3,4-d][1,3]dioxol-4-yl)-4-chloro-7H-pyrrolo[2,3-d]pyrimidine (278 mg, 0.468 mmol) in fill (5 mL) was added TBAF (1 M in THF, 0.515 mL, 0.515 mmol) at room temperature. The resulting mixture was stirred at room temperature for 1.5 h. The mixture was concentrated under reduced pressure and the residue was purified by Prep-TLC (petroleum ether:EtOAc=1:1, v:v) to afford ((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methanol. MS: 356 (M+1). $^1$H NMR (300 MHz, DMSO-$d_6$): δ 8.67 (s, 1H), 8.20 (d, J=3.8 Hz, 1H), 6.76 (d, J=3.8 Hz, 1H), 6.38 (d, J=3.8 Hz, 1H), 5.56 (t, J=5.2 Hz, 1H), 5.34-5.21 (m, 1H), 4.65 (d, J=5.2 Hz, 1H), 3.61-3.49 (m, 2H), 1.57 (s, 3H), 1.37 (s, 3H), 1.28 (s, 3H).

Intermediate 7: 4-Chloro-7-((3aR,4R,6aS)-2,2-dimethyl-6-vinyltetrahydrothieno[3,4-d][1,3]dioxol-4-yl)-7H-pyrrolo[2,3-d]pyrimidine Intermediate 7a: 4-Chloro-7-((3aR,4R,6R,6aS)-2,2-dimethyl-6-vinyltetrahydrothieno[3,4-d][1,3]dioxol-4-yl)-7H-pyrrolo[2,3-d]pyrimidine Intermediate 7b: 4-Chloro-7-((3aR,4R,6S,6aS)-2,2-dimethyl-6-vinyltetrahydrothieno[3,4-d][1,3]dioxol-4-yl)-7H-pyrrolo[2,3-d]pyrimidine

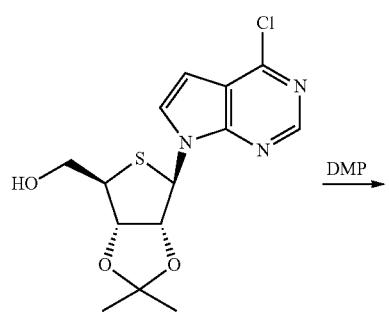

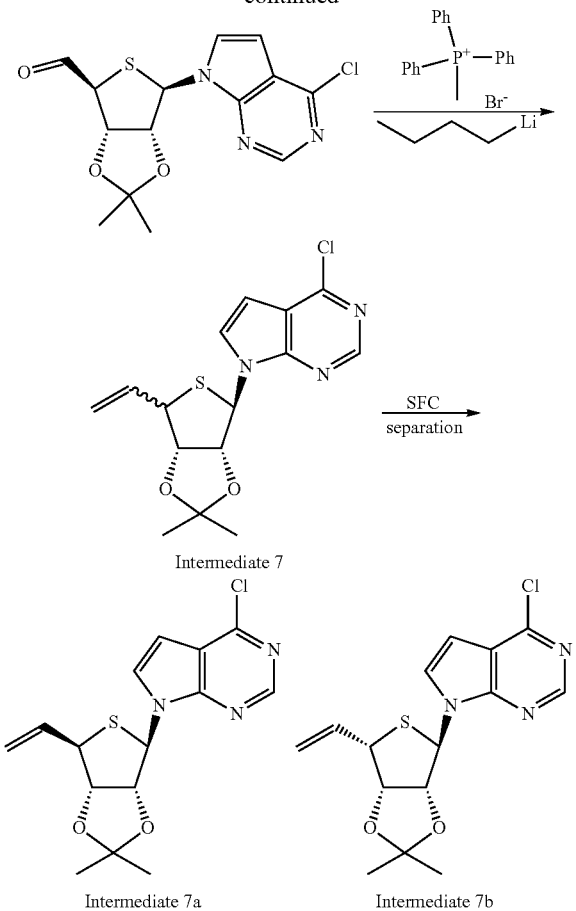

Step 1: To a stirred solution of ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol (2.14 g, 6.26 mmol) in DCM (50 mL) was added Dess-Martin periodinane (4 g, 9.43 mmol). The reaction was stirred at room temperature overnight. The mixture was diluted with EtOAc and washed with a mixture of aqueous sodium thiosulfate and saturated sodium bicarbonate. The organic layer was washed with brine, dried over anhydrous $MgSO_4$, filtered, and concentrated under reduced pressure to afford (3aS,4S,6R,6aR)-6-(4-chloro-7H-pyrrolo[2,3-d]pyrimidin-7-yl)-2,2-dimethyltetrahydrothieno[3,4-d][1,3]dioxole-4-carbaldehyde as a solid, which was used in the next step without purification.

Step 2: To a mixture of methyltriphenylphosphonium bromide (2.3 g, 6.45 mmol) in THF (35 mL) cooled to −78° C. was added n-butyllithium (1.6 M in hexane, 4.03 mL, 6.45 mmol) dropwise under nitrogen. The mixture was stirred at 0° C. for 35 minutes. The flask was cooled back down to −78° C. and (3aS,4S,6R,6aR)-6-(4-chloro-7H-pyrrolo[2,3-d]pyrimidin-7-yl)-2,2-dimethyltetrahydrothieno[3,4-d][1,3]dioxole-4-carbaldehyde (1.46 g, 4.30 mmol) was added as a solution in THF (7 mL) via syringe. The mixture was allowed to warm to room temperature and stirred overnight. The reaction mixture was poured into a solution of saturated aqueous $NH_4Cl$ and EtOAc. The aqueous layer was extracted with EtOAc, and the combined organic layers were washed with brine, dried over $MgSO_4$, filtered, and concentrated under reduced pressure. The residue was purified by column chromatography on silica (0-20% EtOAc/ hexanes) to afford 4-chloro-7-((3aR,4R,6aS)-2,2-dimethyl-6-vinyltetrahydrothieno[3,4-d][1,3]dioxol-4-yl)-7H-pyrrolo[2,3-d]pyrimidine (Intermediate 7). MS: 338 (M+1). Intermediate 7 was subjected to SFC separation (CCC column, 10%/90% (MeOH w/0.25% DMEA)/CO₂) to afford two isomers:

4-Chloro-7-((3aR,4R,6R,6aS)-2,2-dimethyl-6-vinyltetrahydrothieno[3,4-d][1,3]dioxol-4-yl)-7H-pyrrolo[2,3-d]pyrimidine (Intermediate 7a)_MS: 338 (M+1). ¹H NMR (600 MHz, CDCl₃) δ 8.72 (s, 1H), 7.54 (d, J=3.7 Hz, 1H), 6.69 (d, J=3.7 Hz, 1H), 6.44 (d, J=3.0 Hz, 1H), 6.00 (ddd, J=17.0, 10.1, 8.1 Hz, 1H), 5.36 (d, J=16.9 Hz, 1H), 5.26 (d, J=10.1 Hz, 1H), 5.12 (dd, J=6.0, 3.0 Hz, 1H), 4.91 (dd, J=5.9, 4.5 Hz, 1H), 4.23 (dd, J=8.0, 4.3 Hz, 1H), 1.68 (s, 3H), 1.36 (s, 3H).

4-Chloro-7-((3aR,4R,6S,6aS)-2,2-dimethyl-6-vinyltetrahydrothieno[3,4-d][1,3]dioxol-4-yl)-7H-pyrrole[2,3-d]pyrimidine (Intermediate 7b) MS: 338 (M+1). ¹H NMR (600 MHz, CDCl₃) δ 8.69 (s, 1H), 7.39 (d, J=3.7 Hz, 1H), 6.66 (d, J=3.7 Hz, 1H), 6.04 (ddd, J=17.2, 10.0, 8.9 Hz, 1H), 5.95 (s, 1H), 5.38 (d, 7=18.9 Hz, 1H), 5.36-5.34 (m, 1H), 5.29 (d, J=10.2 Hz, 1H), 5.13-5.11 (m, 1H), 4.79 (dd, J=8.8, 4.2 Hz, 1H), 1.66 (s, 3H), 1.39 (s, 3H).

Intermediate 8: 4-Chloro-7-((3aR,4R,6R,6aS)-2,2,6-trimethyl-6-vinyltetrahydrothieno[3,4-d][1,3]dioxol-4-yl)-7H-pyrrolo[2,3-d]pyrimidine

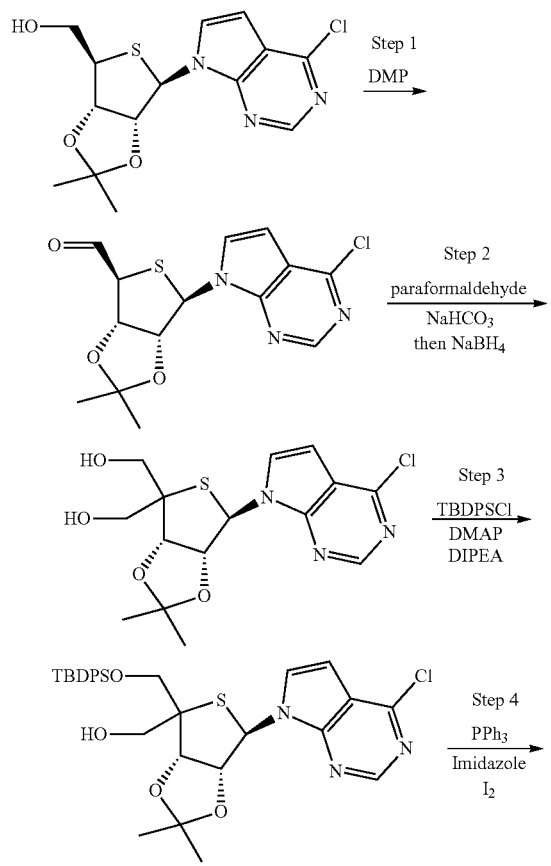

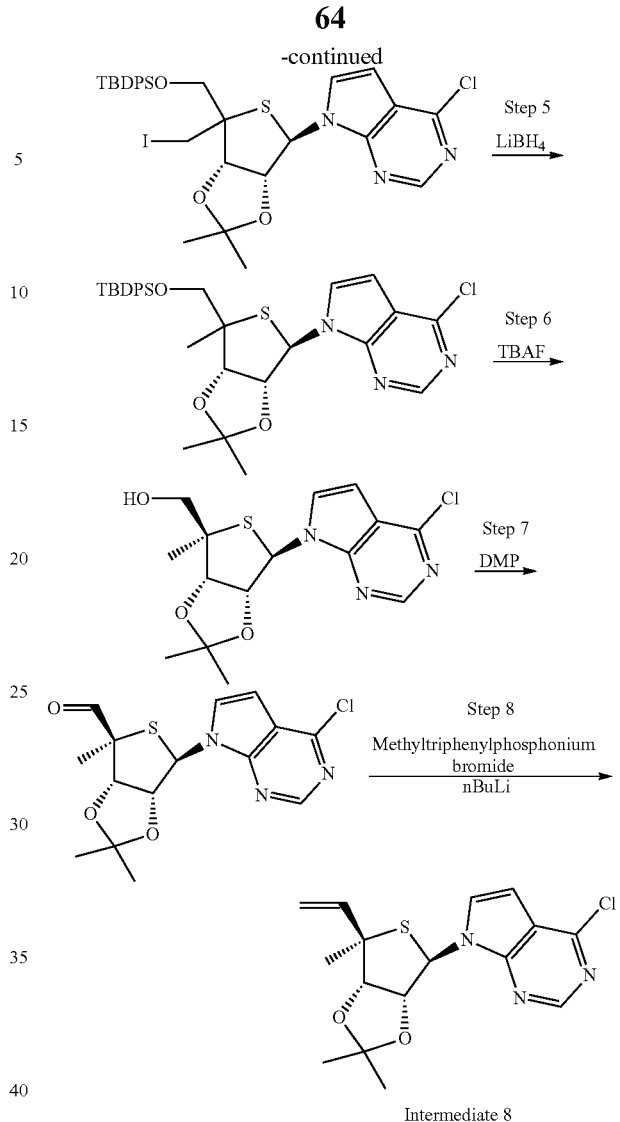

Intermediate 8

Step 1: To a stirred solution of ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol (13 g, 38 mmol) in DCM (200 mL) was added Dess-Martin Periodinane (21 g, 50 mmol). The reaction was stirred at room temperature for 3 h. The reaction was then poured into a separatory funnel containing DCM and a mixture of aqueous sodium thiosulfate and saturated aqueous sodium bicarbonate. The organic layer was dried over magnesium sulfate, filtered over Celite, and concentrated under reduced pressure to afford (3aR,4S,6R,6aR)-6-(4-chloro-7H-pyrrolo[2,3-d]pyrimidin-7-yl)-2,2-dimethyltetrahydrothieno[3,4-d][1,3]dioxole-4-carbaldehyde as an amorphous solid, which was used in the next step without purification. ¹H NMR (600 MHz, CDCl₃) δ 9.60 (s, 1H), 8.59 (s, 1H), 7.18 (d, J=3.7 Hz, 1H), 6.62 (d, J=3.7 Hz, 1H), 6.26 (s, 1H), 5.66 (d, J=5.3 Hz, 1H), 5.22 (d, J=5.4 Hz, 1H), 4.21 (s, 1H), 1.64 (s, 3H), 1.37 (s, 3H).

Step 2: To a 1 L round bottom flask containing (3aS,4S,6R,6aR)-6-(4-chloro-7H-pyrrolo[2,3-d]pyrimidin-7-yl)-2,2-dimethyltetrahydrothieno[3,4-d][1,3]dioxole-4-carbaldehyde (12.6 g, 37.1 mmol) was added paraformaldehyde (22.3 g, 742 mmol), followed by 1,4-dioxane (262 mL) and water (20 mL). Sodium bicarbonate (21.8 g, 260 mmol) was added, and the reaction was stirred at room temperature overnight. The reaction was then cooled to 0° C., and sodium borohydride (8.42 g, 222 mmol) was added slowly portionwise. After addition, the ice bath was removed, and the reaction was stirred at room temperature for 1 h. The reaction was then decanted into a separator funnel containing saturated aqueous sodium bicarbonate, brine, and 25% isopropanol/chloroform. The aqueous layer was extracted twice more with 25% isopropanol/chloroform. The combined organic layers were dried over sodium sulfate, filtered over Celite, and concentrated under reduced pressure. The residue was purified by column chromatography on silica (70-90% EtOAc/hexanes) to afford ((3aS; 6R; 6aR)-6-(4-chloro-7H-pyrrolo[2,3-d]pyrimidin-7-yl)-2,2-dimethyltetrahydrothieno[3,4-d][1,3]dioxole-4,4-diyl)dimethanol as a solid. MS: 372 (M+1).

Step 3: To a 500 ml, round bottom flask containing ((3aS,6R,6aR)-6-(4-chloro-7H-pyrrolo[2,3-d]pyrimidin-7-yl)-2,2-dimethyltetrahydrothieno[3,4-d][1,3]dioxole-4,4-diyl)dimethanol (5.2 g, 14.0 mmol) was added DCM (190 mL). Then, N,N-diisopropylethylamine (6 mL, 34.4 mmol) and DMAP (1.88 g, 15.4 mmol) were added. Finally, tert-butyldiphenylchlorosilane (4 mL, 15.3 mmol) was added, and the reaction was stirred at room temperature overnight. The reaction was then poured into a separatory funnel containing saturated ammonium chloride, water, and DCM. The organic layer was then dried over magnesium sulfate, filtered, and concentrated under reduced pressure. The residue was purified by column chromatography on silica (20-30-40% EtOAc/hexanes) to afford ((3aS,6R,6aR)-4-(((tert-butyldiphenylsilyl)oxy)methyl)-6-(4-chloro-7H-pyrrolo[2,3-d]pyrimidin-7-yl)-2,2-dimethyltetrahydrothieno[3,4-d][1,3]dioxol-4-yl)methanol as a solid. MS: 610 (M+1).

Step 4: To a 500 mL round bottom flask containing a solution of ((3aS,6R,6aR)-4-(((tert-butyldiphenylsilyl)oxy)methyl)-6-(4-chloro-7H-pyrrolo[2,3-d]pyrimidin-7-yl)-2,2-dimethyltetrahydrothieno[3,4-d][1,3]dioxol-4-yl)methanol (6.85 g, 11.2 mmol) in DCM (200 ml) was added triphenylphosphine (8.83 g, 33.7 mmol) and imidazole (3.82 g, 56.1 mmol). The mixture was heated to 40° C., and then iodine (8.55 g, 33.7 mmol) was added portionwise. The reaction vessel was fitted with a condenser and stirred at 40° C. under an argon atmosphere for 1 h. The reaction was cooled to room temperature, and then poured into a separatory funnel containing water, aqueous sodium thiosulfate, and DCM. The mixture was extracted, and the organic layer was dried over sodium sulfate, filtered, and concentrated under reduced pressure. The residue was purified by column chromatography on silica (0-5-10% EtOAc/hexanes) to afford 7-((3aR,4R,6aS)-6-(((tert-butyldiphenylsilyl)oxy)methyl)-6-(iodomethyl)-2,2-dimethyltetrahydrothieno[3,4-d][1,3]dioxol-4-yl)-4-chloro-7H-pyrrolo[2,3-d]pyrimidine as a solid. MS: 720 (M+1).

Step 5: To a 500 mL round bottom flask containing a solution of 7-((3aR,4R,6aS)-6-(((tert-butyldiphenylsilyl)oxy)methyl)-6-(iodomethyl)-2,2-dimethyltetrahydrothieno[3,4-d][1,3]dioxol-4-yl)-4-chloro-7H-pyrrolo[2,3-d]pyrimidine (7.6 g, 10.6 mmol) in 2-propanol (100 mL) was added lithium borohydride in THE (56 ml, 112 mmol, 2 M). The reaction was heated at 45° C. under an argon atmosphere overnight. The reaction was cooled to room temperature, and poured into a separatory funnel containing saturated aqueous ammonium chloride and 25% isopropanol/chloroform. The aqeuous layer was extracted again with 25% isopropanol/chloroform. The combined organic layers were dried over magnesium sulfate, filtered, and concentrated under reduced pressure. The residue was purified by column chromatography on silica (5-10-15% EtAOc/hexanes) to afford 7-((3aR,4R,6aS)-6-(((tert-butyldiphenylsilyl)oxy)methyl)-2,2,6-trimethyltetrahydrothieno[3,4-d][1,3]dioxol-4-yl)-4-chloro-7H-pyrrolo[2,3-d]pyrimidine as a solid. MS: 594 (M+1).

Step 6: To a 200 mL round bottom flask containing 7-((3aR,4R,6aS)-6-(((tert-butyidiphenylsilyl)oxy)methyl)-2,2,6-trimethyltetrahydrothieno[3,4-d][1,3]dioxol-4-yl)-4-chloro-7H-pyrrolo[2,3-d]pyrimidine (4.32 g, 7.27 mmol) was added THF (50 mL), followed by TBAF (18 mL, 18.0 mmol, 1M in THF). The reaction was stirred at room temperature for 1 h. Then, more TBAF (15 mL, 15 mmol, 1M in THF) was added, and the reaction was stirred for another 75 minutes at room temperature. The reaction was concentrated under reduced pressure, and the residue was purified by column chromatography on silica (10-30-40% EtOAc/hexanes) to afford ((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methanol as a foam MS: 356 (M+1).

Step 7: To a 200 mL round bottom flask containing ((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methanol (775 mg, 2.18 mmol) and DCM (50 mL) was added Dess-Martin Periodinane (1.63 g, 3.92 mmol). The reaction was stirred at room temperature for 2 h. The reaction was transferred to a separatory funnel containing saturated aqueous sodium bicarbonate, an aqueous solution of sodium thiosulfate, and DCM. The organic layer was dried over magnesium sulfate, filtered, and concentrated under reduced pressure to afford (3aS,4S,6R,6aR)-6-(4-chloro-7H-pyrrolo[2,3-d]pyrimidin-7-yl)-2,2,4-trimethyltetrahydrothieno[3,4-d][1,3]dioxole-4-carbaldehyde as a solid, which was used in the next step without purification. $^1$H NMR (600 MHz, CDCl$_3$) δ 9.40 (s, 1H), 8.65 (s, 1H), 7.21 (d, J=3.8 Hz, 1H), 6.62 (d, J=3.7 Hz, 1H), 6.46 (s, 1H), 5.26 (dd, J=5.1, 1.7 Hz, 1H), 5.13 (d, J=5.1 Hz, 1H), 1.69 (s, 3H), 1.61 (s, 314), 1.40 (s, 314).

Step 8: To an oven-dried, argon-backfilled 50 mL round bottom flask was added methyltriphenylphosphonium bromide (3.11 g, 8.72 mmol) and THF (10 mL). The flask was cooled to −78° C., and n-butyllithium in THF (2.2 mL, 5.50 mmol, 2.5 M) was added dropwise under an argon atmosphere. The reaction was warmed to 0° C., where it was vigorously stirred for 30 minutes. Then, the reaction was cooled back down to −78° C., and a solution of (3aS,4S,6R,6aR)-6-(4-chloro-7H-pyrrolo[2,3-d]pyrimidin-7-yl)-2,2,4-trimethyltetrahydrothieno[3,4-d][1,3]dioxole-4-carbaldehyde in THF (10 mL) was added in three portions. After addition, the reaction was warmed to room temperature and stirred vigorously overnight. The reaction was poured into a separatory funnel containing saturated aqueous ammonium chloride and EtOAc. The aqeuous layer was washed with EtOAc (2×), and the combined organic layers were dried over magnesium sulfate, filtered, and concentrated under reduced pressure. The residue was purified by column chromatography on silica (10-15-20% EtOAc/hexanes) to afford 4-chloro-7-((3aR,4R,6R,6aS)-2,2,6-trimethyl-6-vinyltetrahydrothieno[3,4-d][1,3]dioxol-4-yl)-7H-pyrrolo[2,3-d]pyrimidine as an oil. MS: 352 (M+1).

Intermediate 9: 7-((3aR,4R,6aS)-2,2-dimethyl-6-vinyltetrahydrothieno[3,4-d][1,3]dioxol-4-yl)-4-methyl-7H-pyrrolo[2,3-d]pyrimidine Intermediate 9b: 7-((3aR,4R,6S,6aS)-2,2-dimethyl-6-vinyltetrahydrothieno[3,4-d][1,3]dioxol-4-yl)-4-methyl-7H-pyrrolo[2,3-d]pyrimidine Intermediate 9a: 7-((3aR,4R,6R,6aS)-2,2-dimethyl-6-vinyltetrahydrothieno[3,4-d][1,3]dioxol-4-yl)-4-methyl-7H-pyrrolo[2,3-d]pyrimidine

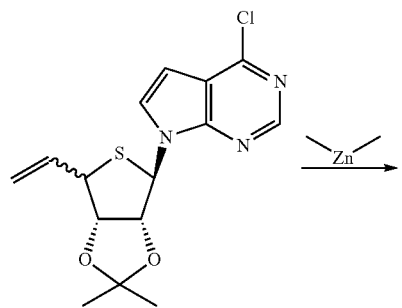

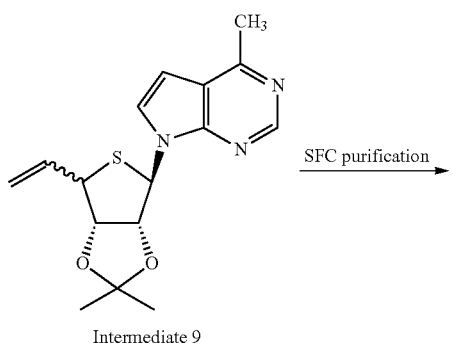

Intermediate 9

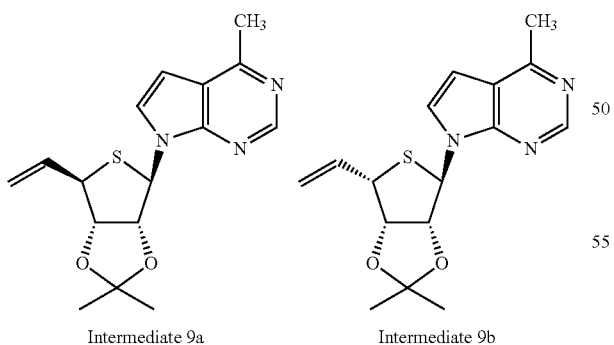

Intermediate 9a    Intermediate 9b

To a vial containing chloro[(4,5-bis(diphenylphosphino)-9,9-dimethylxanthene)-2-(2-amino-1,1-biphenyl)]palladium (II) (127 mg, 0.143 mmol) and 4-chloro-7-((3aR,4R,6aS)-2,2-dimethyl-6-vinyltetrahydrothieno[3,4-d][1,3]dioxol-4-yl)-7H-pyrrolo[2,3-d]pyrimidine (482 mg, 1.4 mmol) at 0° C. was added THF (12 mL) and dimethyl zinc (2M in toluene, 3.57 mL, 7.13 mmol). The mixture was stirred at room temperature for 30 minutes. The mixture was concentrated under reduced pressure. The residue was purified by column chromatography on silica (20% EtOAc/hexanes) to afford 7-((3aR,4R,6aS)-2,2-dimethyl-6-vinyltetrahydrothieno[3,4-d][1,3]dioxol-4-yl)-4-methyl-7H-pyrrolo[2,3-d]pyrimidine (Intermediate 9). MS: 318 (M+1). Intermediate 9 was subjected SFC separation (CCC, 90%/10% (MeOH w/0.1% NH$_4$OH)/CO$_2$) to afford two isomers both as solids.

Intermediate 9b (first eluting): 7-((3aR,4R,6S,6aS)-2,2-dimethyl-6-vinyltetrahydrothieno[3,4-d][1,3]dioxol-4-yl)-4-methyl-7H-pyrrolo[2,3d]pyrimidine. MS: 318 (M+1), 1H NMR (600 MHz, CDCl3) δ 8.79 (s, 1H), 7.27 (d, J=3.7 Hz, 1H), 6.59 (d, J=3.6 Hz, 1H), 6.04 (ddd, J=17.2, 10.1, 8.8 Hz, 1H), 5.94 (s, 1H), 5.40 (d, J=5.3 Hz, 1H), 5.36 (d, J=17.2 Hz, 1H), 5.29-5.24 (m, 1H), 5.18-5.11 (m, 1H), 4.83 (dd, J=8.8, 4.2 Hz, 1H), 2.74 (s, 3H), 1.65 (s, 3H), 1.38 (s, 3H).

Intermediate 9a (second eluting): 7-((3aR,4R,6R,6aS)-2,2-dimethyl-6-vinyltetrahydrothieno[3,4-d][1,3]dioxol-4-yl)-4-methyl-7H-pyrrolo[2,3-d]pyrimidine. MS: 318 (M+1), 1H NMR (600 MHz, CDCl3) δ 8.79 (s, 1H), 7.39 (d, J=3.7 Hz, 1H), 6.58 (d, J=3.7 Hz, 1H), 6.43 (d, J=3.0 Hz, 1H), 5.96 (ddd, J=17.1, 10.1, 8.2 Hz, 1H), 5.31 (d, J=16.9 Hz, 1H), 5.19 (d, J=10.1 Hz, 1H), 5.10 (dd, J=6.1, 3.1 Hz, 1H), 4.90-4.85 (m, 1H), 4.17 (dd, J=8.0, 4.6 Hz, 1H), 2.70 (s, 3H), 1.62 (s, 3H), 1.31 (s, 3H).

Intermediate 10:
7-bromo-N-(2,2-difluoroethyl)-2-quinolinamine

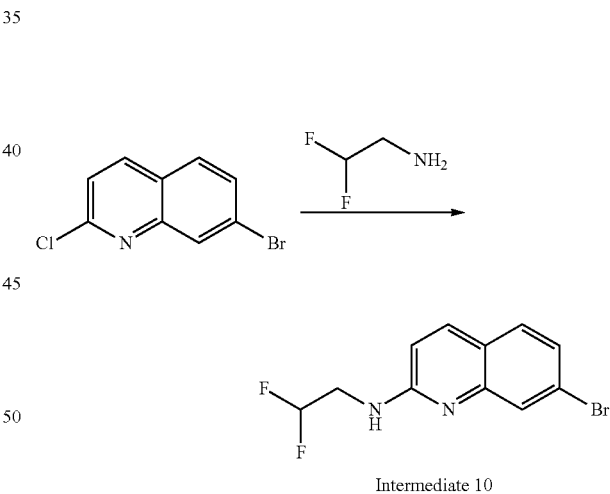

Intermediate 10

A mixture of 7-bromo-2-chloroquinoline (1.50 g, 6.19 mmol) and 2,2-difluoroethylamine (0.654 mL, 9.28 mmol) in ethanol (15 mL) was heated to 150° C. in a microwave reactor for 40 h. The mixture was concentrated, and the residue was purified by column chromatography on silica (0-35% EtOAc/hexane) to afford 7-bromo-N-(2,2-difluoroethyl)-2-quinolinamine. MS: 287, 289 (M+1). $^1$H NMR (500 MHz, DMSO-d$_6$) δ 7.94 (d, J=8.9 Hz, 1H), 7.71 (d, J=1.9 Hz, 1H), 7.62 (d, J=8.4 Hz, 2H), 7.33 (dd, J=8.4, 2.0 Hz, 1H), 6.89 (d, J=8.9 Hz, 1H), 6.22 (it, J=56.4, 4.1 Hz, 1H), 3.83 (tdd, J=15.6, 5.8, 4.2 Hz, 2H).

Intermediate 11: di-tert-butyl (4-methyl-7H-pyrrolo[2,3-d]pyrimidin-2-yl)imidodicarbonate

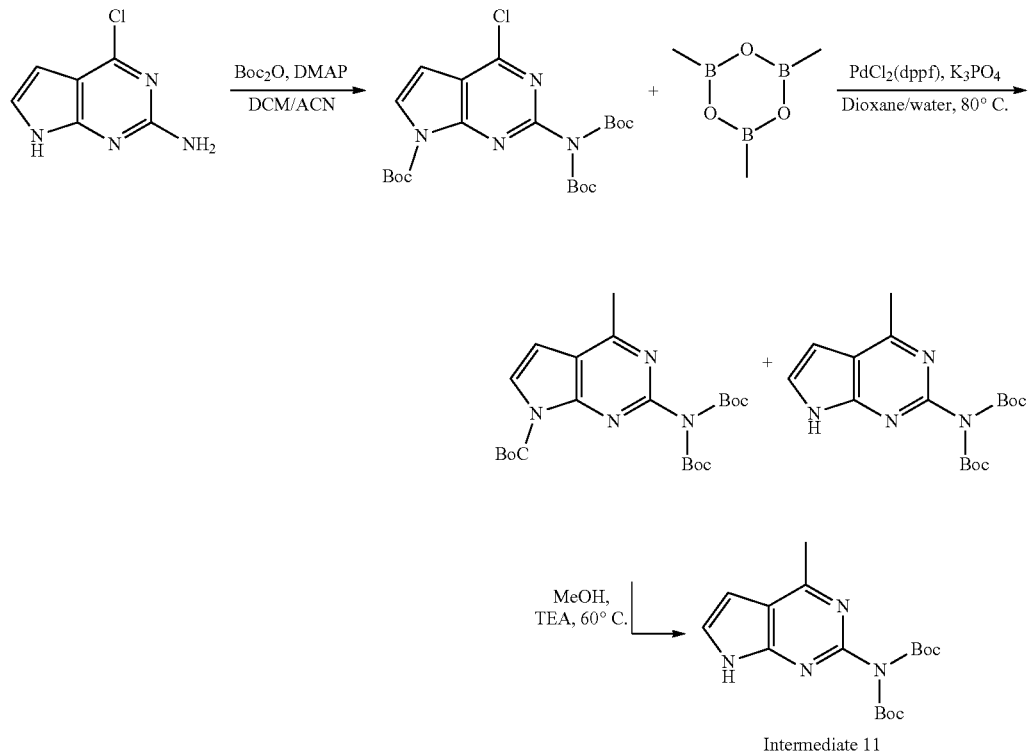

Intermediate 11

Step 1: To 4-chloro-7H-pyrrolo[2,3-d]pyrimidin-2-amine (1.0 g, 5.9 mmol) dissolved in DCM (15 mL) and acetonitrile (15 mL) was added di-tert-butyl dicarbonate (4.53 g, 20.8 mmol) and DMAP (0,145 g, 1.19 mmol). The solution was stirred at room temperature for 16 h. The mixture was concentrated under reduced pressure, and the residue was purified by column chromatography on silica (0-40% EtOAc/Hexanes) to afford tert-butyl 2-[bis(tert-butoxycarbonyl)amino]-4-chloro-7H-pyrrolo[2,3-d]pyrimidine-7-carboxylate as a foam. MS: 469 (M+1).

Step 2: To a solution of tert-butyl 2-[bis(tert-butoxycarbonyl)amino]4-chloro-7H-pyrrolo[2,3-d]pyrimidine-7-carboxylate (500 mg, 1.07 mmol), potassium phosphate (679 mg, 3.20 mmol), and PdCl$_2$(dppf) (156 mg, 0.213 mmol) dissolved in dioxane (7 mL) and water (0.34 mL) was added trimethylboroxine (297 µL, 2.13 mmol). The mixture was stirred at 80° C. for 16 h. The mixture was cooled to room temperature, quenched with water, and extracted with EtOAc (2×). The combined organic layers were dried over anhydrous sodium sulfate, filtered, and concentrated under reduced pressure. The residue was purified by column chromatography on silica (0-50% EtOAc/hexanes) to afford the following:

Peak 1: tert-butyl 2-[bis(tert-butoxycarbonyl)amino]-4-methyl-7H-pyrrolo[2,3-d]pyrimidine-7-carboxylate as a solid foam. MS: 449 (M+1).

Peak 2: di-tert-butyl (4-methyl-7H-pyrrolo[2,3-d]pyrimidin-2-yl)imidodicarbonate as a solid foam. MS: 349 (M+1).

Step 3: To a solution of tert-butyl 2-[bis(tert-butoxycarbonyl)amino]-4-methyl-7H-pyrrolo[2,3-d]pyrimidine-7-carboxylate (200 mg, 0.446 mmol) in MeOH (2.2 mL) was added triethylamine (622 µL, 4.46 mmol) at room temperature. The mixture was stirred at 60° C. for 18 h. The reaction was cooled to room temperature and concentrated under reduced pressure. The residue was purified by column chromatography on silica (0-60% EtOAc/hexanes) to afford di-tert-butyl (4-methyl-7H-pyrrolo[2,3-d]pyrimidin-2-yl)imidodicarbonate as a solid. MS: 349 (M+1). $^1$H NMR (600 MHz, DMSO-d6) δ 12.11 (s, 1H), 7.57-7.52 (m, 1H), 6.72-6.66 (m, 1H), 2.65 (s, 3H), 1.39 (s, 18H).

Intermediate 12: 7-bromo-2-methyl-2,3-dihydro-1H-pyrrolo[2,3-b]quinoline

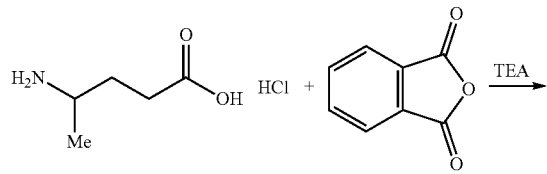

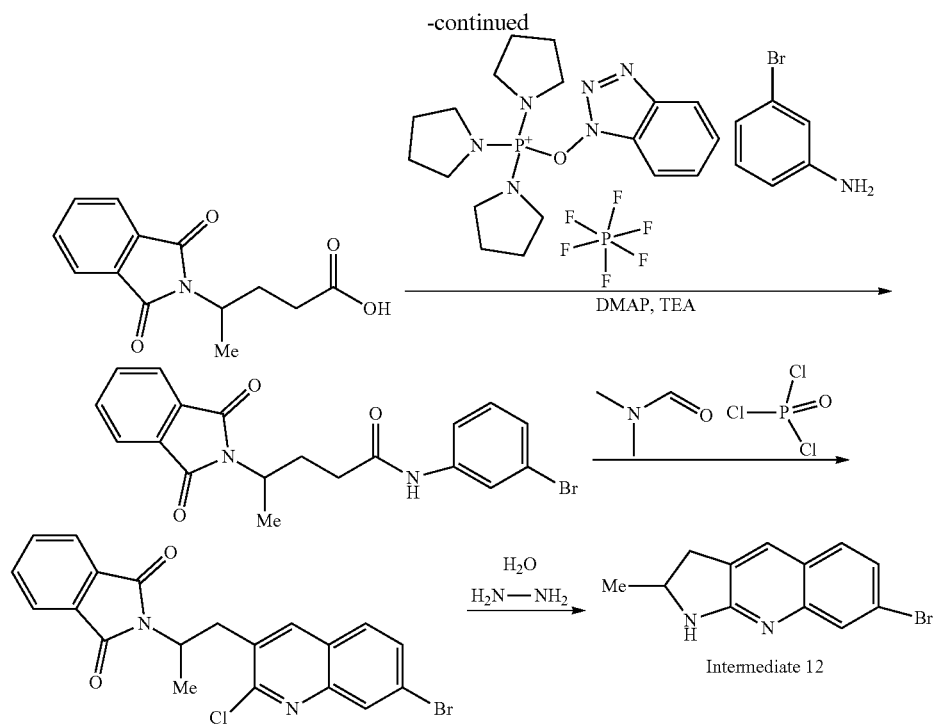

Step 1: To a stirred solution of 4-aminopentanoic acid hydrochloride (36.4 g, 237 mmol) in toluene (400 mL) was added isobenzofuran-1,3-dione (52.6 g, 355 mmol) and triethylamine (66.1 mL, 474 mmol) at room temperature. The reaction was stirred at 90° C. for 16 h. The reaction mixture was concentrated under reduced pressure and the residue was purified by column chromatography on silica (0.1-10% EtOAc/petroleum ether) to afford 4-(1,3-dioxoisoindolin-2-yl)pentanoic acid as a solid. MS: 248 (M+1).

Step 2: To a stirred solution of 4-(1,3-dioxoisoindolin-2-yl)pentanoic acid (49.4 g, 200 mmol) in DCM (400 mL) were added PYBOP (104 g, 200 mmol), 3-bromoaniline (26 mL, 240 mmol), N,N-dimethylpyridin-4-amine (2.44 g, 20.0 mmol) and triethylamine (84 mL, 600 mmol) at room temperature. The reaction was stirred for 16 h at room temperature. The reaction mixture was washed with sat. NH₄Cl (3×300 mL) and sat. NaHCO₃ (3×300 mL). The organic layer was washed with brine (2×500 mL), dried over anhydrous sodium sulfate and filtered. The filtrate was concentrated under reduced pressure. The residue was purified by column chromatography on silica (10-15% EtOAc/petroleum ether) to afford N-(3-bromophenyl)-4-(1,3-dioxoisoindolin-2-yl)pentanamide as a solid. MS: 401, 403 (M+1)

Step 3: To a solution of phosphorus oxychloride (2.2 mL, 23.7 mmol) was added DMF (0.37 mL, 4.8 mmol) at 0° C. The mixture was stirred at rt for 2 minutes. Then a solution of N-(3-bromophenyl)-4-(1,3-dioxoisoindolin-2-yl)pentanamide (1.27 g, 3.17 mmol) in toluene (50 mL) was added. The mixture was stirred at 80° C. for 16 h. The mixture was cooled to room temperature and poured into ice, then basified by addition of 4N aqueous NaOH (50 mL) and extracted with ethyl acetate (100 mL×3). The combined organic layers were washed with brine (300 mL), dried over anhydrous sodium sulfate and filtered. The filtrate was concentrated under reduced pressure to afford 2-(1-(7-bromo-2-chloroquinolin-3-yl)propan-2-yl)isoindoline-1,3-dione as a solid. MS: 429, 431 (M+1).

Step 4: To a stirred solution of 2-(1-(7-bromo-2-chloroquinolin-3-yl)propan-2-yl)isoindoline-1,3-dione (800 mg, 1.862 mmol) in tBuOH (30 ml) was added hydrazine hydrate (15 ml) at room temperature under an argon atmosphere. The reaction mixture was warmed to 100° C. and stirred for 16 h. The reaction mixture was concentrated under reduced pressure and the residue was purified by column chromatography on silica (0-40% EtOAc/DCM) to give 7-bromo-2-methyl-2,3-dihydro-1H-pyrrolo[2,3-b]quinoline as a solid. MS; 263, 265 (M+1).

Intermediate 13: (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-ol

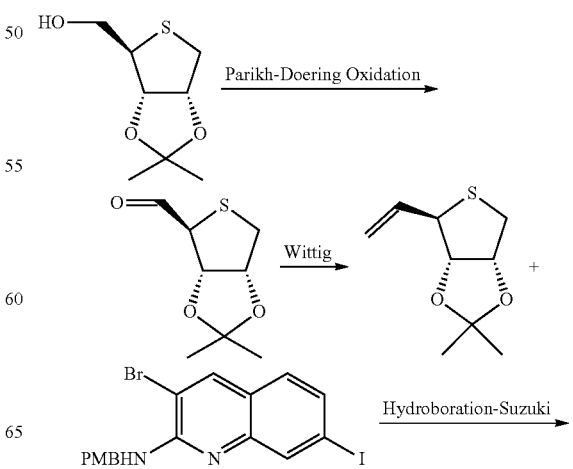

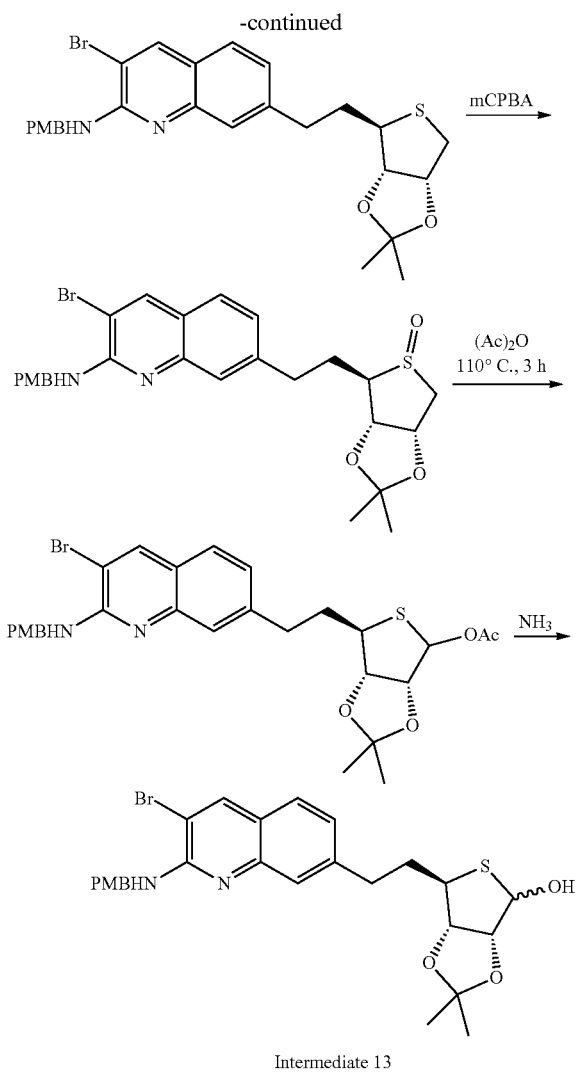

Intermediate 13

Step 1: To a stirred solution of ((3aS,4R,6aR)-2,2-dimethyltetrahydrothieno[3,4-d][1,3]dioxol-4-yl)methanol (1.50 g, 7.88 mmol) and Hunig's Base (6.9 mL, 40 mmol) in DCM (29 mL) and DMSO (7.3 mL) at 0° C. was added pyridine sulfur trioxide (6.3 g, 39 mmol). The reaction mixture was stirred at room temperature for 4 h. The reaction mixture was poured into a separatory funnel containing water, and the mixture was extracted with ether (2×). The combined organic layers were washed with water (3×), washed with brine, dried over MgSO$_4$, filtered, and concentrated under reduced pressure to afford (3aS,4S,6aR)-2,2-dimethyltetrahydrothieno[3,4-d][1,3]dioxole-4-carbaldehyde. H NMR (600 MHz, CDCl$_3$) δ 9.38 (s, 1H), 5.13 (d, J=5.5 Hz, 1H), 4.99-4.88 (m, 1H), 3.94 (s, 1H), 2.90 (d, J=13.3 Hz, 1H), 2.65 (dd, J=13.3, 4.1 Hz, 1H), 1.54 (s, 3H), 1.35 (s, 3H).

Step 2; A round bottom flask was charged with methyltriphenylphosphonium bromide (1.14 g, 3.19 mmol) and THF (20 mL). The mixture was cooled to −78° C., and then n-butyllithium (1.6 M in hexane, 20 mL, 3.19 mmol) was added dropwise under N$_2$. The solution was warmed to 0° C. and stirred under nitrogen for 35 minutes. The flask was cooled back down to −78° C., and (3aS,4S,6aR)-2,2-dimethyltetrahydrothieno[3,4-d][1,3]dioxole-4-carbaldehyde (400 mg, 2.13 mmol) was added as a solution in THF (40 mL) (2 portions). The flask was allowed to warm to room temperature and stirred overnight. The reaction was poured into a separatory funnel containing sat. NH$_4$Cl and EtOAc. The aqueous layer was extracted again with EtOAc. The combined, organic layers were washed with brine, dried over MgSO$_4$, filtered, and concentrated under reduced pressure. The residue was purified by column chromatography on silica (0-20% EtOAc/hexanes) to afford (3aS,4R,6aR)-2,2-dimethyl-4-vinyltetrahydrothieno[3,4-d][1,3]dioxole as an oil. $^1$H NMR (600 MHz, CDCl$_3$) δ 5.83 (ddd, J=17.2, 10.3, 7.1 Hz, 1H), 5.23 (dt, J=17.0, 1.2 Hz, 1H), 5.14 (dt, J=10.3, TO Hz, 1H), 4.91 (td, J=5.5, 2.1 Hz, 1H), 4.68 (dd, J=5.9, 2.5 Hz, 1H), 3.85 (d, J=8.3 Hz, 1H), 3.03 (dd, J=12.8, 5.1 Hz, 1H), 2.93 (dd, J=12.8, 2.1 Hz, 1H), 1.56 (s, 3H), 1.35 (s, 3H).

Step 3: To a vial at 0° C. was added (3aS,4R,6aR)-2,2-dimethyl-4-vinyltetrahydrothieno[3,4-d][1,3]dioxole (0.160 g, 0.859 mmol) and 9-BBN (5.15 mL, 0.5 M in THF, 2.58 mmol). The reaction mixture was stirred overnight at room temperature. The reaction was quenched with K$_3$PO$_4$ (2 M in water, 2.1 mL, 4.4 mmol), and the mixture was stirred for 30 min at room temperature. A separate vial containing 3-bromo-7-iodo-N-(4-methoxybenzyl)quinolin-2-amine (0.6 g, 1.3 mmol), PdCl$_2$(dppf)-methylene chloride complex (0.070 g, 0.086 mmol), and THF (1.5 mL) was added to the boronate. The reaction mixture was heated at 50° C. overnight. The reaction was diluted with DCM and water. The organic and aqueous layers were separated by passage through a phase separator, and the organic layer was concentrated under reduced pressure. The residue was purified by column chromatography on silica (0-30% EtOAc/hexanes) to afford 3-bromo-7-(2-((3aS,4R,6aR)-2,2-dimethyltetrahydrothieno[3,4-d][1,3]dioxol-4-yl)ethyl)-N-(4-methoxybenzyl)quinolin-2-amine. MS: 529, 531 (M+1).

Step 4: A solution of mCPBA (410 mg, 1.83 mmol) in DCM (6 mL) was added to a solution of 3-bromo-7-(2-((3aS,4R,6aR)-2,2-dimethyltetrahydrothieno[3,4-d][1,3]dioxol-4-yl)ethyl)-N-(4-methoxybenzyl)quinolin-2-amine (920 mg. 1.74 mmol) in DCM (90 mL) at −78° C. under a nitrogen atmosphere. The reaction mixture was stirred at −78° C. for 30 min. The mixture was diluted with DCM. The organic layer was washed with a 10% sodium thiosulfate, sat. NaHCO$_3$ solution, and brine. The organic layer was dried over anhydrous Na$_2$SO$_4$, filtered, and concentrated under reduced pressure. The residue was purified by column chromatography on silica (0-100% EtOAc/hexanes) to afford (3aS,4R,6aR)-4-(2-(3-bromo-2-((4-methoxybenzyl)amino)quinolin-7-yl)ethyl)-2,2-dimethyltetrahydrothieno[3,4-d][1,3]dioxole 5-oxide. MS: 545, 547 (M+1).

Step 5: Acetic anhydride (3.3 mL, 35 mmol) was added to a vial charged with (3aS,4R,6aR)-4 (2-(3-bromo-2-((4-methoxybenzyl)amino)quinolin-7-yl)ethyl)-2,2-dimethyltetrahydrothieno[3,4-d][1,3]dioxole 5-oxide (128 mg, 0.24 mmol). The reaction mixture was heated at 110° C. for 5 h. The reaction mixture was cooled to room temperature and concentrated under reduced pressure. The residue was diluted with DCM, and the organic layer was washed with sat. NaHCO$_3$ (2×), dried over Na$_2$SO$_4$, then concentrated under reduced pressure to give (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-yl acetate, which was used without further purification. MS: 587, 589 (M+1).

Step 6; (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-yl acetate (45 mg, 0.077 mmol) was dissolved in ammonia (7N in MeOH, 0.33 mL, 2.3 mmol). The reaction mixture was stirred at room temperature overnight. The mixture was concentrated under reduced pressure and the residue was purified by column chromatography on silica (0-30% EtOAc/hexanes) to give (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-ol. MS: 545, 547 (M+1).

Intermediate 14:
7-bromo-3-(difluoromethyl)quinolin-2-amine

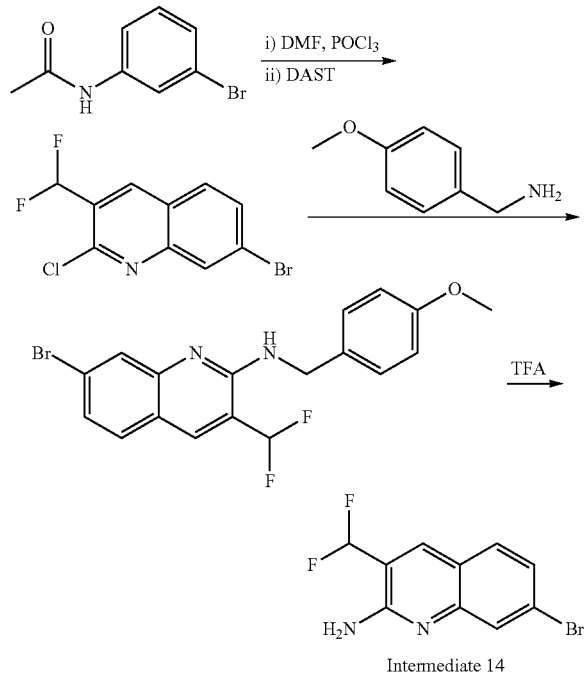

Intermediate 14

Step 1: To DMF (16 mL) was added POCl₃ (48.8 mL, 523 mmol) dropwise via cannula over 30 minutes at 0° C., and the reaction mixture was stirred for another 30 minutes at this temperature. N-(3-bromophenyl)acetamide (16 g, 75 mmol) was added to the mixture and the reaction was stirred at 80° C. for 2 h. The mixture was concentrated under reduced pressure. The residue was diluted with saturated aqueous NaHCO₃ (200 mL) and extracted with EtOAc (1000 mL). The organic phase was washed with water (600 mL) and brine (300 mL), and dried over anhydrous sodium sulfate, filtered, and the filtrate was concentrated under reduced pressure. The residue was purified by column chromatography on silica (20% EtOAc/petroleum ether) to afford 7 bromo-2-chloroquinoline-3-carbaldehyde as a solid. Then, 7-bromo-2-chloroquinoline-3-carbaldehyde (1.8 g, 6.65 mmol) was co-evaporated with toluene (5 mL) three times. To a solution of 7-bromo-2-chloroquinoline-3-carbaldehyde (1.8 g, 6.65 mmol) in DCM (27 mL) was added DAST (1.76 mL, 13.3 mmol) at 0° C., and the mixture was stirred at 50° C. for 1.5 h. The reaction was diluted with saturated aqueous NaHCO₃ (50 mL) at 0° C. and extracted with EtOAc (250 mL). The organic layer was washed with water (100 mL) and brine (100 mL), dried over anhydrous sodium sulfate, filtered, and the filtrate was concentrated under reduced pressure. The residue was purified by column chromatography on silica (30% DCM/petroleum ether) to afford 7-bromo-2-chloro-3-(difluoromethyl)quinoline as a solid. MS: 291, 293 (M+1).

Step 2: A solution of 7-bromo-2-chloro-3-(difluoromethyl)quinoline (960 mg, 3.28 mmol) and (4-methoxyphenyl)methanamine (2.14 mL, 16.4 mmol) in 1,4-dioxane (10 mL) was heated at 90° C. for 16 h. The reaction was cooled to room temperature, concentrated under reduced pressure, and the resulting residue was purified by column chromatography on silica (20% EtOAc/PE) to afford 7-bromo-3-(difluoromethyl)-N-(4-methoxybenzyl)quinolin-2-amine as a solid. MS: 393, 395 (M+1).

Step 3: A solution of 7-bromo-3-(difluoromethyl)-N-(4-methoxybenzyl)quinolin-2-amine (200 mg, 0.509 mmol) in TFA (15 mL) was stirred at 50° C. under argon for 3 h. The reaction was then diluted with saturated aqueous NaHCO₃ (100 mL) at 0° C. and extracted with EtOAc (200 mL). The organic layer was washed with water (50 mL) and brine (50 mL), dried over anhydrous sodium sulfate, filtered, and the filtrate was concentrated under reduced pressure. The residue was purified by column chromatography on silica (20% EtOAc/petroleum ether) to afford 7-bromo-3-(difluoromethyl)quinolin-2-amine as a solid. MS: 273, 275 (M+1).

EXAMPLES

Example 1: (2R,3S,4R,5R)-2-(((2-amino-3-bromoquinolin-7-yl)oxy)methyl)-5-(4-amino-7H-pyrrolo[2,3-d]pyrimidin-7-yl)tetrahydrothiophene-3,4-diol

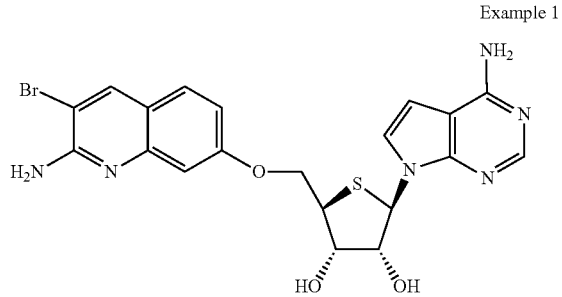 [SMILES: Nc1nc2cc(OC[C@H]3S[C@@H](n4ccc5c(N)ncnc54)[C@H](O)[C@@H]3O)ccc2cc1Br]

Example 1

Step 1: To a stirred solution of ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol (1.2 g, 3.5 mmol), 2-amino-3-bromoquinolin-7-ol (0.923 g, 3.86 mmol) and triphenylphosphine (1.84 g, 7.02 mmol) in anhydrous THF (23 mL) was added (E)-diisopropyl diazene-1,2-dicarboxylate (1.42 g, 7.02 mmol) at 0° C. The reaction was warmed to room temperature and stirred for 1.5 h. The reaction mixture was concentrated under reduced pressure, and the residue was purified by column chromatography on silica (0-60% EtOAc/petroleum ether) to give 3-bromo-7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)quinolin-2-amine. MS: 562, 564 (M+1). ¹H NMR (400 MHz, DMSO-d₆) δ 8.71 (s, 1H), 8.30 (s, 1H), 8.09 (d, J=3.9 Hz, 1H), 7.66-7.56 (m, 1H), 6.98-6.83 (m, 2H), 6.79 (d, J=3.8 Hz, 1H), 6.59 (s, 2H), 6.45 (d, J=2.5 Hz, 1H), 5.45 (dd, J=5.4, 2.6 Hz, 1H), 5.23 (d, J=5.8 Hz, 1H), 4.44-4.40 (m, 1H), 4.31 (dd, J=10.0, 6.3 Hz, 1H), 4.05 (s, 1H), 1.59 (s, 3H), 1.34 (s, 3H).

Step 2: To a stirred solution of 3-bromo-7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)quinolin-2-amine (1.6 g, 1.3 mmol) in water (12 mL) was added TFA (12 mL) at 0° C. The reaction mixture was stirred at ambient temperature for 0.5 h. The reaction mixture was neutralized with 50 mL of saturated aq. NaHCO₃ and then concentrated under reduced pressure. The residue was partitioned between EtOAc (300 mL) and water (100 mL). The precipitate was collected by filtration and then dried under reduced pressure to give (2R,3S,4R,5R)-2-(((2-amino-3-bromoquinolin-7-yl)oxy)methyl)-5-(4-chloro-7H-pyrrolo[2,3-d]pyrimidin-7-yl)tetrahydrothiophene-3,4-diol as a solid. The filtrate was separated, and the organic layer was washed with water (80 mL×2) and brine (80 mL×2). The organic phase was dried over anhydrous sodium sulfate, filtered, and the filtrate was concentrated under reduced pressure to afford (2R,3S,4R,5R)-2-(((2-amino-3-bromoquinolin-7-yl)oxy)methyl)-5-(4-chloro-7H-pyrrolo[2,3-d]pyrimidin-7-yl)tetrahydrothiophene-3,4-diol, MS: 522, 524 (M+1). $^1$H NMR (400 MHz, DMSO-d₆) δ 8.68 (s, 1H), 8.30 (s, 1H), 8.22 (d, J=3.8 Hz, 1H), 7.61 (d, J=8.8 Hz. 1H), 7.01 (d, J=2.5 Hz, 1H), 6.94 (dd, J=8.8, 2.5 Hz, 1H), 6.80 (d, J=3.8 Hz, 1H), 6.57 (s, 2H), 6.30 (d, J=6.8 Hz, 1H), 5.74 (s, 2H), 4.65-4.63 (m, 1H), 4.58-4.51 (m, 1H), 4.38-4.32 (m, 2H), 3.71-3.67 (m, 1H).

Step 3: To a stirred solution of (2R,3S,4R,5R)-2-(((2-amino-3-bromoquinolin-7-yl)oxy)methyl)-5-(4-chloro-7H-pyrrolo[2,3-d]pyrimidin-7-yl)tetrahydrothiophene-3,4-diol (310 mg, 0.593 mmol) in 1,4-dioxane (50 mL) was added ammonium hydroxide (50 mL, 0.59 mmol) in a sealed tube at ambient temperature. The reaction mixture was heated at 95° C. for 16 h. The reaction mixture was cooled to room temperature and concentrated under reduced pressure. The residue was dissolved in MeOH (5 mL) and purified by reverse-phase HPLC (0-100% acetonitrile/water with 5 mM NH₄HCO₃ modifier) to give (2R,3S,4R,5R)-2-(((2-amino-3-bromoquinolin-7-yl)oxy)methyl)-5-(4-amino-7H-pyrrolo[2,3-d]pyrimidin-7-yl)tetrahydrothiophene-3,4-diol. MS: 503, 505 (M+1). $^1$H NMR (300 MHz, DMSO-d₆) δ 8.31 (s, 1H), 8.09 (s, 1H), 7.63-7.58 (m, 2H), 7.05-6.92 (m, 4H), 6.65-6.59 (m, 3H), 6.19 (d, J=6.3 Hz, 1H), 5.56-5.52 (m, 2H), 4.56-4.51 (m, 2H), 4.37-4.30 (m, 2H), 3.68-3.63 (m, 1H).

Compounds in Table 1 were synthesized in an analogous fashion as described in the steps of Example 1. The starting materials were commercially acquired, synthesized as reported herein, or synthesized through known routes reported in the literature.

TABLE 1

| Example | Structure | Compound Name | Exact Mass [M + 1] |
|---|---|---|---|
| 2 | 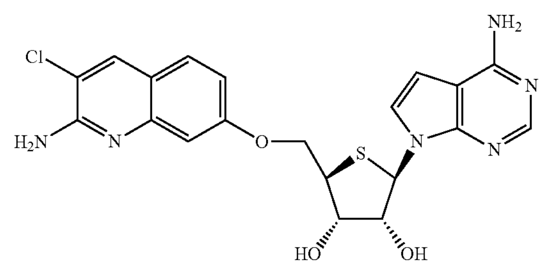 [SMILES: Nc1nc2cc(OC[C@H]3S[C@@H](n4ccc5c(N)ncnc54)[C@H](O)[C@@H]3O)ccc2cc1Cl] | 7-[5-O-(2-amino-3-chloroquinolin-7-yl)-4-thio-beta-D-ribofuranosyl]-7H-pyrrolo[2,3-d]pyrimidin-4-amine | 459 |
| 3 | 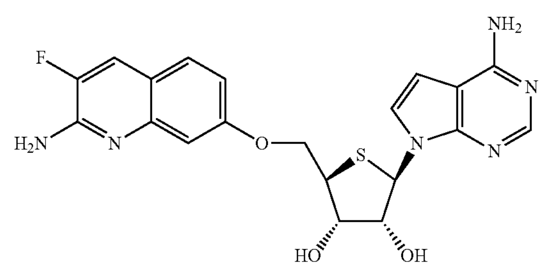 [SMILES: Nc1nc2cc(OC[C@H]3S[C@@H](n4ccc5c(N)ncnc54)[C@H](O)[C@@H]3O)ccc2cc1F] | 7-[5-O-(2-amino-3-fluoroquinolin-7-yl)-4-thio-beta-D-ribofuranosyl]-7H-pyrrolo[2,3-d]pyrimidin-4-amine | 443 |
| 4 | 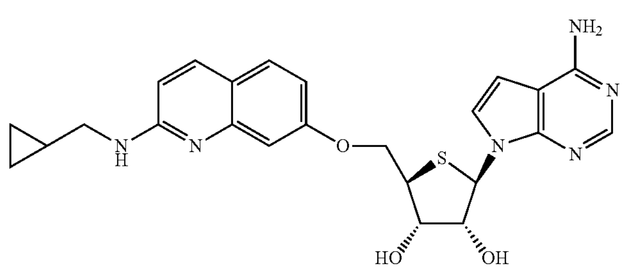 [SMILES: Nc1ncnc2c1ccn2[C@@H]1S[C@H](COc2ccc3ccc(NCC4CC4)nc3c2)[C@@H](O)[C@H]1O] | 7-(5-O-{2-[(cyclopropylmethyl)amino]quinolin-7-yl}-4-thio-beta-D-ribofuranosyl)-7H-pyrrolo[2,3-d]pyrimidin-4-amine | 479 |

Example 5: (2R,3S,4R,5R)-2-(((2-amino-3-chloro-quinolin-7-yl)oxy)methyl-5-(4-chloro-7H-pyrrolo[2,3-d]pyrimidin-7-yl)tetrahydrothiophene-3,4-diol

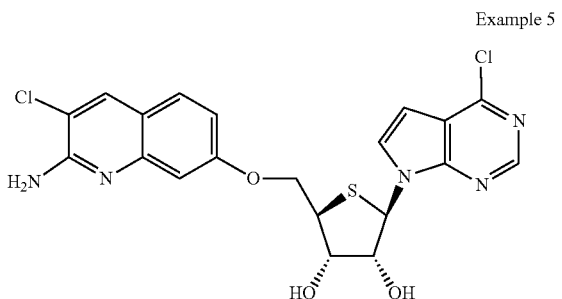 [SMILES: CN(C)c1nc2cc(OC[C@H]3S[C@@H](n4ccc5c(Cl)ncnc54)[C@H](O)[C@@H]3O)ccc2cc1Cl]

Example 5

Step 1: To a stirred solution of ((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methanol (102 mg, 0.3 mmol), 2-amino-3-chloroquinolin-7-ol (58.2 mg, 0.3 mmol) and triphenylphosphine (157 mg, 0.6 mmol) in anhydrous THF (4 mL) was added (E)-diisopropyl diazene-1,2-dicarboxylate (121 mg, 0.6 mmol) dropwise at 0° C. The reaction was warmed to room temperature and stirred at room temperature for 1.5 h. The reaction mixture was concentrated under reduced pressure and purified by Prep-TLC (developed by EtOAc:petroleum ether=1:1, v:v) to give 3-chloro-7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)quinolin-2-amine. MS: 518 (M+1). $^1$H NMR (400 MHz, Methanol-$d_4$) δ 8.63 (s, 1H), 8.05 (s, 1H), 7.94 (d, J=3.8 Hz, 1H), 7.57 (d, J=8.9 Hz, 1H), 7.00 (d, J=2.5 Hz, 1H), 6.94-6.91 (m, 1H), 6.74 (d, J=3.8 Hz, 1H), 6.49-6.47 (m, 1H), 5.42 (dd, J=5.6, 2.6 Hz, 1H), 5.25 (dd, J=5.5, 2.2 Hz, 1H), 4.48-4.44 (m, 1H), 4.36-4.32 (m, 1H), 4.22-4.06 (m, 1H), 1.67 (s, 3H), 1.40 (s, 3H).

Step 2: To a stirred solution of 3-chloro-7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)quinolin-2-amine (50 mg, 0.092 mmol) in water (2 mL) was added TFA (2 mL) at 0° C. The resulting mixture was warmed gradually to ambient temperature and stirred at ambient temperature for 1 h. The mixture was concentrated under reduced pressure and the residue was purified by reverse phase HPLC (ACM/water with 0.05% TFA modifier). The combined fractions were washed with 10% aqueous NH$_3$·H$_2$O. The organic layer was concentrated under reduced pressure and the residue was purified by reverse-phase HPLC (0-100% acetonitrile/water with 5 mM NH$_4$HCO$_3$ modifier) to give (2R,3S,4R,5R)-2-(((2-amino-3-chloroquinolin-7-yl)oxy)methyl)-5-(4-chloro-7H-pyrrolo[2,3-d]pyrimidin-7-yl)tetrahydrothiophene-3,4-diol. MS: 478 (M+1). $^1$H NMR (400 MHz, DMSO-$d_6$): δ 8.68 (s, 1H), 8.21 (d, J=3.8 Hz, 1H), 8.13 (s, 1H), 7.61 (d, J=8.8 Hz, 1H), 7.03 (d, J=1.8 Hz, 1H), 6.95 (dd, J=8.8, 2.4 Hz, 1H), 6.80 (d, J=4.0 Hz, 1H), 6.64 (s, 2H), 6.30 (d, J=6.8 Hz, 1H), 5.65-5.60 (m, 2H), 4.65-4.64 (m, 1H), 4.56-4.53 (m, 1H), 4.38-4.32 (m, 2H), 3.69-3.68 (m, 1H).

Example 6: (2R,3S,4R,5R)-2-(((2-amino-3-bromo-quinolin-7-yl)oxy)methyl)-5-(4-chloro-7H-pyrrolo[2,3-d]pyrimidin-7-yl)-2-methyltetrahydrothiophene-3,4-diol and Example 7: (2R,3R,4R,5R)-2-(((2-amino-3-bromo-quinolin-7-yl)oxy)methyl)-5-(4-amino-7H-pyrrolo[2,3-d]pyrimidin-7-yl)-2-methyltetrahydrothiophene-3,4-diol Example 6

Example 7

Step 1: To a stirred solution of ((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methanol (160 mg, 0.450 mmol), 2-amino-3-bromoquinolin-7-ol (118 mg, 0.495 mmol) and triphenylphosphine (236 mg, 0.899 mmol) in anhydrous THF (5 mL) was added (E)-diisopropyl diazene-1,2-dicarboxylate (182 mg, 0.899 mmol) dropwise at 0° C., and then the reaction solution was warmed to room temperature and stirred for 1.5 h. The reaction mixture was concentrated under reduced pressure, and the residue was purified by prep-TLC (developed by MeOH:DCM=20:1, v/v) followed by reverse-phase HPLC (0-100% acetonitrile/5 mM aq. NH$_4$HCO$_3$) to afford 3-bromo-7-(((3 aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methoxy)quinolin-2-amine. MS: 576, 578 (M+1). $^1$H NMR (300 MHz, DMSO-$d_6$) δ 8.71 (s, 1H), 8.31 (s, 1H), 8.12 (d, J=3.8 Hz, 1H), 7.60 (d, J=8.8 Hz, 1H), 6.97 (d, J=2.3 Hz, 1H), 6.89 (dd, J=8.9, 2.4 Hz, 1H), 6.74 (d, J=3.8 Hz, 1H), 6.59 (s, 2H), 6.47 (d, J=3.5 Hz, 1H), 5.57-5.54 (m, 1H), 4.90 (d, J=5.2 Hz, 1H), 4.36 (d, J=9.7 Hz, 1H), 4.24 (d, J=9.8 Hz, 1H), 1.65 (s, 3H), 1.60 (s, 3H), 1.35 (s, 3H).

Step 2; A solution of 3-bromo-7-(((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)methoxy)quinolin-2-amine (13 mg, 0.022 mmol) in water (0.5 mL) and TFA (0.5 mL) was stirred at room temperature for 0.5 h. The mixture was co-evaporated with toluene (2 mL×3), and the residue was purified by reverse-phase HPLC (0-100% acetonitrile/5 mM aq. NH$_4$HCO$_3$) to afford (2R,3S,4R,5R)-2-(((2-amino-3-bromoquinolin-7-yl)oxy)methyl)-5-(4- chloro-7H-pyrrolo[2,3-d]pyrimidin-7-yl)-2-methyltetrahydrothiophene-3,4-diol. MS: 536, 538 (M+1). ¹H NMR (300 MHz, DMSO-d₆): δ 8.66 (s, 1H), 8.30 (s, 1H), 8.24 (d, J=3.9 Hz, 1H), 7.60 (d, J=8.7 Hz, 1H), 7.05 (d, J=2.1 Hz, 1H), 6.95 (d, J=2.4 Hz, 1H), 6.79 (d, J=3.6 Hz, 1H), 6.55 (s, 2H), 6.39 (d, J=8.4 Hz, 1H), 5.68 (d, J=4.8 Hz, 1H), 5.51 (d, J=6.9 Hz, 1H), 5.00-4.96 (m, 1H), 4.55 (d, J=10.5 Hz, 1H), 4.19-4.16 (m, 2H), 1.51 (s, 3H).

Step 3: (2R,3S,4R,5R)-2-(((2-amino-3-bromoquinolin-7-yl)oxy)methyl)-5-(4-chloro-7H-pyrrolo[2,3-d]pyrimidin-7-yl)-2-methyltetrahydrothiophene-3,4-diol (10 mg, 0.015 mmol) was dissolved, in dioxane (6 mL) and aqueous ammonia (6 mL) in a sealed tube. The reaction mixture was stirred at 95° C. for 7 h. The mixture was cooled to room temperature and concentrated under reduced pressure. The residue was purified by reverse-phase HPLC (0-10014 acetonitrile/5 mM aq. NH₄HCO₃) to afford (2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrothiophene-3,4-diol. MS: 517, 519 (M+1). ¹H NMR (400 MHz, DMSO-d₆): δ 8.31 (s, 1H), 8.07 (s, 1H), 7.63-7.59 (m, 2H), 7.04-6.94 (m, 4H), 6.62 (s, 1H), 6.56 (br s, 2H), 6.28 (d, J=8.0 Hz, 1H), 5.55 (d, J=4.8 Hz, 1H), 5.35 (d, J=1.2 Hz, 1H), 4.96-4.93 (m, 1H), 4.52 (d, J=10.0 Hz, 1H), 4.15 (d, J=5.6 Hz, 2H), 1.50 (s, 3H).

Example 8: (2R,3S,4R,5R)-2-(((2-((cyclopropylmethyl)amino)quinolin-7-yl)oxy)methyl)-5-(4-methoxy-7H-pyrrolo[2,3-d]pyrimidin-7-yl)tetrahydrothiophene-3,4-diol

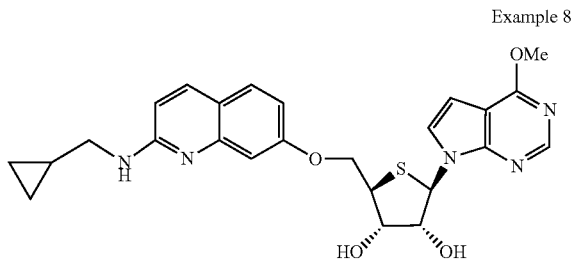

Example 8

Step 1: To a solution of ((3aS,4R,6R,6aR)-6-(4-chloro-7H-pyrrolo[2,3-d]pyrimidin-7yl)-2,2-dimethyltetrahydrothieno[3,4-d][1,3]dioxol-4-yl)methanol (150 mg, 0.44 mmol), 2-((cyclopropylmethyl)amino)quinolin-7-ol (103 mg, 0.48 mmol) and triphenylphosphine (345 mg, 1.32 mmol) in THF (4 mL) was added DIAD (0.21 mL, 1.1 mmol) dropwise at 0° C. under an atmosphere of argon. The reaction was stirred for 2 h at room temperature under an atmosphere of argon. The resulting solution was purified directly by prep-TLC (developed by 50% EtOAc in petroleum ether) to afford 7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)-N-(cyclopropylmethyl)quinolin 2-amine. MS: 538 (M+1). ¹H NMR (300 MHz, DMSO-d₆) δ 8.72 (s, 1H), 8.09 (d, J=3.9 Hz, 1H), 7.76 (d, J=9.0 Hz, 1H), 7.52 (d, J=8.7 Hz, 1H), 7.11-7.05 (m, 2H), 6.79 (d, J=4.2 Hz, 2H), 6.65 (d, J=9.0 Hz, 1H), 6.46 (d, J=2.7 Hz, 1H), 5.47-5.41 (m, 1H), 5.26-5.17 (m, 1H), 4.50-4.37 (m, 1H), 4.37-4.25 (m, 1H), 4.08-3.89 (m, 1H), 3.27 (t, J=6.1 Hz, 2H), 1.59 (s, 3H), 1.33 (s, 3H), 0.90-0.81 (m, 1H), 0.53-0.44 (m, 2H), 0.31-0.23 (m, 2H).

Step 2: To a stirred solution of 7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)-N-(cyclopropylmethyl)quinolin-2-amine (46 mg, 0.085 mmol) in 2 ml, of MeOH was added sodium methoxide (2 M in MeOH, 0.171 mL, 0.342 mmol) at room temperature. The mixture was stirred at room temperature for 16 h. The reaction was concentrated under reduced pressure and the residue was purified by reverse-phase HPLC (0-100% acetonitrile/5 mM aq. NH₄HCO₃) to afford N-(cyclopropylmethyl)-7-(((3aS,4R,6R,6aR)-6-(4-methoxy-7H-pyrrolo[2,3-d]pyrimidin-7-yl)-2,2-dimethyltetrahydrothieno[3,4-d][1,3]dioxol-4-yl)methoxy)-N-amine. MS: 534 (M+1). ¹H NMR (400 MHz, DMSO-d₆) δ 8.49 (d, J=1.6 Hz, 1H), 7.75 (d, J=9.2 Hz, 2H), 7.51 (d, J=8.7 Hz, 1H), 7.06 (s, 1H), 6.95 (s, 1H), 6.88-6.72 (m, 1H), 6.64 (dd, J=6.6, 3.3 Hz, 2H), 6.44-6.43 (m, 1H), 5.42 (t, J=3.9 Hz, 1H), 5.21 (d, J=5.4 Hz, 1H), 4.52-4.39 (m, 1H), 4.28 (t, J=8.5 Hz, 1H), 4.06 (d, J=1.6 Hz, 3H), 4.00 (t, J=7.0 Hz, 1H), 3.27 (t, J=6.2 Hz, 2H), 1.34 (s, 3H), 1.25 (s, 3H), 1.11 (d, J=7.7 Hz, 1H), 0.48 (d, J=7.8 Hz, 2H), 0.27 (d, J=5.0 Hz, 2H).

Step 3: N-(cyclopropylmethyl-7-(((3aS,4R,6R,6aR)-6-(4-methoxy-7H-pyrrolo[2,3-d]pyrimidin-7-yl)-2,2-dimethyltetrahydrothieno[3,4-d][1,3]dioxol-4-yl)methoxy)quinolin-2-amine (35 mg, 0.066 mmol) was dissolved in a mixture of TFA (1 mL) and water (1 mL) at 0° C. under an argon atmosphere. The resulting mixture was warmed to room temperature and stirred for 2 h. The mixture was co-evaporated with toluene (3 mL×3), and the residue was purified by reverse-phase HPLC (0-100% acetonitrile/5 mM aq. NH₄HCO₃) to afford (2R,3S,4R,5R)-2-(((2-((cyclopropylmethyl)amino)quinolin-7-yl)oxy)methyl)-5-(4-methoxy-7H-pyrrolo[2,3-d]pyrimidin-7-yl)tetrahydrothiophene-3,4-diol. MS: 494 (M+1). ¹H NMR (400 MHz, DMSO-d₆): δ 8.45 (s, 1H), 7.88 (d, J=3.6 Hz, 1H), 7.74 (d, J=8.8 Hz, 1H), 7.51 (d, J=8.8 Hz, 1H), 7.05-7.02 (m, 2H), 6.81 (dd, J=8.8, 2.4 Hz, 1H), 6.64-6.62 (m, 2H), 6.28 (d, J=6.8 Hz, 1H), 5.56-5.55 (m, 2H), 4.61 (d, J=3.2 Hz, 1H), 4.54-4.50 (m, 1H), 4.35-4.31 (m, 2H), 4.05 (s, 3H), 3.67-3.65 (m, 1H), 3.28-3.25 (m, 2H), 1.13-1.11 (m, 1H), 0.47 (d, J=8.0 Hz, 2H), 0.25 (d, J=4.8 Hz, 2H).

Example 9: (2R,3S,4R,5R)-2-(((2-((cyclopropylmethyl)amino)quinolin-7-yl)oxy)methyl)-5-(4-methyl-7H-pyrrolo[2,3-d]pyrimidin-7-yl)tetrahydrothiophene-3,4-diol Example 9

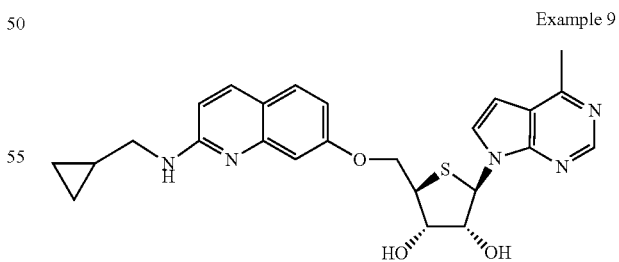

Step 1: To a mixture of 7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)-N-(cyclopropylmethyl)quinolin-2-amine (45 mg, 0.084 mmol) and tetrakis(triphenylphosphine)palladium(0) (4.83 mg, 4.18 μmol) in anhydrous THF (5 mL) was added trimethyl aluminum (2 M in toluene, 0.084 mL, 0.168 mmol) at room temperature under an argon atmosphere. The mixture was then stirred at 100° C. for 2 h. After cooling, the mixture was poured into aq. HCl (1 M, 10 mL). The mixture was extracted with DCM (30 mL×2). The combined organic layers were washed with water (25 mL), saturated aq. NaHCO$_3$ (25 mL), dried over anhydrous sodium sulfate, filtered, and the filtrate was concentrated under reduced pressure. The residue was purified by column chromatography on silica (10-50% EtOAc/PE) to give N-(cyclopropylmethyl)-7-(((3aS,4R,6R,6aR)-2,2-dimethyl-6-(4-methyl-7H-pyrrolo[2,3-d]pyrimidin-7-yl)tetrahydrothieno[3,4-d][1,3]dioxol-4-yl)methoxy)quinolin-2-amine as a solid. MS: 518 (M+1).

Step 2: N-(cyclopropylmethyl)-7-(((3aS,4R,6R,6aR)-2,2-dimethyl-6-(4-methyl-7H-pyrrolo[2,3-d]pyrimidin-7-yl)tetrahydrothieno[3,4-d][1,3]dioxol-4-yl)methoxy)quinolin-2-amine (26 mg, 0.050 mmol) was dissolved in TEA (50% in water, 4 mL) and stirred at room temperature for 1 h. The reaction was quenched with saturated aq. NaHCO$_3$ (30 mL) and the mixture was extracted with EtOAc (60 mL). The organic layer was washed with brine (50 mL), dried over anhydrous sodium sulfate, filtered, and the filtrate was concentrated under reduced pressure. The residue was purified by reverse phase HPLC (ACN/water with 10 mM aq. NH$_4$HCO$_3$ modifier) to give (2R,3S,4R,5R)-2-(((2-((cyclopropylmethyl)amino)quinolin-7-yl)oxy)methyl)-5-(4-methyl-7H-pyrrolo[2,3-d]pyrimidin-7-yl)tetrahydrothiophene-3,4-diol as a solid. MS: 478 (M+1). $^1$H NMR (400 MHz, DMSO-d$_6$) δ 8.67 (s, 1H), 8.01 (d, J=4.0 Hz, 1H), 7.74 (d, J=8.8 Hz, 1H), 7.51 (d, J=8.8 Hz, 1H), 7.03-7.02 (m, 2H), 6.82-6.79 (m, 2H), 6.63 (d, J=8.8 Hz, 1H), 6.31 (d, J=7.2 Hz, 1H), 5.55-5.54 (m, 2H), 4.61 (dd, J=10.0, 6.8 Hz, 1H), 4.54 (dd, J=10.0, 6.8 Hz, 1H), 4.35-4.32 (m, 2H), 3.68-3.66 (m, 1H), 3.29-3.26 (m, 2H), 2.65 (s, 3H), 1.14-1.10 (m, 1H), 0.50-0.45 (m, 2H), 0.28-0.24 (m, 2H).

Example 10: (2R,3S,4R,5R)-2-(((2-aminoquinolin-7-yl)oxy)methyl)-5-(4-methoxy-7H-pyrrolo[2,3-d]pyrimidin-7yl)tetrahydrothiophene-3,4-diol

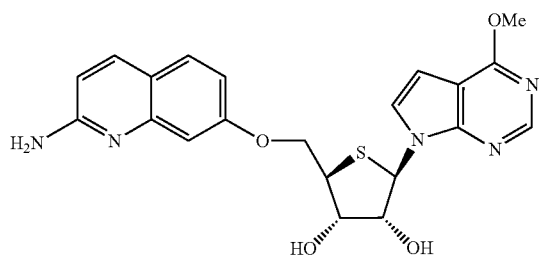

Example 10

Step 1: To a stirred solution of 3-bromo-7-(((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)methoxy)quinolin-2-amine (40 mg, 0.071 mmol) in MeOH (2 mL) and THF (2 mL) was added sodium methanolate (23 mg, 0.43 mmol) at 0° C. The resulting solution was warmed to 65° C. and stirred for 1.5 h. The reaction was cooled to room temperature, and the mixture was neutralized to pH 7 with 1 M aq. HCl. The mixture was concentrated under reduced pressure, and the residue was partitioned between ethyl acetate (20 mL) and water (20 mL). The organic layer was concentrated under reduced pressure to afford 3-bromo-7-(((3aS,4R,6R,6aR)-6-(4-methoxy-7H-pyrrolo[2,3-d]pyrimidin-7-yl)-2,2-dimethyltetrahydrothieno[3,4-d][1,3]dioxol-4-yl)methoxy)quinolin-2 amine as a solid, winch was directly used in the next step without further purification. MS: 558, 560 (M+1).

Step 2: A flask was charged with 3-bromo-7-(((3aS,4R,6R,6aR)-6-(4-methoxy-7H-pyrrolo[2,3-d]pyrimidin-7-yl)-2,2-dimethyltetrahydrothieno[3,4-d][1,3]dioxol-4yl)methoxy)quinolin-2-amine (40 mg, 0.072 mmol), water (2 mL) and TFA (2 mL) at 0° C., and the resulting solution was then warmed to 25° C. and stirred for 1.5 h. The mixture was concentrated under reduced pressure, and the residue was co-evaporated with toluene (2 mL×3). The residue was purified by reverse phase HPLC (ACN/water with 10 mM aq. NH$_4$HCO$_3$ modifier) to give (2R,3S,4R,5R)-2-(((2-amino-3-bromoquinolin-7-yl)oxy)methyl)-5-(4-methoxy-7H-pyrrolo[2,3-d]pyrimidin-7-yl)tetrahydrothiophene-3,4-diol as a solid. MS: 518, 520 (M+1). $^1$H-NMR (400 MHz, DMSO-d$_6$) δ 8.45 (s, 1H), 8.29 (s, 1H), 7.86 (d, J=3.6 Hz, 1H), 7.61 (d, J=8.8 Hz, 1H), 7.00 (d, J=1.6 Hz, 1H), 6.93 (dd, J=2.4, 8.8 Hz, 1H), 6.63 (d, J=3.6 Hz, 1H), 6.54 (br s, 2H), 6.28 (d, J=6.8 Hz, 1H), 5.58-5.55 (m, 2H), 4.62-4.51 (m, 2H), 4.36-4.31 (m, 2H), 4.05 (s, 3H), 3.67-3.66 (m, 1H).

Step 3: To a solution of (2R,3S,4R,5R)-2-(((2-amino-3-bromoquinolin-7-yl)oxy)methyl)-5-(4-methoxy-7H-pyrrolo[2,3-d]pyrimidin-7-yl)tetrahydrothiophene[3,4-d]diol (30 mg, 0.058 mmol) in MeOH (8 mL) and dioxane (32 mL) was added Pd(OH)$_2$/C (20 wt %, 8.8 mg, 0.0.58 mmol) and triethylamine (5.86 mg, 0.058 mmol). The suspension was degassed under vacuum and purged with H$_2$ several times, and then it was stirred under 1.2 atm of H$_2$ for 30 min at 25° C. The reaction mixture was filtered, and the filtrate was concentrated under reduced pressure. The residue was purified by reverse phase HPLC (ACN/water with 10 mM aq. NH$_4$HCO$_3$ modifier) to give (2R,3S,4R,5R)-2-(((2-aminoquinolin-7-yl)oxy)methyl)-5-(4-methoxy-7H-pyrrolo[2,3-d]pyrimidin-7-yl)tetrahydrothiophene-3,4-diol as a solid. MS: 440 (M+1). $^1$H-NMR (400 MHz, DMSO-d$_6$) δ 8.45 (s, 1H), 7.86 (d, J=2.8 Hz, 1H), 7.79 (d, J=8.8 Hz, 1H), 7.54 (d, J=8.8 Hz, 1H), 6.97 (s, 1H), 6.85 (d, J=8.4 Hz, 1H), 6.63-6.59 (m, 2H), 6.32-6.27 (m, 3H), 5.58-5.54 (m, 2H), 4.61-4.59 (m, 1H), 4.51 (t, J=10.0 Hz, 1H), 4.34-4.30 (m, 2H), 4.05 (s, 3H), 3.68-3.66 (m, 1H).

Example 11: (2R,3R,4S,5R)-2-(4-amino-7H-pyrrolo[2,3-d]pyrimidin-7-yl)-5-(((2-aminoquinolin-7-yl)oxy)methyl)tetrahydrothiophene-3,4-diol

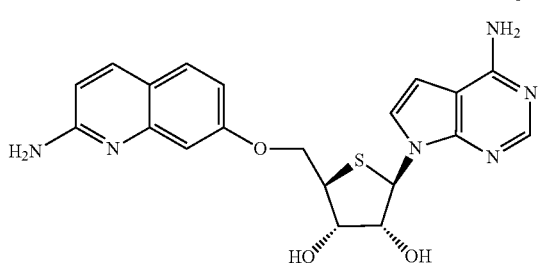

Example 11

To a solution of (2R,3S,4R,5R)-2-(((2-amino-3-bromoquinolin-7-yl)oxy)methyl)-5-(4-amino-7H-pyrrolo[2,3-d]pyrimidin-7-yl)tetrahydrothiophene-3,4-diol (60 mg, 0.119 mmol) in MeOH (6 mL) was added Pd(OH)$_2$/C (67.0 mg, 0.477 mmol, 20 wt %) and triethylamine (12 mg, 0.119 mmol). The mixture was stirred at 25° C. for 30 mm under a hydrogen atmosphere (1.2 atm). The reaction mixture was filtered, and the filtrate was concentrated under reduced pressure. The residue was purified by Prep-TLC with DCM/MeOH (v:v, 3/1) followed by reverse-phase HPLC (0-100% acetonitrile/5 mM aq. NH$_4$HCO$_3$) to give (2R,3R,4S,5R)-2-(4-amino-7H-pyrrolo[2,3-d]pyrimidin-7-yl)-5-(((2-aminoquinolin-7-yl)oxy)methyl)tetrahydrothiophene-3,4-diol. MS: 425 (M+1). $^1$H NMR (400 MHz, DMSO-d$_6$) δ 8.07 (s, 1H), 7.79 (d, J=8.8 Hz, 1H), 7.57-7.53 (m, 2H), 7.02 (br s, 2H), 6.95 (d, J=2.0 Hz, 1H), 6.84 (dd, J=8.8, 2.4 Hz, 1H), 6.63-6.58 (m, 2H), 6.33 (br s, 2H), 6.17 (d, J=6 4 Hz, 1H), 5.51 (dd, J=12.0, 6.0 Hz, 2H), 4.51-4.49 (m, 2H), 4.30-4.28 (m, 2H), 3.70-3.62 (m, 1H).

Example 12: (2R,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol

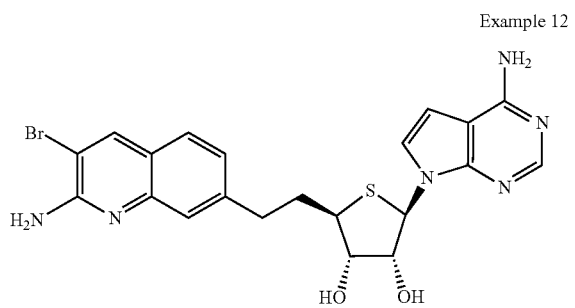 [SMILES: Nc1nc2cc(CC[C@H]3S[C@@H](n4ccc5c(N)ncnc54)[C@H](O)[C@@H]3O)ccc2cc1Br]

Example 12

Step 1: To a flask containing 4-chloro-7-((3aR,4R,6R,6aS)-2,2-dimethyl-6-vinyltetrahydrothieno[3,4-d][1,3]dioxol-4-yl)-7H-pyrrolo[2,3-d]pyrimidine (200 mg, 0.592 mmol) was added 9-BBN (3.55 mL, 0.5 M in THF, 1.78 mmol) at 0° C. The mixture was stirred at room temperature overnight. The reaction mixture was quenched with K$_3$PO$_4$ (1.48 mL, 2 M in water, 2.96 mmol) and stirred at room temperature for 30 min. Separately, 3-bromo-7-iodo-N-(4-methoxybenzyl)quinolin-2-amine (0.417 g, 0.888 mmol), Pd(dppf)C$_{1-2}$—CH$_2$C$_{1-2}$ (0.058 g, 0.071 mmol), and THF (2.5 mL) were mixed together. The resultant suspension was added to the boronate via syringe, and the reaction mixture was heated to 50° C. for 8 h. The reaction mixture was diluted with DCM and water. The organic layer was washed with brine, dried over MgSO$_4$, filtered, and concentrated under reduced pressure. The residue was purified by column chromatography on silica (0-20% EA/hexanes) to give 3-bromo-7-(2-((3aS,4R,6R,6aR)-6-(4 chloro-7H-pyrrolo[2,3-d]pyrimidin-7-yl)-2,2-dimethyltetrahydrothieno[3,4-d][1,3]dioxol-4-yl)ethyl)-N-(4-methoxybenzyl)quinolin-2-amine as a solid. MS: 680, 682 (M+1).

Step 2: A mixture of 3-bromo-7-(2-((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)ethyl)-N-(4-methoxybenzyl)quinolin-2-amine (183 mg, 0.269 mmol) and ammonium hydroxide in methanol (10 mL, 70.0 mmol) was heated in micro wave reactor at 135° C. for 4 h. The mixture was concentrated under reduced pressure to give crude 7-(2-((3aS,4R,6R,6aR)-6-(4-amino-7H-pyrrolo[2,3-d]pyrimidin-7-yl)-2,2-dimethyltetrahydrothieno[3,4-d][1,3]dioxol-4-yl)ethyl)-3-bromo-N-(4-methoxybenzyl) quinolin-2-amine, which was carried to the next step without further purification. MS: 661, 663 (M+1).

Step 3: TFA (424 μL, 5.53 mmol) was added to 7-(2-((3aS,4R,6R,6aR)-6-(4-amino-7H-pyrrolo[2,3-d]pyrimidin-7-yl)-2,2-dimethyltetrahydrothieno[3,4-d][1,3]dioxol-4-yl)ethyl-3-bromo-N-(4-methoxybenzyl)quinolin-2-amine (180 mg, 0.27 mmol), and the mixture was stirred at room temperature overnight. The mixture was concentrated under reduced pressure and the residue was purified by reverse phase HPLC (ACN/water with 0.1% TFA modifier) to give (2R,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol as TFA salt MS: 501, 503 (M+1). $^1$H NMR (600 MHz, DMSO-d$_6$) δ 8.34 (s, 1H), 8.07 (s, 1H), 7.61 (d, J=8.2 Hz, 1H), 7.44 (d, J=3.6 Hz, 1H), 7.33 (s, 1H), 7.13 (dd, J=8.2, 1.5 Hz, 1H), 7.01 (s, 2H), 6.63 (d, J=3.6 Hz, 1H), 6.59 (s, 2H), 6.11 (d, J=5.5 Hz, 1H), 5.42 (d, J=6.0 Hz, 1H), 5.25 (d, J=5.1 Hz, 1H), 4.40-4.34 (m, 1H), 4.07-4.01 (m, 1H), 3.22-3.15 (m, 1H), 2.89-2.82 (m, 1H), 2.75-2.66 (m, 1H), 2.36-2.28 (m, 1H), 2.09-2.00 (m, 1H).

Example 13: (2S,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol

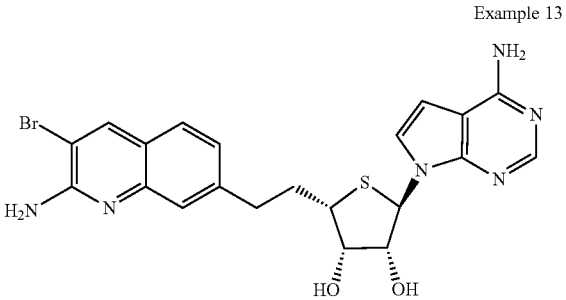 [SMILES: Nc1nc2cc(CC[C@@H]3S[C@@H](n4ccc5c(N)ncnc54)[C@H](O)[C@@H]3O)ccc2cc1Br]

Example 13

Example 13 (TFA salt) was made in an analogous way as Example 12, but starting with 4-chloro-7-((3aR,4R,6S,6aS)-2,2-dimethyl-6-vinyltetrahydrothieno[3,4-d][1,3]dioxol-4-yl)-7H-pyrrolo[2,3-d]pyrimidine to afford (2S,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol. MS; 501, 503 (M+1). H NMR (600 MHz, DMSO-d$_6$) δ 8.58 (s, 1H), 8.37 (s, 1H), 7.83 (d, J=3.6 Hz, 1H), 7.71 (d, J=8.2 Hz, 1H), 7.41 (s, 1H), 7.24 (d, J=7.6 Hz, 1H), 6.97 (d, J=3.6 Hz, 1H), 6.22 (d, J=8.9 Hz, 1H), 5.15-4.84 (m, 3H), 4.62-4.58 (m, 1H), 4.18-4.16 (m, 1H), 3.85-3.82 (m, 1H), 2.80-2.69 (m, 2H), 2 18-2.10 (m, 1H), 1.93-1.86 (m, 1H).

Example 14: (2R,3R,4S,5R)-2-(4-amino-7H-pyrrolo[2,3-d]pyrimidin-7-yl)-5-(2-(2-aminoquinolin-7-yl)ethyl)tetrahydrothiophene-3,4-diol TFA salt Example 15: (2R,3R,4S,5S)-2-(4-amino-7H-pyrrolo[2,3-d]pyrimidin-7-yl)-5-(2-(2-aminoquinolin-7-yl)ethyl)tetrahydrothiophene-3,4-diol Example 14

Example 15

(2R,3S,5R)-2-(2-(2-amino-3-bromoquinolin-7-yl)ethyl)-5-(4-amino-7H-pyrrolo[2,3d]pyrimidin 7-yl)tetrahydrothiophene-3,4-diol (made in an analogous way as Example 12, but starting with 4-chloro-7-((3aR,4R,6aS)-2,2-dimethyl-6-vinyltetrahydrothieno[3,4-d][1,3]dioxol-4-yl)-7H-pyrrolo [2,3d]pyrimidine) (55 mg, 0.110 mmol) was suspended in MeOH (5 mL). The mixture was purged with nitrogen 3 times, Pd(OH)$_2$/C (2 mg, 0.014 mmol) was added, and the reaction mixture was purged with hydrogen 3 times. The reaction mixture was stirred and kept under a hydrogen balloon at room temperature overnight. The reaction mixture was filtered through Celite and the filtrate was concentrated under reduced pressure. The residue was purified by reverse phase HPLC (ACN/water with 0.1% TFA modifier). Followed by SFC (OJ-H column, 25%/75% MeOH w/0.25% DMEA/CO$_2$) to give two isomers:

(2R,3R,4S,5R)-2-(4-amino-7-pyrrolo[2,3-d]pyrimidin-7-yl)-5-(2-(2-aminoquinolin-7-yl)ethyl)tetrahydrothiophene-3,4-diol, TFA salt (Peak 1, first eluting) MS: 423 (M+1). $^1$H NMR (600 MHz, DMSO-d$_6$) δ 8.31 (d, J=9.2 Hz, 1H), 8.14 (s, 1H), 7.85 (d, J=8.1 Hz, 1H), 7.52-7.50 (m, 1H), 7.47 (s, 1H), 7.38 (d, J=8.0 Hz, 1H), 7.00 (d, J=9.2 Hz, 1H), 6.71 (d, J=3.5 Hz, 1H), 6.11 (d, J=5 5 Hz, 1H), 5.55-5.51 (m, 1H), 5.36-5.31 (m, 1H), 4.41-4.37 (m, 1H), 4.05-4.08 (m, 1H), 3.21-3.16 (m, 1H), 2.95-2.89 (m, 1H), 2.82-2.75 (m, 1H), 2.37-2.29 (m, 1H), 2.11-2.03 (m, 1H).

and (2R,3R,4S,5S)-2-(4-amino-7-pyrrolo[2,3-d]pyrimidin-7-yl)-5-(2-(2-aminoquinolin-7-yl)ethyl)tetrahydrothiophene-3,4-diol (Peak 2, second eluting) MS: 423 (M+1). $^1$H NMR (600 MHz, DMSO-d$_6$) δ 8.04 (s, 1H), 7.83 (d, J=8.8 Hz, 1H), 7.54 (d, J=8.1 Hz, 1H), 7.44 (d, J=3.6 Hz, 1H), 7.25 (s, 1H), 7.02 (d, J=8.1 Hz, 1H), 6.99 (s, 2H), 6.69 (d, J=8.8 Hz, 1H), 6.60 (d, J=3.6 Hz, 1H), 6.37 (s, 2H), 6.22 (d, J=9.1 Hz, 1H), 5.50-5.32 (m, 2H), 4.61-4.57 (m, 1H), 4.14 (s, 1H), 3.77-3.71 (m, 1H), 2.70-2.65 (m, 2H), 2.13-2.08 (m, 1H), 1.91-1.83 (m, 1H).

Compounds in Table 2 were synthesized in an analogous fashion as described in Example 14 and 15. The starting materials were commercially acquired, synthesized as reported herein, or synthesized through known routes reported in the literature.

TABLE 2

| Example | Structure | Compound Name | Exact Mass [M + 1] |
|---|---|---|---|
| 16 | 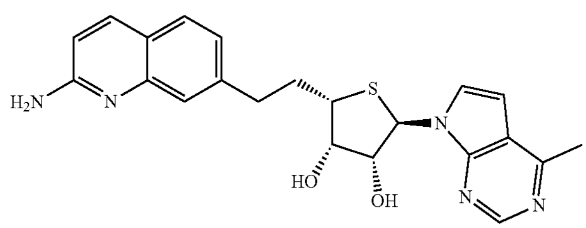 [SMILES: Cc1ncnc2c1ccn2[C@@H]1S[C@@H](CCc2ccc3ccc(N)nc3c2)[C@@H](O)[C@H]1O] | (2S,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol | 422 |
| 17 | 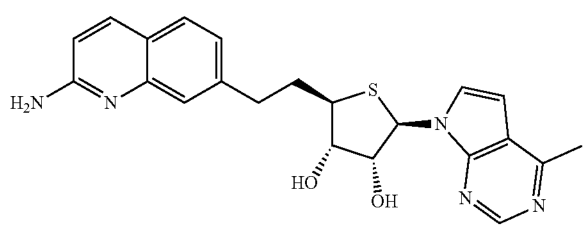 [SMILES: Cc1ncnc2c1ccn2[C@@H]1S[C@H](CCc2ccc3ccc(N)nc3c2)[C@@H](O)[C@H]1O] | (2R,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol | 422 |

Example 18: (2R,3S,4R,5R)-2-(2-(2-amino-3-bromoquinolin-7-yl)ethyl)-5-(4-methyl-7H-pyrrolo[2,3-d]pyrimidin-7-yl)tetrahydrothiophene-3,4-diol Example 19: (2S,3S,4R,5R)-2-(2(2-amino-3-bromo-quinolin-7yl-ethyl)-5-(4-methyl-7H-pyrrolo[2,3-d]pyrimidin-7-yl)tetrahydrothiophene-3,4-diol

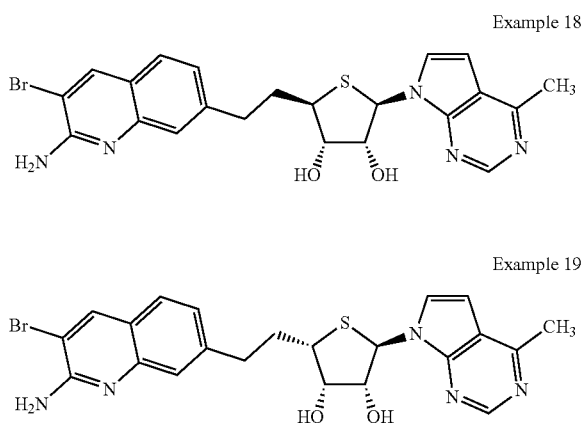

Example 18

Example 19

Step 1: In a flask charged with 7-((3aR,4R,6aS)-2,2-dimethyl-6-vinyltetrahydrothieno[3,4-d][1,3]dioxol-4-yl)-4-methyl-7H-pyrrolo[2,3-d]pyrimidine (0,200 g, 0.630 mmol) at 0° C. was added 9-BBN (0.5 M in THF, 3.78 mL, 1.890 mmol). The reaction mixture was stirred at room temperature overnight. The reaction was quenched with $K_3PO_4$ (2 M in water; 1.58 mL, 3.15 mmol) and the mixture was stirred for 30 min. To the quenched reaction was added a mixture of 3-bromo-7-iodoquinolin-2-amine (0,396 g, 1.13 mmol) and Pd(dppf)$Cl_2 \cdot CH_2Cl_2$ (0.077 g, 0.095 mmol) in THF (2.5 mL) via a syringe. The reaction mixture was heated at 50° C. for 8 h. The reaction mixture was diluted with DCM and water. The organic layer was washed with brine and concentrated under reduced pressure. The residue was purified by column chromatography on silica (0-20% EtOAc/hexane) to give 3-bromo-7-(2-((3aS,6R,6aR)-2,2-dimethyl-6-(4-methyl-7H-pyrrolo[2,3-d]pyrimidin-7-yl)tetrahydrothieno[3,4-d][1,3]dioxol-4-yl)ethyl)quinolin-2-amine. MS: 540, 542 (M+1).

Step 2: In a flask charged with 3-bromo-7-(2-((3aS,6R,6aR)-2,2-dimethyl-6-(4-methyl-7H pyrrolo[2,3-d]pyrimidin-7-yl)tetrahydrothieno[3,4-d][1,3]dioxol-4-yl)ethyl)quinolin-2-amine (340 mg, 0.629 mmol) was added DCM (3 mL) and then TFA (3 mL, 38.9 mmol). The reaction mixture was stirred at room temperature overnight. The mixture was concentrated under reduced pressure and the residue was purified by reverse phase HPLC (ACN/water with 0.1% TFA modifier) followed by SFC separation ((R,R)-Whelk O-1 column, 40%/60% (MeOH w/0.1% $NH_4OH$)/$CO_2$) to give two isomers:

(2R,3S,4R,5R)-2-(2-(2-amino-3-bromoquinolin-7yl) ethyl)-5-(4-methyl-7H-pyrrolo[2,3-d]pyrimidin-7-yl) tetrahydrothiophene-3,4-diol (Example 18). MS: 500, 502 (M+1). $^1$H NMR (600 MHz, DMSO-$d_6$) δ 8.67 (s, 1H), 8.36 (s, 1H), 7.88 (d, J=3.4 Hz, 1H), 7.62 (d, J=8.2 Hz, 1H), 7.34 (s, 1H), 7.14 (d, J=8.1 Hz, 1H), 6.79 (d, J=3.4 Hz, 1H), 6.24 (d, J=6.0 Hz, 1H), 5.50-5.46 (m, 1H), 5.35-5.31 (m, 1H), 4.53-4.49 (m, 1H), 4.10-4.07 (m, 1H), 3.23-3.18 (m, 1H), 2.89-2.83 (m, 1H), 2.75-2.69 (m, 1H), 2.66 (s, 3H), 2.37-2.30 (m, 1H), 2.15-2.06 (m, 1H).

(2S,3S,4R,5R)-2-(2-(2-amino-3-bromoquinolin-7-yl) ethyl)-5-(4-methyl-7H-pyrrolo[2,3-d]pyrimidin-7-yl) tetrahydrothiophene-3,4-diol (Example 19), MS: 500, 502 (M+1). $^1$H NMR (600 MHz, DMSO-$d_6$) δ 8.64 (s, 1H), 8.35 (s, 1H), 7.87 (d, J=3.5 Hz, 1H), 7.61 (d, J=8.2 Hz, 1H), 7.32 (s, 1H), 7.12 (d, J=8.1 Hz, 1H), 6.76 (d, J=3.5 Hz, 1H), 6.33 (d, J=9.0 Hz, 1H), 5.43 (d, J=4.2 Hz, 1H), 5.38 (d, J=7.2 Hz, 1H), 4.71-4.66 (m, 1H), 4.19-4.14 (m, 1H), 3.83-3.79 (m, 1H), 2.74-2.69 (m, 2H), 2.65 (s, 3H), 2.18-2.10 (m, 1H), 1.93-1.86 (m, 1H).

Compounds in Table 3 were synthesized in an analogous fashion as described in steps of Examples 18 and 19. The starting material were commercially acquired, synthesized as reported above, or synthesized through known routes reported in the literature.

TABLE 3

| Example | Structure | Compound Name | Exact Mass [M + 1] |
|---|---|---|---|
| 20 | 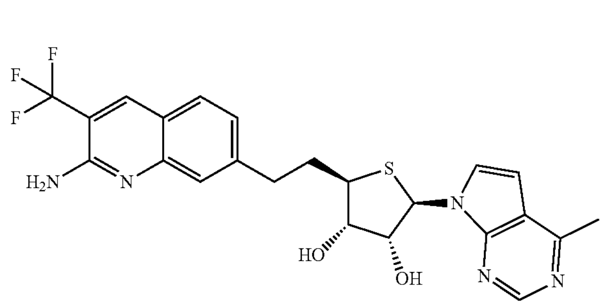 [SMILES: Cc1ncnc2c1ccn2[C@@H]1S[C@H](CCc2ccc3cc(C(F)(F)F)c(N)nc3c2)[C@@H](O)[C@H]1O] | (2R,3S,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol | 490 |

TABLE 3-continued

| Example | Structure | Compound Name | Exact Mass [M + 1] |
|---|---|---|---|
| 21 | 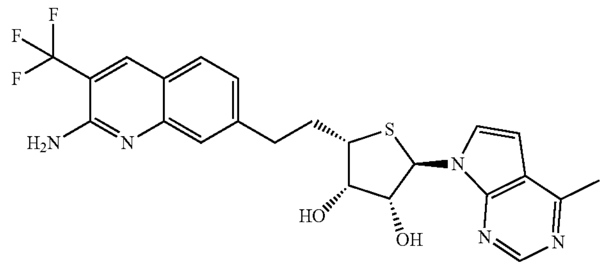 [SMILES: Cc1ncnc2c1ccn2[C@@H]1S[C@@H](CCc2ccc3cc(C(F)(F)F)c(N)nc3c2)[C@@H](O)[C@H]1O] | (2S,3S,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol | 490 |
| 22 | 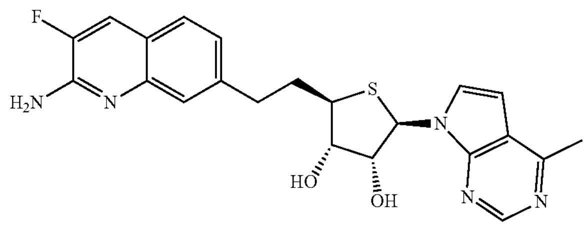 [SMILES: Cc1ncnc2c1ccn2[C@@H]1S[C@H](CCc2ccc3cc(F)c(N)nc3c2)[C@@H](O)[C@H]1O] | (2R,3S,4R,5R)-2-[2-(2-amino-3-fluoroquinolin-7-yl)ethyl]-5-(4-methyl-7H-pyrrolo[2,3-d]pyrimidin-7-yl)tetrahydrothiophene-3,4-diol | 440 |
| 23 | 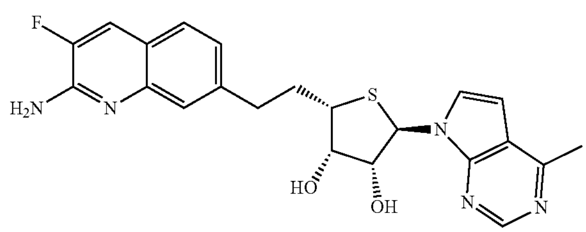 [SMILES: Cc1ncnc2c1ccn2[C@@H]1S[C@@H](CCc2ccc3cc(F)c(N)nc3c2)[C@@H](O)[C@H]1O] | (2S,3S,4R,5R)-2-[2-(2-amino-3-fluoroquinolin-7-yl)ethyl]-5-(4-methyl-7H-pyrrolo[2,3-d]pyrimidin-7-yl)tetrahydrothiophene-3,4-diol | 440 |
| 24 | 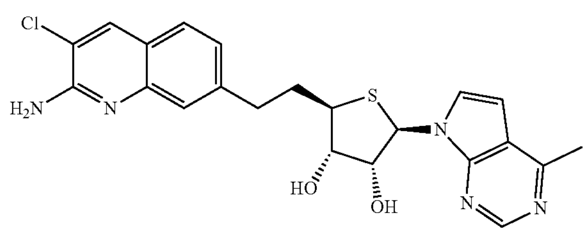 | (2R,3S,4R,5R)-2-[2-(2-amino-3-chloroquinolin-7-yl)ethyl]-5-(4-methyl-7H-pyrrolo[2,3-d]pyrimidin-7-yl)tetrahydrothiophene-3,4-diol | 456 |
| 25 | 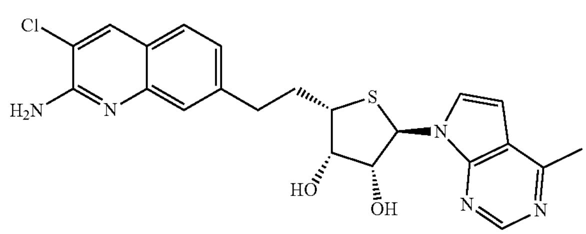 [SMILES: Cc1ncnc2c1ccn2[C@@H]1S[C@@H](CCc2ccc3cc(Cl)c(N)nc3c2)[C@@H](O)[C@H]1O] | (2S,3S,4R,5R)-2-[2-(2-amino-3-chloroquinolin-7-yl)ethyl]-5-(4-methyl-7H-pyrrolo[2,3-d]pyrimidin-7-yl)tetrahydrothiophene-3,4-diol | 456 |
| 26 | 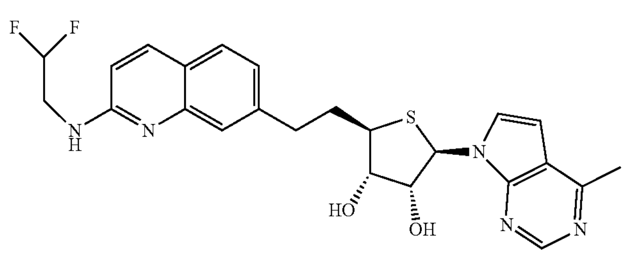 [SMILES: Cc1ncnc2c1ccn2[C@@H]1S[C@H](CCc2ccc3ccc(NCC(F)F)nc3c2)[C@@H](O)[C@H]1O] | (2R,3S,4R,5R)-2-(2-{2-[(2,2-difluoroethyl)amino]quinolin-7-yl}ethyl)-5-(4-methyl-7H-pyrrolo[2,3-d]pyrimidin-7-yl)tetrahydrothiophene-3,4-diol | 486 |

TABLE 3-continued

| Example | Structure | Compound Name | Exact Mass [M + 1] |
|---|---|---|---|
| 27 | 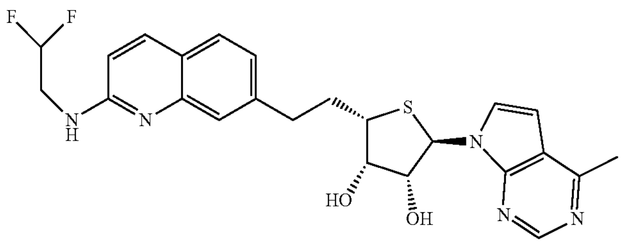 [SMILES: Cc1ncnc2c1ccn2[C@@H]1S[C@@H](CCc2ccc3ccc(NCC(F)F)nc3c2)[C@@H](O)[C@H]1O] | (2S,3S,4R,5R)-2-(2-{2-[(2,2-difluoroethyl)amino]quinolin-7-yl}ethyl)-5-(4-methyl-7H-pyrrolo[2,3-d]pyrimidin-7-yl)tetrahydrothiophene-3,4-diol | 486 |

Example 28: (2R,3S,4R,5R)-2-(2-(2-amino-3-methylquinolin-7-yl)ethyl)-5-(4-methyl-7H-pyrrolo[2,3-d]pyrimidin-7-yl)tetrahydrothiophene-3,4-diol Example 29: (2S,3S,4R,5R)-2-(2-(2-amino-3-methylquinolin-7-yl)ethyl)-5-(4-methyl-7H-pyrrolo[2,3-d]pyrimidin-7-yl)tetrahydrothiophene-3,4-diol Example 28

Example 29

To a mixture of 3-bromo-7-(2-((3aS,4R,6R,6aR)-6-(4-chloro-7H-pyrrolo[2,3-d]pyrimidin-7-yl)-2,2-dimethyltetrahydrothieno[3,4-d][1,3]dioxol-4-yl)ethyl)-N-(4-methoxybenzyl)quinolin-2-amine (0.029 g, 0.043 mmol) and SiliaCat DPP-Pd (0.034 g, 8.52 μmol) in THF (0.43 mL) at 0 5° C. was added dimethylzinc (2M in toluene, 0.064 mL, 0.128 mmol) dropwise. The reaction mixture was stirred at room temperature overnight. The reaction mixture was quenched carefully with MeOH and then diluted with DCM and water. The organic layer was concentrated under reduced pressure, and the residue was treated with TFA (129 μl, 1.68 mmol) and left to stir at room temperature overnight. The reaction mixture was concentrated under reduced pressure, and the residue was purified by reverse phase HPLC (ACN/water with 0.1% TFA modifier) followed by SFC (OJ-H column, 25%/75% (MeOH w/0.25% DMEA)/CO$_2$) to give two isomers:

(2R,3S,4R,5R)-2-(2-(2-amino-3-methylquinolin-7-yl)ethyl)-5-(4-methyl-7H-pyrrolo[2,3-d]pyrimidin-7-yl)tetrahydrothiophene-3,4-diol (peak 1). MS: 436 (M+1). $^1$H NMR (600 MHz, DMSO-d$_6$) δ 8.66 (s, 1H), 7.88 (d, J=3.7 Hz, 1H), 7.68 (s, 1H), 7.52 (d, J=8.1 Hz, 1H), 7.28 (s, 1H), 7.05 (m, 1H), 6.79 (d, J=3.7 Hz, 1H), 6.24 (d, J=6.2 Hz, 1H), 6.20 (s, 2H), 5.51 (brs, 1H), 5.38 (brs, 1H), 4.50 (dd, J=6.0, 3.5 Hz, 1H), 4.07 (t, J=3.5 Hz, 1H), 3.22-3.17 (m, 1H), 2.87-2.81 (m, 1H), 2.71-2.68 (m, 1H), 2.66 (s, 3H), 2.35-2.29 (m, 1H), 2.20 (s, 3H), 2.12-2.05 (m, 1H).

(2S,3S,4R,5R)-2-(2-(2-amino-3-methylquinolin-7yl)ethyl)-5-(4-methyl-7H-pyrrolo[2,3-d]pyrimidin-7-yl)tetrahydrothiophene-3,4-diol (peak 2). MS: 436 (M+1). $^1$H NMR (600 MHz, DMSO-d$_6$) δ 8.64 (s, 1H), 7.88 (d, J=3.7 Hz, 1H), 7.68 (s, 1H), 7.51 (d, J=8.1 Hz, 1H), 7.26 (s, 1H), 7.02 (dd, J=8.1, 1.3 Hz, 1H), 6.76 (d, J=3.7 Hz, 1H), 6.32 (d, J=9.0 Hz, 1H), 6.21 (s, 2H), 5.48 (brs, 1H), 5.43 (brs, 1H), 4.69-4.64 (m, 1H), 4.18-4.14 (m, 1H), 3.83-3.78 (m, 1H), 2.71-2.66 (m, 2H), 2.64 (s, 3H), 2.20 (s, 3H), 2.16-2.08 (m, 1H), 1.92-1.83 (m, 1H).

Example 30: (2R,3S,4R,5R)-2-(2-(2-amino-3-bromoquinolin-7-yl)ethyl-5-(4-amino-7H-pyrrolo[2,3-d]pyrimidin-7-yl)-2-methyltetrahydrothiophene-3,4-diol Example 30

Step 1: To an argon-purged 100 mL round bottom flask containing 4-chloro-7-((3aR,4R,6R,6aS)-2,2,6-trimethyl-6-vinyltetrahydrothieno[3,4-d][1,3]dioxol-4-yl)-7H-pyrrolo[2,3-d]pyrimidine (434 mg, 1.23 mmol) was added 9-BBN (8 ml, 4.00 mmol, 0.5M), The reaction was stirred at room temperature under a balloon of argon overnight. Aqueous tripotassium phosphate (6.2 ml, 6.20 mmol, 1M) was added, and the mixture was vigorously stirred at room temperature for 40 min. A solution of [1,1'-bis(diphenylphosphino)ferrocene]dichloropalladium(ii) (90 mg, 0.123 mmol) and 3-bromo-7-iodoquinolin-2-amine (645 mg, 1.849 mmol) in THF (10 mL) was added, and the reaction was heated to 50° C. under a balloon of argon for 3 h. The reaction was then cooled to room temperature. The mixture was poured into a separately funnel containing water and DCM. The aqueous layer was extracted with DCM, and the combined organic layers were dried over magnesium sulfate, filtered, and concentrated under reduced pressure. The residue was purified by column chromatography on silica (30-75% EtOAc/hexanes) to afford 3-bromo-7-(2-((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)ethyl)quinolin-2-amine as a solid. MS: 574, 576 (M+1).

Step 2: To a microwave vial containing 3-bromo-7-(2-((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)ethyl)quinolin-2-amine (200 mg, 0.348 mmol) was added ammonia (12 mL, 84 mmol, 7M in MeOH). The reaction was heated in the microwave at 140° C. for 5 h. The reaction mixture was concentrated under reduced pressure to afford crude 7-(2-((3aS,4R,6R,6aR)-6-(4-amino-7H-pyrrolo[2,3-d]pyrimidin-7-yl)-2,2,4-trimethyltetrahydrothieno[3,4-d][1,3]dioxol-4-yl)ethyl)-3-bromoquinolin-2-amine which was taken directly to the next reaction without further purification. MS: 555, 557 (M+1).

Step 3: To a 50 mL round bottom flask containing 7-(2-((3aS,4R,6R,6aR)-6-(4-amino-7H-pyrrolo[2,3-d]pyrimidin-7-yl)-2,2,4-trimethyltetrahydrothieno[3,4-d][1,3]dioxol-4-yl)ethyl)-3-bromoquinolin-2-amine (193 mg, 0.348 mmol) was added DCM (10 mL), followed by TFA (10 mL, 130 mmol). The reaction was stirred at room temperature for 2 h. The reaction was concentrated under reduced pressure, and the residue was purified by reverse phase HPLC (ACN/water with 0.1% TFA modifier) to afford (2R,3S,4R,5R)-2-(2-(2-amino-3-bromoquinolin-7-yl)ethyl)-5-(4-amino-7H-pyrrolo[2,3d]pyrimidin-7-yl)-2-methyltetrahydrothiophene-3,4-diol, TFA salt as a solid. MS: 515, 517 (M+1). $^1$H NMR (600 MHz, DMSO-d6) δ 8.64 (s, 1H), 8.38 (s, 1H), 7.80 (d, J=3.7 Hz, 1H), 7.73 (d, J=8.2 Hz, 1H), 7.49 (s, 1H), 7.35 (d, J=8.1 Hz, 1H), 6.98 (d, J=3.7 Hz, 1H), 6.26 (d, J=8.3 Hz, 1H), 4.87 (dd. J=8.3, 3.5 Hz, 1H), 3.92 (d, J=3.4 Hz, 1H), 2.88-2.80 (m, 2H), 2.27-2.20 (m, 1H), 2.18 2.11 (m, 1H), 1.45 (s, 3H).

Example 31: (2R,3S,4R,5R)-2-(2-(2-amino-3-bromoquinolin-7-yl)ethyl)-5-(4-chloro-7H-pyrrolo[2,3-d]pyrimidin-7-yl)-2-methyltetrahydrothiophene-3,4-diol

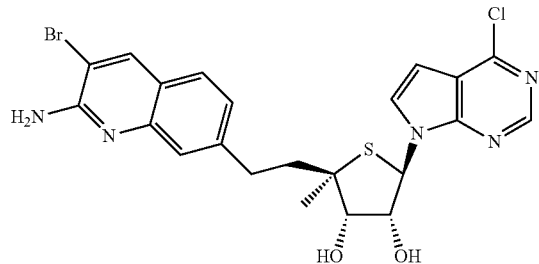

Example 31

To a mixture of 3-bromo-7-(2-((3aS,4R,6R,6aR)-6-(4-chloro-7H-pyrrolo[2,3-d]pyrimidin-7-yl)-2,2,4-trimethyltetrahydrothieno[3,4-d][1,3]dioxol-4-yl)ethyl)quinolin-2-amine (33.2 mg, 0.058 mmol) in THF (0.5 mL) and water (0.3 mL) was added formic acid (0.7 mL). The reaction mixture was stirred overnight at room temperature, and then heated to 50° C. for 2 h, then cooled to room temperature. Additional formic acid (0.7 mL) was added, and the mixture was heated to 50° C. for 2 h, then cooled to room temperature. The mixture was purified by reverse phase HPLC (ACN/water with 0.1% NH$_4$OH modifier) to give (2R,3S,4R,5R)-2-(2-(2-amino-3-bromoquinolin-7-yl)ethyl)-5-(4-chloro-7H-pyrrolo[2,3-d]pyrimidin-7-yl)-2-methyltetrahydrothiophene-3,4-diol. MS: 534, 536 (M+1). $^1$H NMR (600 MHz, DMSO-d6) δ 8.65 (s, 1H), 8.35 (s, 1H), 8.08 (d, J=3.8 Hz, 1H), 7.62 (d, J=8.2 Hz, 1H), 7.40 (s, 1H), 7.20 (d, J=8.2 Hz, 1H), 6.76 (d, J=3.7 Hz, 1H), 6.58 (brs, 2H), 6.35 (d, J=8.3 Hz, 1H), 5.55 (d, J=4.7 Hz, 1H), 5.42 (d, J=7.2 Hz, 1H), 5.02 (td, J=8.2, 3.5 Hz, 1H), 4.02-3.83 (m, 1H), 2.91-2.73 (m, 2H), 2.36-2.25 (m, 1H), 2.21-2.11 (m, 1H), 1.46 (s, 3H).

Example 32: (2R,3S,4R,5R)-2-(2-(2-amino-3-bromoquinolin-7-yl)ethyl-2-methyl-5-(4-methyl-7H-pyrrolo[2,3-d]pyrimidin-7-yl)tetrahydrothiophene-3,4-diol

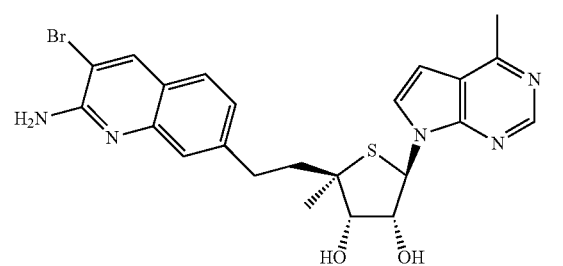

Example 32

To a mixture of 3-bromo-7-(2-((3aS,4R,6R,6aR)-6-(4-chloro-7H-pyrrolo[2,3d]pyrimidin-7yl)-2,2,4-trimethyltetrahydrothieno[3,4d][1,3]dioxol-4yl)ethyl)quinolin-2-amine (69.9 mg, 0,122 mmol), (1,3-bis(diphenylphosphino) propane) palladium(II) chloride (55.1 mg, 0.091 mmol) was added THF (1.2 mL), followed by dropwise addition of methylmagnesium bromide (1.4 M in THF 0.26 mL, 0.35 mmol). The resulting mixture was heated to 50° C. for 3 h, then cooled to room temperature. Additional methylmagnesium bromide (1.4 M in THF 0.26 mL, 0.35 mmol) was added, and the mixture was heated to 50° C. for 30 min, then cooled to room temperature. Additional methylmagnesium bromide (1.4 M in THF 10 mL, 1.4 mmol) was added, and the mixture was heated to 50° C. for 30 min, then cooled to room temperature. Additional methylmagnesium bromide (1.4 M in THF, 5 mL, 0.7 mmol) was added, and the mixture was heated to 50° C. for 60 mins, then cooled to room temperature. The reaction mixture was diluted with EtOAc and quenched by addition of saturated aqueous NH$_4$Cl. The aqueous layer was extracted with EtOAc, and the combined organic layers were dried over anhydrous MgSO$_4$, filtered, and concentrated under reduced pressure. The residue was dissolved in THF (0.5 mL), water (0.3 mL), and formic acid (0.7 mL), and heated to 50° C. for 3 h, then cooled to room temperature. Additional formic acid (0.7 mL) was added, and the mixture was heated to 50° C. for min, then cooled to room temperature. Additional formic acid (0.7 mL) was added, and the mixture was heated to 50° C. for 30 min, then cooled to room temperature. The reaction mixture was purified by reverse phase HPLC (ACN/water with 0.1% NH$_4$OH modifier) to give (2R,3S,4R,5R)-2-(2-(2-amino-3-bromoquinolin-7-yl)ethyl)-2-methyl-5-(4-methyl-7H-pyrrolo[2,3-d]pyrimidin-7-yl)tetrahydrothiophene-3,4-diol. MS: 514, 516 (M+1). $^1$H NMR (600 MHz, DMSO-d6) δ 8.65 (s, 1H), 8.35 (s, 1H), 7.84 (d, J=3.7 Hz, 1H), 7.62 (d, J=8.2 Hz, 1H), 7.40 (s, 1H), 7.19 (dd, J=8.2, 1.4 Hz, 1H), 6.77 (d, J=3.7 Hz, 1H), 6.58 (br s, 2H), 6.35 (d, J=8.3 Hz, 1H), 5.49 (d, J=4.7 Hz, 1H), 5.35 (d, J=7.3 Hz, 1H), 5.01 (d, J=7.9, 3.5 Hz, 1H), 3.98-3.88 (m, 1H), 2.88-2.76 (m, 2H), 2.65 (s, 3H), 2.35-2.25 (m, 1H), 2.21-2.10 (m, 1H), 1.45 (s, 3H).

Example 33: (2R,3S,4R,5R)-2-(2-(2-amino-3-bromoquinolin-7-yl)ethyl)-2-methyl-5-(4-(methylamino)-7H-pyrrolo[2,3-d]pyrimidin-7-yl)tetrahydrothiophene-3,4-diol Example 33

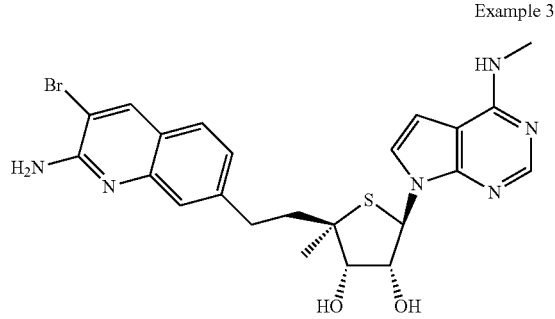

To a mixture of (2R,3S,4R,5R)-2-(2-(2-amino-3-bromoquinolin-7-yl)ethyl)-5-(4-chloro-7H-pyrrolo[2,3-d]pyrimidin-7-yl)-2-methyltetrahydrothiophene-3,4-diol (5.8 mg, 0.011 mmol) in DMSO (1.1 mL) was added methylamine (40% in water, 1 ml, 11.6 mmol). The resulting mixture was heated to 160° C. in a microwave reactor for 90 min, then cooled to room temperature. The reaction mixture was purified by reverse phase HPLC (ACN/water with 0.1% NH$_4$OH modifier) to give (2R,3S,4R,5R)-2-(2-(2-amino-3-bromoquinolin-7-yl)ethyl)-2-methyl-5-(4-(methylamino)-7H-pyrrolo[2,3-d]pyrimidin-7-yl)tetrahydrothiophene-3,4-diol. MS: 529, 531 (M+1). $^1$H NMR (600 MHz, DMSO-d6) δ 8.35 (s, 1H), 8.15 (s, 1H), 7.61 (d, J=8.2 Hz, 1H), 7.51-7.45 (m, 1H), 7.40 (d, J=3.6 Hz, 1H), 7.38 (s, 1H), 7.18 (dd, J=8.2, 1.4 Hz, 1H), 6.60 (d, J=3.6 Hz, 1H), 6.59 (brs, 2H), 6.24 (d, J=8.0 Hz, 1H), 5.42 (d, J=4.8 Hz, 1H), 5.28 d, J=7.3 Hz, 1H), 4.91 (td, J=7.7, 3.6 Hz, 1H), 3.93-3.88 (m, 1H), 2.96 (d, J=4.5 Hz, 3H), 2.84-2.77 (m, 2H), 2.28-2.20 (m, 1H), 2.13-2.09 (m, 1H), 1.44 (s, 3H).

Example 34: (2R,3S,4R,5R)-2-(2-(2-amino-3-bromoquinolin-7-yl)ethyl)-5-(4-amino-5-methyl-7H-pyrrolo[2,3-d]pyrimidin-7-yl)tetrahydrothiophene-3,4-diol Example 34

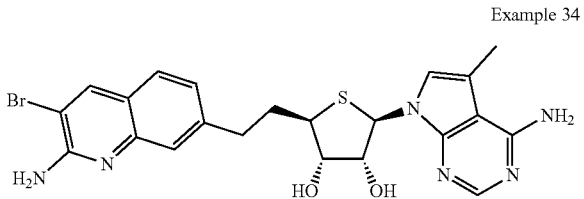 [SMILES: Cc1cn([C@@H]2S[C@H](CCc3ccc4cc(Br)c(N)nc4c3)[C@@H](O)[C@H]2O)c2ncnc(N)c12]

Step 1: To a flask containing (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-ol (500 mg, 0.92 mmol), 4-chloro-5-methyl-7H-pyrrolo[2,3-d]pyrimidine (290 mg, 1.73 mmol), and triphenylphosphine (720 mg, 2.75 mmol) was added THF (9 mL). The solution was cooled to 0° C., and diisopropyl azodicarboxylate (0.53 mL, 2.75 mmol) was added. The reaction mixture was slowly warmed to room temperature and stirred overnight under a nitrogen atmosphere. The reaction mixture was diluted with ethyl acetate and then washed with water. The organic layer was dried over anhydrous magnesium sulfate, filtered, and concentrated under reduced pressure. The residue was purified by column chromatography on silica (0-40% EtOAc/hexanes) to afford 3-bromo-7-(2-((3aS,4R,6R,6aR)-6-(4-chloro-5-methyl-7H-pyrrolo[2,3-d]pyrimidin-7-yl)-2,2-dimethyltetrahydrothieno[3,4-d][1,3]dioxol-4-yl)ethyl)-N-(4-methoxybenzyl)quinolin-2-amine as a foam. MS: 694, 696 (M+1).

Step 2: In a 20 mL microwave vial charged with 3-bromo-7-(2-((3aS,4R,6R,6aR)-6-(4-chloro-5-methyl-7H-pyrrolo[2,3-d]pyrimidin-7-yl)-2,2-dimethyltetrahydrothieno[3,4-d][1,3]dioxol-4-yl)ethyl)-N-(4-methoxybenzyl)quinolin-2-amine (152 mg, 0.22 mmol), ammonium hydroxide in methanol (10 mL, 70.0 mmol) was added. The reaction mixture was heated at 140° C. in a microwave reactor for 5 h. The mixture was concentrated under reduced pressure to give 7-(2-((3aS,4R,6R,6aR)-6-(4-amino-5-methyl-7H-pyrrolo[2,3-d]pyrimidin-7-yl)-2,2-dimethyltetrahydrothieno[3,4-d][1,3]dioxol-4-yl)ethyl)-3-bromo-N-(4-methoxybenzyl)quinolin-2-amine winch was used without further purification. MS: 675, 677 (M+1).

Step 3: To a flask containing 7-(2-((3aS,4R,6R,6aR)-6-(4-amino-5-methyl-7H-pyrrolo[2,3-d]pyrimidin-7-yl)-2,2-dimethyltetrahydrothieno[3,4-d][1,3]dioxol-4-yl)ethyl)-3-bromo-N-(4-methoxybenzyl)quinolin-2-amine (148 mg, 0.22 mmol) was added TFA (1.0 mL, 13 mmol). The reaction mixture was stirred at room temperature overnight. The reaction was concentrated under reduced pressure. The residue was purified by reverse phase HPLC (ACN/water with 0.1% TFA modifier) to give (2R,3S,4R,5R)-2-(2-(2-amino-3-bromoquinolin-7-yl)ethyl)-5-(4-amino-5-methyl-7H-pyrrolo[2,3-d]pyrimidin-7-yl)tetrahydrothiophene-3,4-diol, TFA salt as a solid. MS: 515, 517 (M+1). $^1$H NMR (600 MHz, DMSO) δ 8.73 (s, 1H), 8.35 (s, 1H), 7.78 (d, J=8.2 Hz, 1H), 7.61 (s, 1H), 7.47 (s, 1H), 7.34 (d, J=7.8 Hz, 1H), 6.13 (d, J=6.3 Hz, 1H), 4.41 (dd, J=6.2, 3.5 Hz, 1H), 4.07 (t, J=3.6 Hz, 1H), 3.23-3.18 (m, 1H), 2.93-2.87 (m, 1H), 2.81-2.75 (m, 1H), 2.43 (s, 3H), 2.36-2.31 (m, 1H), 2.14-2.06 (m, 1H). Compounds in Table 4 were synthesized in an analogous fashion as described in the steps of Example 34. The starting materials were commercially acquired, synthesized as reported above, or synthesized through known routes reported in the literature. For example 36, the procedure in step 2 was modified in that ammonium hydroxide in methanol was substituted with 2M methylamine in THF (34 equivalents) as a solution in dioxane (0.05M) and the reaction was heated at 70° C. overnight.

reaction mixture was allowed to warm to room temperature and stirred overnight under a nitrogen atmosphere. The reaction mixture was diluted with ethyl acetate and washed with water. The organic layer was dried over anhydrous magnesium sulfate, filtered, and concentrated under reduced pressure. The residue was purified by column chromatography on silica (0-40% EtOAc/hexanes) to afford 7-[6-{3-

TABLE 4

| Example | Structure | Compound Name | Exact Mass [M + 1] |
|---|---|---|---|
| 35 | 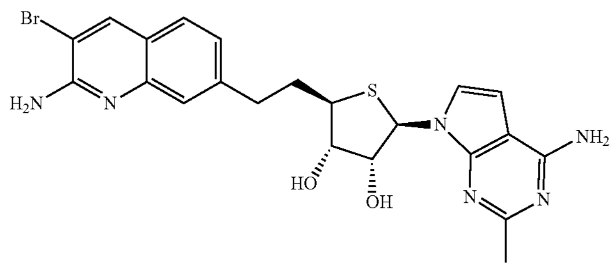 [SMILES: Cc1nc(N)c2ccn([C@@H]3S[C@H](CCc4ccc5cc(Br)c(N)nc5c4)[C@@H](O)[C@H]3O)c2n1] | (2R,3R,4S,5R)-2-(4-amino-2-methyl-7H-pyrrolo[2,3-d]pyrimidin-7-yl)-5-(2-(2-amino-3-bromoquinolin-7-yl)ethyl)tetrahydrothiophene-3,4-diol | 515, 517 |
| 36 | 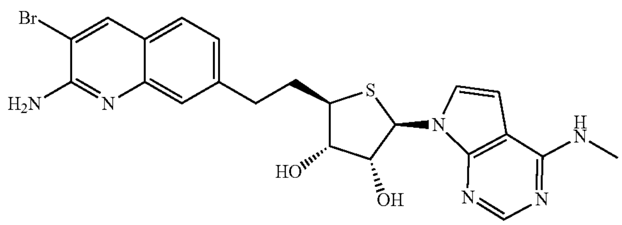 [SMILES: CNc1ncnc2c1ccn2[C@@H]1S[C@H](CCc2ccc3cc(Br)c(N)nc3c2)[C@@H](O)[C@H]1O] | (2R,3S,4R,5R)-2-(2-(2-amino-3-bromoquinolin-7-yl)ethyl)-5-(4-(methylamino)-7H-pyrrolo[2,3-d]pyrimidin-7-yl)tetrahydrothiophene-3,4-diol | 515, 517 |
| 37 | 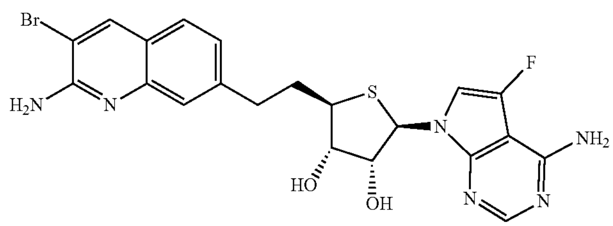 [SMILES: Nc1nc2cc(CC[C@H]3S[C@@H](n4cc(F)c5c(N)ncnc54)[C@H](O)[C@@H]3O)ccc2cc1Br] | (2R,3S,4R,5R)-2-(2-(2-amino-3-bromoquinolin-7-yl)ethyl)-5-(4-amino-5-fluoro-7H-pyrrolo[2,3-d]pyrimidin-7-yl)tetrahydrothiophene-3,4-diol | 519, 521 |

Example 38: (2R,3S,4R,5R)-2-(2-(2-amino-3-bromoquinolin-7-yl)ethyl)-5-(2-amino-4-methyl-7H-pyrrolo[2,3-d]pyrimidin-7-yl)tetrahydrothiophene-3,4-diol

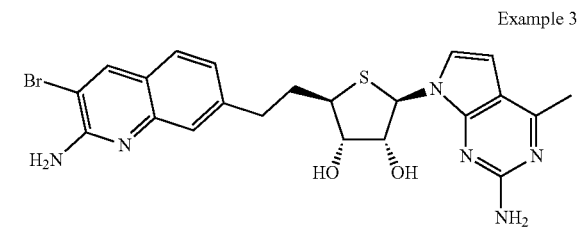

Example 38

Step 1: To a flask charged with (3aR,6R,6aS)-6-(2-(3-bromo-2-((4-methoxybenzyl)amino)quinolin-7-yl)ethyl)-2,2-dimethyltetrahydrothieno[3,4-d][1,3]dioxol-4-ol (120 mg, 0.22 mmol), di-tert-butyl (4-methyl-7H-pyrrolo[2,3-d]pyrimidin-2-yl)imidodicarbonate (115 mg, 0.33 mmol), and triphenylphosphine (173 mg, 0.66 mmol) was added THF (1.8 mL). The solution was cooled to 0° C., then diisopropyl azodicarboxylate (0.13 mL, 0.66 mmol) was added. The bromo-2-[(4-methoxybenzyl)amino]quinolin-7-yl}-5,6-dideoxy-2,3-O-(1-methylethylidene)-4-thio-b-D-ribo-hexofuranosyl]-N,N-bis(tert-butoxycarbonyl)-4-methyl-7H-pyrrolo[2,3-d]pyrimidin-2-amine. MS: 875, 877 (M+1).

Step 2: TFA (0.3 mL, 3.9 mmol) was added to 7-[6-{3-bromo-2-[(4-methoxybenzyl)amino]quinolin-7-yl}-5,6-dideoxy-2,3-O-(1-methylethylidene)-4-thio-b-D-ribo-hexofuranosyl]-N,N-bis(tert-butoxycarbonyl)-4-methyl-7H-pyrrolo[2; 3-d]pyrimidin-2-amine (43 mg, 0.05 mmol). The reaction mixture was stirred at room temperature overnight. The reaction was concentrated under reduced pressure and the residue was purified by reverse phase HPLC (ACN/water with 0.1% TFA modifier) to afford (2R,3S,4R,5R)-2-(2-(2-amino-3-bromoquinolin-7-yl)ethyl)-5-(2-amino-4-methyl-7H-pyrrolo[2,3-d]pyrimidin-7-yl)tetrahydrothiophene-3,4-diol, TFA salt. MS: 515, 517 (M+1). $^1$H NMR (600 MHz, DMSO) δ 8.61 (s, 1H), 7.76 (d, J=3.9 Hz, 1H), 7.72 (d, J=8.2 Hz, 1H), 7.41 (s, 1H), 7.27 (d, J=8.1 Hz, 1H), 6.85 (d, J=3.9 Hz, 1H), 6.18-5.95 (m, 1H), 4.46 (dd, J=6.8, 3.4 Hz, 1H), 4.07 (t, J=3.2 Hz, 1H), 3.18-3.14 (m, 1H), 2.91-2.82 (m, 1H), 2.78-2.72 (m, 1H), 2.66 (s, 3H), 2.34-2.28 (m, 1H), 2.15-2.03 (m, 1H).

Example 39: (2S,3S,4R,5R)-2-(2-((R or S)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol (First Eluting Isomer, Peak1 1)

And

Example 40: (2S,3S,4R,5R)-2-(2-((S or R)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol (Second Eluting Isomer, Peak 2)

Example 39, 40

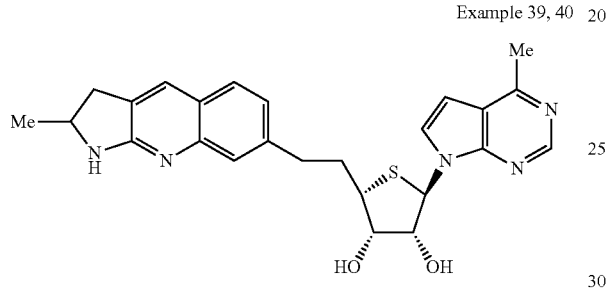

Step 1: To a flask containing 7-((3aR,4R,6R,6aS)-2,2-dimethyl-6-vinyltetrahydrothieno[3,4-d][1,3]dioxol-4-yl)-4-methyl-7H-pyrrolo[2,3-d]pyrimidine (45 mg, 0.14 mmol) was added 9-BBN (0.5M in THF, 1.4 ml, 0.7.1 mmol) at ambient temperature under argon atmosphere. The resultant mixture was stirred at 60° C. for 1 h. To this was added a solution of $K_3PO_4$ (150 mg, 0.71 mmol) in water (0.6 mL) at 0° C. under an argon atmosphere, and the resulting solution was stirred at room temperature for 0.5 h. A solution of 7-bromo-2-methyl-2,3-dihydro-1H-pyrrolo[2,3-b]quinoline (39 mg, 0.15 mmol) in THF (0.3 mL) and [1,1'-bis(diphenylphosphino)ferrocene]dichloropalladium(II) (10.4 mg, 0.014 mmol) were added to the boronate, and the reaction was stirred in under microwave radiation at 70° C. for 3 h. The reaction mixture was concentrated under reduced pressure, and the residue was purified by preparative TLC (developed by DCM/MeOH=15:1) to give 7-(2-((3aS,4S,6R,6aR)-2,2-dimethyl-6-(4-methyl-7H-pyrrolo[2,3-d]pyrimidin-7-yl)tetrahydrothieno[3,4-d][1,3]dioxol-4-yl)ethyl)-2-methyl-2,3-dihydro-1H-pyrrolo[2,3-d]quinoline as a solid. MS: 502 (M+1).

Step 2: To a solution of 7-(2-((3aS,4S,6R,6aR)-2,2-dimethyl-6-(4-methyl-7H-pyrrolo[2,3-d]pyrimidin-7-yl)tetrahydrothieno[3,4-d][1,3]dioxol-4-yl)ethyl)-2-methyl-2,3-dihydro-1H-pyrrolo[2,3-h]quinoline (45 mg, 0.09 mmol) in water (1 mL) was added 2,2,2-trifluoroacetic acid (1 mL, 13.46 mmol) at 0° C. The resulting mixture was stirred at ambient temperature for 1 h. The reaction was concentrated under reduced pressure with toluene. The residue was purified by reverse phase HPLC (ACN/water with 5 mM $NH_4HCO_3$ modifier) followed by chiral HPLC (Chiralpak IC, Hex:DCM (1:1) with 10 mM $NH_3$-MeOH— and EtOH) to afford:

Example 39: (2S,3S,4R,5R)-2-(2-((R or S)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol (peak 1). MS: 462 (M+1) $^1$H-NMR (400 MHz, DMSO-$d_6$) δ 8.63 (s, 1H), 7.87 (d, J=3.6 Hz, 1H), 7.57 (s, 1H), 7.46 (d, J=8.4 Hz, 1H), 7.22 (s, 1H), 7.11 (s, 1H), 6.98 (dd, J=8.0, 1.6 Hz, 1H), 6.75 (d, J=3.6 Hz, 1H), 6.32 (d, J=9.2 Hz, 1H), 5.42 (d, J=4.4 Hz. 1H), 5.37 (d, J=6.8 Hz, 1H), 4.69-4.64 (m, 1H), 4.15 (d, J=3.6 Hz, 1H), 3.98-3.96 (m, 1H), 3.80 (t, J=4.0 Hz, 1H), 3.29-3.21 (m, 1H), 2.67-2.54 (m, 6H), 2.12-2.07 (m, 1H), 1.89-1.88 (m, 1H), 1.24-1.22 (m, 3H).

Example 40: (2S,3S,4R,5R)-2-(2-((S or R)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol (peak 2). MS: 462 (M+1). $^1$H NMR (400 MHz, DMSO-d6) δ 8.63 (s, 1H), 7.87 (d, J=3.6 Hz, 1H), 7.57 (s, 1H), 7.46 (d, J=8.0 Hz, 1H), 7.23 (s, 1H), 7.13 (s, 1H), 6.98 (d, J=9.2 Hz, 1H), 6.75 (d, J=3.6 Hz, 1H), 6.32 (d, J=8.8 Hz, 1H), 5.43 (d, J=4.4 Hz, 1H), 5.38 (d, J=7.2 Hz, 1H), 4.69-4.64 (m, 1H), 4.16-4.15 (m, 1H), 4.00-3.93 (m, 1H), 3.82-3.80 (m, 1H), 3.27-3.21 (m, 1H), 2.67-2.61 (m, 6H), 2.14-2.09 (m, 1H), 1.91-1.82 (m, 1H), 1.22-1.18 (m, 3H).

The compound in Table 5 was synthesized in an analogous fashion of Examples 39 and 40. The starting material were commercially acquired, synthesized as reported herein, or synthesized through known routes reported in the literature.

TABLE 5

| Example | Structure | Compound Name | Exact Mass [M + 1] |
|---|---|---|---|
| 41 | ![structure] | (2S,3S,4R,5R)-2-(2-(2-amino-3-(difluoromethyl)quinolin-7-yl)ethyl)-5-(4-methyl-7H-pyrrolo[2,3-d]pyrimidin-7-yl)tetrahydrothiophene-3,4-diol | 472 |

Example 42: (2S,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol Example 42

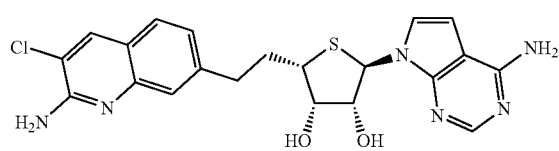

Step 1: To a flask containing 4-chloro-7-((3aR,4R,6aS)-2,2-dimethyl-6-vinyltetrahydrothieno[3,4-d][1,3]dioxol-4-yl)-7H-pyrrolo[2,3-d]pyrimidine (250 mg, 0.73 mmol) was added 9-BBN (0.5M in THF 4.4 ml, 2.2 mmol) at 0° C. The mixture was stirred at room temperature overnight. The reaction was quenched with aqueous tripotassium phosphate (2M, 1.8 ml, 3.7 mmol), and the mixture was stirred at room temperature for 30 min. Separately, 7-bromo-3-chloroquinolin-2-amine (330 mg, 1.03 mmol), methanesulfonato(2-dicyclohexylphosphino-2',6'-di-iso-propoxy-1,1'-biphenyl)(2'-amino-1,1'-biphenyl-2-yl)palladium(ii) (92 mg, 0.11 mmol), and dioxane (3.7 ml) were stirred in a vial. The mixture was transferred to the above borane solution and the reaction mixture was heated at 50° C. overnight. The reaction was quenched with water and DCM, and the organic layer was isolated by passing the mixture through a phase separator. The organic layer was concentrated under reduced pressure, and the residue was purified by column chromatography on silica (30%-100% EtOAc/hexanes) to give 3-chloro-7-(2-((3aS,6R,6aR)-6-(4-chloro-7H-pyrrolo[2,3-d]pyrimidin-7-yl)-2,2-dimethyltetrahydrothieno[3,4-d][1,3]dioxol-4-yl)ethyl)quinolin-2-amine. MS: 516 (M+1).

Step 2: To a vial containing 3-chloro-7-(2-((3aS,4R,6aR)-6-(4-chloro-7H-pyrrolo[2,3-d]pyrimidin-7-yl)-2,2-dimethyltetrahydrothieno[3,4-d][1,3]dioxol-4-yl)ethyl)quinolin-2-amine (35 mg, 0.068 mmol) was added ammonium hydroxide (7N in methanol, 10 mL, 70.0 mmol). The reaction mixture was heated in a microwave reactor at 140° C. for 5 h. The reaction was concentrated under reduced pressure. The residue was purified by chiral SFC (40%/60% (MeOH w/0.1% NH$_4$OH)/CO$_2$) to give two isomers: 7-(2-((3aS,4S,6R,6aR)-6-(4-amino-7H-pyrrolo[2,3-d]pyrimidin-7-yl)-2,2-dimethyltetrahydrothieno[3,4-d][1,3]dioxol-4-yl)ethyl)-3-chloroquinolin-2-amine (peak 1) MS: 497 (M+1) and 7-(2-((3aS,4R,6R,6aR)-6-(4-amino-7H-pyrrolo[2,3-d]pyrimidin-7-yl)-2,2-dimethyltetrahydrothieno[3,4-d][1,3]dioxol-4-yl)ethyl)-3-chloroquinolin-2-amine (peak 2) MS: 497 (M+1)

Step 3: TFA (200 μl, 2.6 mmol) and a few drops of water were added to a vial charged with 7-(2 ((3aS,4S,6R,6aR)-6-(4-amino-7H-pyrrolo[2,3d]pyrimidin-7-yl)-2,2-dimethyltetrahydrothieno[3,4-d][1,3]dioxol-4-yl)-ethyl)-3-chloroquinolin-2-amine (5.6 mg, 0.011 mmol). The reaction mixture was heated at 50° C. for 2 h, then stirred at room temperature overnight. The reaction was concentrated under reduced pressure. The residue was purified by reverse phase HPLC (ACN/water with 0.1% TFA modifier) to afford (2S,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol, TFA salt, MS: 457 (M+1) $^1$H NMR (600 MHz, DMSO) δ 8.53 (s, 1H), 8.38 (s, 1H), 7.84 (d, J=3.7 Hz, 1H), 7.76 (d, J=8.2 Hz, 1H), 7.45 (s, 1H), 7.31 (d, J=8.3 Hz, 1H), 6.99 (d, J=3.7 Hz, 1H), 6.22 (d, J=8.9 Hz, 1H), 4.60 (dd, J=9.0, 3.0 Hz, 1H), 4.18-4.15 (m, 1H), 3.87-3.83 (m, 1H), 2.82-2.71 (m, 2H), 2.22-2.10 (m, 1H), 1.92-1.85 (m, 1H).

Example 43: (2R,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol Example 43

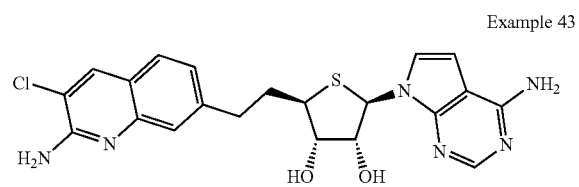 [SMILES: Nc1nc2cc(CC[C@H]3S[C@@H](n4ccc5c(N)ncnc54)[C@H](O)[C@@H]3O)ccc2cc1Cl]

(2R,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol, TFA salt was prepared utilizing the procedure described in Example 42, Step 3 and utilizing 7-(2-((3aS,4R,6R,6aR)-6-(4-amino-7H-pyrrolo[2,3-d]pyrimidin-7-yl)-2,2-dimethyltetrahydrothieno[3,4-d][1,3]dioxol-4-yl)ethyl)-3-chloroquinolin-2-amine as starting material MS: 457 (M+1) $^1$H NMR (600 MHz, DMSO) δ 8.56 (s, 1H), 8.40 (s, 1H), 7.83 (d, J=3.7 Hz, 1H), 7.78 (d, J=8.2 Hz, 1H), 7.47 (s, 1H), 7.35 (d, J=8.2 Hz, 1H), 7.01 (d, J=3.7 Hz, 1H), 6.14 (d, J=6.2 Hz, 1H), 4.45 (dd, J=6.1, 3.5 Hz, 1H), 4.12-4.03 (m, 1H), 3.20-3.24 (m, 1H), 2.94-2.88 (m, 1H), 2.82-2.76 (m, 1H), 2.36-2.31 (m, 1H), 2.14-2.06 (m, 1H).

PRMT5-MEP50 Enzyme Methylation Assay

PRMT5-MEP50 biochemical assay is a direct measurement of the methylation activity of the enzyme complex on a short peptide substrate derived from the N-terminus of H4 histone. Methylation experiment is performed with recombinant PRMT5-MEP50 protein complex. The assessment of inhibitory effect of small molecules is measured by tire effectiveness of the compounds to inhibit tins reaction (EC$_{50}$).

In this assay, the potency (EC$_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 1.25 nM of Full-length (FL)-PRMT5-MEP50 enzyme complex (recombinant proteins from baculovirus-transfected Sf21 cells: FL-PRMT5; MW=73837 kDa and FL-MEP50; MW=38614) and 1 μL of 150 μM S-(5'-Adenosyl)-L-Methionine Chloride (SAM). Plates were sealed and placed in a 37° C. humidified chamber for a 60 minutes pre-incubation with compound. Subsequently, each reaction was initiated by the addition of 1 μL 1× assay buffer containing 750 nM biotinylated H4R3(Mel) peptide. The final reaction in each well of 10 μL consists of 1.0 nM PRMT5-MEP50, 75 nM biotinylated-peptide, and 13 μM SAM. Methylation reactions were allowed to proceed for 150 minutes in a sealed plate at 37° C. Reactions were immediately quenched by the addition of 1 μL of 5% formic acid. Plates were then frozen and shipped to SAMDITM Tech Inc. to determine the percent conversion from H4R3(Mel) to H4R3(Me2). Dose-response curves were generated by plotting percent effect (% product conversion; Y-axis) vs.

Log 10 compound concentrations (X-axis). $EC_{50}$ values were determined by non-linear regression according to models for either sigmoidal (4 parameters) or biphasic (7 parameters) dose-response curves.

PRMT5 Cell Target Engagement (TE) Assay

The PRMT5 TE assay is a biomarker assay for identifying compounds that inhibit symmetric dimethylation of arginine (SDMA) of PRMT5 substrates. The following substrates have been reported for PRMT5: histone H2A and H4 R3, Histone H3 R2, Histone H3 R8, spliceosome Sm proteins, ribosomal protein RPS10, p53, FEN1, nudeoplasmin, nucleolin, EGFR and EBNA. The assay will focus on detecting symmetrically dimethylated nuclear proteins using high content imaging technology. Detection of the expression of symmetrically dimethylated nuclear proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 or Opera-Phenix measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells in 30 µl media and allowed to attach for 5 h. Media is ATCC-formulated Eagle's Minimum Essential Medium, Catalog No. 30-2003. To make the complete growth medium, the following components were added to the base medium: 0.01 mg/ml human recombinant insulin; fetal bovine serum to a final concentration of 10%. Additional 30 µl of media containing 2× compounds were added to each well. Cells were treated for 3 days in 37° C. $CO_2$ incubator. On day 3, cells were fixed with Cytofix, permeablized with 0.4% Triton-X-100/Cytofix, and washed with D-PBS without Ca/Mg. Cells were blocked with Licor Odyssey blocking reagent for 1 h at room temperature, followed by incubation with anti-SDMA (1:1000) antibody at 4° C. overnight. 1° antibody was removed, followed by three washings with DPBS without Ca/Mg and 0.05% Tween20. Hoechst (5 µg/ml), Cell Mask deep stain (1:2000) and Alexa488-conjugated goat anti-rabbit IgG (2 µg/mL) was added for 1 hour at room temperature. A final washing step (three washes) was performed before sealing plate for imaging on In Cell Analyzer 2200 or Opera-Phenix. Images from analyzer were uploaded to Columbus (at WP or BOS) for image analysis. $IC_{50}$ values were determined by 4 parameters robust fit of percent fluorescence units vs. (Logic) compound concentrations.

Representative compounds of the present invention were tested using the assay protocols described above. Results are provided in Table 6 below.

TABLE 6

When only one $EC_{50}$ is shown, the data was fit to a 4 parameters single site sigmodal model. When two $EC_{50}$s are shown, the data was fit to a 7 parameters biphasic model

| Ex. No. | Enzyme Methylation Assay ($EC_{50}$ or $EC_{50}\_1$, nM; $EC_{50}\_2$, nM) | TE Assay ($EC_{50}$, nM) |
| --- | --- | --- |
| 1 | 0.3, 76.7 | 208.1 |
| 2 | 2.2, 199.5 | 112.5 |

TABLE 6-continued

When only one $EC_{50}$ is shown, the data was fit to a 4 parameters single site sigmodal model. When two $EC_{50}$s are shown, the data was fit to a 7 parameters biphasic model

| Ex. No. | Enzyme Methylation Assay ($EC_{50}$ or $EC_{50}\_1$, nM; $EC_{50}\_2$, nM) | TE Assay ($EC_{50}$, nM) |
| --- | --- | --- |
| 3 | 6.0, 901.6 | 595.8 |
| 4 | 1.2, 568.9 | 50.5 |
| 5 | 26.2 | 10000.0 |
| 6 | 9.8 | 1126.0 |
| 7 | 2.5, 530.9 | 121.5 |
| 8 | 38310.0 | 3710.0 |
| 9 | 14.0, 2541 | 58.4 |
| 10 | 19.5, 16220 | 6016.0 |
| 11 | 0.7, 55.0 | 87.1 |
| 12 | 0.7 | 1.3 |
| 13 | 0.3 | 3.2 |
| 14 | 0.3 | 0.7 |
| 15 | 0.9 | 1.4 |
| 16 | 1.7 | 1.6 |
| 17 | 0.4 | 0.6 |
| 18 | 2.2 | 5.0 |
| 19 | 0.4, 50.1 | 8.4 |
| 20 | 0.7, 120.2 | 741.2 |
| 21 | 7.4 | 10000.0 |
| 22 | 10.1 | 5.9 |
| 23 | 58.3 | 41.9 |
| 24 | 1.5 | 17.4 |
| 25 | 1.3 | 8.4 |
| 26 | 59.6 | 10.5 |
| 27 | 47.7 | 55.0 |
| 28 | 0.7 | 1.4 |
| 29 | 0.6 | 0.9 |
| 30 | 0.3 | 0.5 |
| 31 | 0.7 | 53.4 |
| 32 | 0.6 | 5.6 |
| 33 | 0.8 | 13.5 |
| 34 | 0.5, 151.4 | 29.1 |
| 35 | 1.7 | 35.6 |
| 36 | 0.6, 15.3 | 81.1 |
| 37 | 0.4, 16.2 | 9.5 |
| 38 | 0.5 | 7.2 |
| 39 | 21.9 | 2435.0 |
| 40 | 57.9 | 10000.0 |
| 41 | 1.2, 660.7 | 122.6 |
| 42 | 0.8 | 2.4 |
| 43 | 0.7 | 2.4 |

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

What is claimed is:

1. A compound having formula I (I)

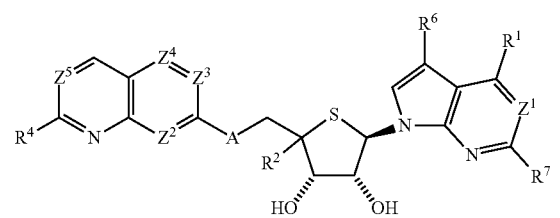

or a pharmaceutically acceptable salt thereof, wherein

A is O or CH$_2$;

R$^1$ is halogen, NH$_2$, OC$_{1-6}$alkyl, NHCH$_3$, CHF$_2$, C$_{1-6}$alkyl, cyclopropyl, CH$_2$OH, or C(CH$_3$)$_2$OH;

R$^2$ is H, C$_{1-6}$alkyl, CF$_3$ or CHF$_2$;

R$^3$ is H, halogen, CH$_3$, CF$_3$, or CHF$_2$, and R$^4$ is H or NHR$^5$, or R$^3$ and R$^4$ together with the atom to which they are attached form a 5-membered saturated ring containing zero or one N atom, wherein the ring is unsubstituted or substituted with CH$_3$;

R$^5$ is H, CH$_3$, C$_2$H$_5$, CH$_2$CH$_2$CH$_3$, CH(CH$_3$)$_2$, CH$_2$CHF$_2$, CH$_2$CF$_3$, or CH$_2$—C$_{3-8}$cycloalkyl;

R$^6$ is H, C$_{1-4}$alkyl, or halogen;

R$^7$ is H, NH$_2$, or C$_{1-6}$alkyl;

Z$^1$ is CH or N;

Z$^2$ is CH or N;

Z$^3$ is CH or N;

Z$^4$ is CH or N; and

Z$^5$ is CR 3 or N.

2. The compound of claim 1, or a pharmaceutically acceptable salt thereof, wherein R$^1$ is NH$_2$, Cl, NHCH$_3$, OCH$_3$, or CH$_3$.

3. The compound of claim 1, or a pharmaceutically acceptable salt thereof, wherein R$^2$ is H or CH$_3$.

4. The compound of claim 1, or a pharmaceutically acceptable salt thereof, wherein R$^4$ is NH$_2$.

5. The compound of claim 1, or a pharmaceutically acceptable salt thereof, wherein R$^4$ is NHCH$_2$CHF$_2$.

6. The compound of claim 1, or a pharmaceutically acceptable salt thereof, wherein R$^5$ is H.

7. The compound of claim 1, or a pharmaceutically acceptable salt thereof, wherein R$^5$ is CH$_2$CHF$_2$.

8. The compound of claim 1, or a pharmaceutically acceptable salt thereof, wherein R$^6$ is H, F or CH$_3$.

9. The compound of claim 1, or a pharmaceutically acceptable salt thereof, wherein R$^7$ is CH$_3$ or NH$_2$.

10. The compound of claim 1, or a pharmaceutically acceptable salt thereof, having the formula

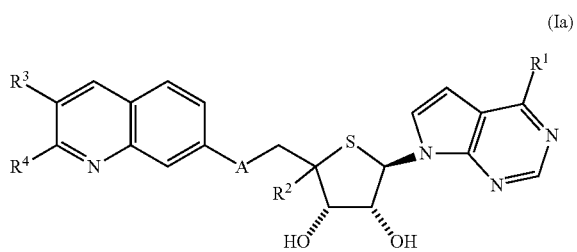

(Ia)

or a pharmaceutically acceptable salt thereof, wherein

A is O or CH$_2$;

R$^1$ is halogen, NH$_2$, or OC$_{1-6}$alkyl;

R$^2$ is H or C$_{1-6}$alkyl;

R$^3$ is H, CH$_3$, or halogen;

R$^4$ is H or NHR$^5$; and

R$^5$ is H or CH$_2$—C$_{3-8}$cycloalkyl.

11. The compound of claim 10, or a pharmaceutically acceptable salt thereof, having the formula

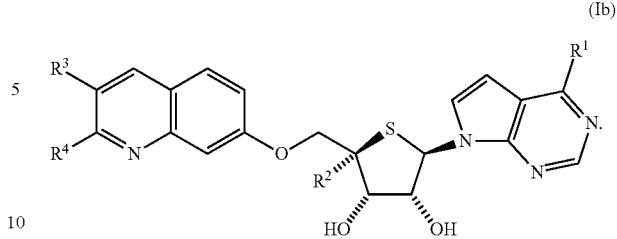

(Ib)

12. The compound of claim 10, or a pharmaceutically acceptable salt thereof, having the formula

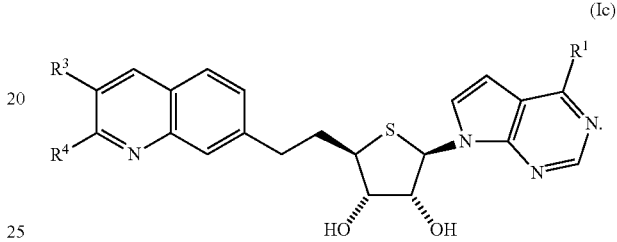

(Ic)

13. A compound of claim 10, or a pharmaceutically acceptable salt thereof, wherein A is 0 or CH$_2$;

R$^1$ is C$_1$, NH$_2$, or OCH$_3$;

R$^2$ is H or CH$_3$;

R$^3$ is H, Br, F, CH$_3$, or Cl; and

R$^4$ is NH$_2$ or NH—CH$_2$-cyclopropyl.

14. The compound of claim 1, or a pharmaceutically acceptable salt thereof, which is (2R,3S,4R,5R)-2-(((2-amino-3-bromoquinolin-7-yl)oxy)methyl)-5-(4-amino-7H-pyrrolo[2,3-d]pyrimidin-7-yl)tetrahydrothiophene-3,4-diol, 7-[5-O-(2-amino-3-chloroquinolin-7-yl)-4-thio-beta-D-ribofuranosyl]-7H-pyrrolo[2,3-d]pyrimidin-4-amine, 7-[5-O-(2-amino-3-fluoroquinolin-7-yl)-4-thio-beta-D-ribofuranosyl]-7H-pyrrolo[2,3-d]pyrimidin-4-amine, 7-(5-O-{2-[(cyclopropylmethyl)amino]quinolin-7-yl}-4-thio-beta-D-ribofuranosyl)-7H-pyrrolo[2,3-d]pyrimidin-4-amine, (2R,3S,4R,5R)-2-(((2-amino-3-chloroquinolin-7-yl)oxy)methyl)-5-(4-amino-7H-pyrrolo[2,3-d]pyrimidin-7-yl)tetrahydrothiophene-3,4-diol, (2R,3S,4R,5R)-2-(((2-amino-3-bromoquinolin-7-yl)oxy)methyl)-5-(4-chloro-7H-pyrrolo[2,3-d]pyrimidin-7-yl)-2-methyltetrahydrothiophene-3,4-diol, (2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrothiophene-3,4-diol, (2R,3S,4R,5R)-2-(((2-((cyclopropylmethyl)amino)quinolin-7-yl)oxy)methyl)-5-(4-methoxy-7H-pyrrolo[2,3-d]pyrimidin-7-yl)tetrahydrothiophene-3,4-diol, (2R,3S,4R,5R)-2-(((2-((cyclopropylmethyl)amino)quinolin-7-yl)oxy)methyl)-5-(4-methyl-7H-pyrrolo[2,3-d]pyrimidin-7-yl)tetrahydrothiophene-3,4-diol, (2R,3S,4R,5R)-2-(((2-aminoquinolin-7-yl)oxy)methyl)-5-(4-methoxy-7H-pyrrolo[2,3-d] pyrimidin-7-yl)tetrahydrothiophene-3,4-diol, (2R,3R,4S,5R)-2-(4-amino-7H-pyrrolo[2,3-d]pyrimidin-7-yl)-5-(((2-aminoquinolin-7-yl)oxy)methyl)tetrahydrothiophene-3,4-diol, (2R,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol,
(2S,3S,4R,5R)-2-(2-(2-amino-3-bromoquinolin-7-yl)ethyl)-5-(4-amino-7H-pyrrolo[2,3-d]pyrimidin-7-yl)tetrahydrothiophene-3,4-diol,
(2R,3R,4S,5R)-2-(4-amino-7H-pyrrolo[2,3-d]pyrimidin-7-yl)-5-(2-(2-aminoquinolin-7-yl)ethyl)tetrahydrothiophene-3,4-diol,
(2R,3R,4S,5S)-2-(4-amino-7H-pyrrolo[2,3-d]pyrimidin-7-yl)-5-(2-(2-aminoquinolin-7-yl)ethyl)tetrahydrothiophene-3,4-diol,
(2S,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol,
(2R,3S,4R,5R)-2-[2-(2-aminoquinolin-7-yl)ethyl]-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-bromoquinolin-7-yl)ethyl)-5-(4-methyl-7H-pyrrolo[2,3-d]pyrimidin-7-yl)tetrahydrothiophene-3,4-diol,
(2R,3S,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol,
(2S,3S,4R,5R)-2-{2-[2-amino-3-(trifluoromethyl)quinolin-7-yl]ethyl}-5-(4-methyl-7H-pyrrolo[2,3-d]pyrimidin-7-yl)tetrahydrothiophene-3,4-diol,
(2R,3S,4R,5R)-2-[2-(2-amino-3-fluoroquinolin-7-yl)ethyl]-5-(4-methyl-7H-pyrrolo[2,3-d] pyrimidin-7-yl)tetrahydrothiophene-3,4-diol,
(2S,3S,4R,5R)-2-[2-(2-amino-3-fluoroquinolin-7-yl)ethyl]-5-(4-methyl-7H-pyrrolo[2,3-d]pyrimidin-7-yl)tetrahydrothiophene-3,4-diol,
(2R,3S,4R,5R)-2-[2-(2-amino-3-chloroquinolin-7-yl)ethyl]-5-(4-methyl-7H-pyrrolo[2,3-d] pyrimidin-7-yl)tetrahydrothiophene-3,4-diol,
(2S,3S,4R,5R)-2-[2-(2-amino-3-chloroquinolin-7-yl)ethyl]-5-(4-methyl-7H-pyrrolo[2,3-d] pyrimidin-7-yl)tetrahydrothiophene-3,4-diol,
(2R,3S,4R,5R)-2-(2-{2-[(2,2-difluoroethyl)amino] quinolin-7-yl}ethyl)-5-(4-methyl-7H-pyrrolo[2,3-d]pyrimidin-7-yl)tetrahydrothiophene-3,4-diol,
(2S,3S,4R,5R)-2-(2-{2-[(2,2-difluoroethyl)amino] quinolin-7-yl}ethyl)-5-(4-methyl-7H-pyrrolo[2,3-d]pyrimidin-7-yl)tetrahydrothiophene-3,4-diol,
(2R,3S,4R,5R)-2-(2-(2-amino-3-methyl quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-methyl quinolin-7-yl)ethyl)-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-5-(4-amino-7H-pyrrolo[2,3-d]pyrimidin-7-yl)-2-methyltetrahydrothiophene-3,4-diol,
(2R,3S,4R,5R)-2-(2-(2-amino-3-bromoquinolin-7-yl)ethyl)-5-(4-chloro-7H-pyrrolo[2,3-d]pyrimidin-7-yl)-2-methyltetrahydrothiophene-3,4-diol,
(2R,3S,4R,5R)-2-(2-(2-amino-3-bromoquinolin-7-yl)ethyl)-2-methyl-5-(4-methyl-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-2-methyl-5-(4-(methyl amino)-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-5-(4-amino-5-methyl-7H-pyrrolo[2,3-d]pyrimidin-7-yl)tetrahydrothiophene-3,4-diol,
(2R,3R,4S,5R)-2-(4-amino-2-methyl-7H-pyrrolo[2,3-d]pyrimidin-7-yl)-5-(2-(2-amino-3-bromoquinolin-7-yl)ethyl)tetrahydrothiophene-3,4-diol,
(2R,3S,4R,5R)-2-(2-(2-amino-3-bromoquinolin-7-yl)ethyl)-5-(4-(methyl amino)-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-5-(4-amino-5-fluoro-7H-pyrrolo[2,3-d]pyrimidin-7-yl)tetrahydrothiophene-3,4-diol,
(2R,3S,4R,5R)-2-(2-(2-amino-3-bromoquinolin-7-yl)ethyl)-5-(2-amino-4-methyl-7H-pyrrolo[2,3-d]pyrimidin-7-yl)tetrahydrothiophene-3,4-diol,
(2S,3S,4R,5R)-2-(2-((R)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-((S)-2-methyl-2,3-dihydro-1H-pyrrolo[2,3-b]quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-(difluoromethyl)quinolin-7-yl)ethyl)-5-(4-methyl-7H-pyrrolo[2,3-d]pyrimidin-7-yl)tetrahydrothiophene-3,4-diol,
(2S,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol, or
(2R,3S,4R,5R)-2-(2-(2-amino-3-chloroquinolin-7-yl)ethyl)-5-(4-amino-7H-pyrrolo[2,3-d]pyrimidin-7-yl)tetrahydrothiophene-3,4-diol.

15. A composition for treating cancer ameliorated by inhibition of PRMT5 comprising a compound of claim 1, or a pharmaceutically acceptable salt thereof, and a pharmaceutically acceptable carrier.

16. A method for treating cancer ameliorated by inhibition of PRMT5 comprising administering to a patient in need thereof a composition of claim 15.

17. A method for treating cancer ameliorated by inhibition of PRMT5 comprising administering to a patient in need thereof a compound of claim 1, or a pharmaceutically acceptable salt thereof.

* * * * *